US008951768B2

(12) United States Patent
Iadonato et al.

(10) Patent No.: US 8,951,768 B2
(45) Date of Patent: *Feb. 10, 2015

(54) MUTATIONS IN OAS1 GENES

(75) Inventors: Shawn P. Iadonato, Seattle, WA (US);
Charles L. Magness, Seattle, WA (US);
P. Campion Fellin, Seattle, WA (US);
Christina A. Scherer, Seattle, WA (US);
Tory Hagen, Tacoma, WA (US); Amy Olson, Seattle, WA (US)

(73) Assignee: Kineta Two, LLC, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/180,132

(22) Filed: Jul. 11, 2011

(65) Prior Publication Data

US 2012/0070424 A1    Mar. 22, 2012

Related U.S. Application Data

(63) Continuation of application No. 12/248,810, filed on Oct. 9, 2008, now Pat. No. 8,030,046, which is a continuation of application No. 11/416,790, filed on May 3, 2006, now abandoned.

(60) Provisional application No. 60/677,680, filed on May 4, 2005.

(51) Int. Cl.
*C12N 9/12* (2006.01)
*A61K 38/00* (2006.01)
*C12N 9/10* (2006.01)
*C12N 9/88* (2006.01)
*C12Q 1/68* (2006.01)

(52) U.S. Cl.
CPC ............ *C12N 9/1241* (2013.01); *C12N 9/1077* (2013.01); *C12N 9/88* (2013.01); *C12Q 1/6883* (2013.01); *C12Q 2600/156* (2013.01)
USPC .......................... 435/194; 435/183; 424/94.5

(58) Field of Classification Search
None
See application file for complete search history.

(56) References Cited

U.S. PATENT DOCUMENTS

| | | | | |
|---|---|---|---|---|
| 4,863,873 | A | 9/1989 | Matson | 436/63 |
| 5,266,459 | A | 11/1993 | Beutler | 435/6 |
| 5,480,640 | A | 1/1996 | Morales | |
| 5,866,781 | A | 2/1999 | Silverman | |
| 6,558,955 | B1 | 5/2003 | Kristal | 436/63 |
| 6,566,328 | B1 | 5/2003 | Rosen | 514/12 |
| 7,354,908 | B2 | 4/2008 | Mohapatra | |
| 8,030,046 | B2 | 10/2011 | Iadonato | 435/194 |
| 8,088,907 | B2 | 1/2012 | Iadonato et al. | |
| 8,192,973 | B2 | 6/2012 | Iadonato et al. | |
| 8,551,772 | B2 | 10/2013 | Iadonato et al. | |
| 2001/0001290 | A1 | 5/2001 | Lau | 435/235.1 |
| 2001/0001709 | A1 | 5/2001 | Lau | 435/235.1 |
| 2001/0034023 | A1 | 10/2001 | Stanton | 435/6 |
| 2003/0044783 | A1 | 3/2003 | Williams | 435/6 |
| 2003/0165920 | A1 | 9/2003 | Chou | 435/6 |
| 2003/0165921 | A1 | 9/2003 | Tang | 435/6 |
| 2003/0235575 | A1 | 12/2003 | Matzuk | 424/94.61 |
| 2004/0009152 | A1 | 1/2004 | Mohapatra | 424/93.2 |
| 2005/0191649 | A1 | 9/2005 | Iadonato et al. | |
| 2006/0275802 | A1 | 12/2006 | Iadonato et al. | |
| 2009/0291074 | A1 | 11/2009 | Iadonato et al. | |
| 2013/0142773 | A1 | 6/2013 | Iadonato et al. | |

FOREIGN PATENT DOCUMENTS

| | | |
|---|---|---|
| DE | 10122206.8 | 11/2002 |
| RU | 2108386 C1 | 4/1998 |
| WO | WO91/06309 | 5/1991 |
| WO | WO91/11520 | 8/1991 |
| WO | WO93/07283 | 4/1993 |
| WO | WO93/24640 | 12/1993 |
| WO | WO94/20069 | 9/1994 |
| WO | WO95/22245 | 8/1995 |
| WO | WO99/13075 | 3/1999 |
| WO | WO01/66689 | 9/2001 |
| WO | WO01/79556 | 10/2001 |
| WO | WO/02/081741 | 10/2002 |
| WO | WO/02/090552 | 11/2002 |
| WO | WO03/089003 | 10/2003 |
| WO | WO/04/000998 | 12/2003 |
| WO | WO2005/040428 | 5/2005 |
| WO | WO2006/119363 | 11/2006 |

OTHER PUBLICATIONS

Alter et al., *J. Acquired Immune Deficiency Syndrome Human Retrovirology* 18(Suppl 1):S6-S10, 1998.
Bonnevie-Neilsen et al., *Clinical Immunol.* 96(1):11-18, 2000.
Buckwold et al., *Antiviral Res.* 60:1-15, 2003.
Chousterman et al., *J. Bio. Chem.* 262(10):4806-4811, 1987.
Crance et al., *Antiviral Res.* 58(1):73-79, 2003.
Dansako et al., *Virus Res.* 97:17-30, 2003.
Eskildsen et al., *Nucleic Acids Res.* 31(12):3166-3173, 2003.
Field et al., *Diabetes* 54:1588-1591, 2005.
Fowke et al., *The Lancet England* 348(9038):1347-1351, 1996.
Ghosh et al., *J. Bio. Chem.* 276(27):25447-25455, 2001.
Ghosh et al., *J. Bio. Chem.* 286(23):15293-15299, 1991.
Hamano et al., *Biochem. Biophys. Res. Comm.* 329(4):1234-1239, 2005.
Hassel, *Molecular Carcinogenesis* 5:41-51, 1992.
Hitman et al., *Immunogenetics* 30(6):427-431, 1989.
Hovanessian et al., *EMBO J.* 6(5):1273-1280, 1987.
Hovnanian et al., *Genomics* 52:267-277, 1998.
Justesen et al., *CMLS Cellular and Molecular Lie Sciences* 57(11):1593-1612, 2000.
Justesen et al., *Nucleic Acids Res.* 8(14):3073-3085, 1980.
Kakuta et al., *J. Interferon & Cytokine Res.* 22:981-993, 2002.
Kimchi et al., *Eur. J. Biochem.* 114:5-10, 1981.
Knapp et al., *Genes Immun.* 4(6):411-419, 2003.
Knobler et al., *Am. J. Gastroenterol.* 98(12):2751-2756, 2003.

(Continued)

Primary Examiner — Richard Hutson
(74) Attorney, Agent, or Firm — Lee & Hayes, PLLC; C. Rachal Winger; Rachel A. Haller

(57) ABSTRACT

Modified amino acid sequences of OAS1 proteins in non-human primates, and genes related thereto, are provided.

10 Claims, 12 Drawing Sheets

(56) References Cited

OTHER PUBLICATIONS

Marie et al., *Biochem. Biophys.Res. Comm.* 160(2):580-587. 1989.
Marie et al., *J. Bio. Chem.* 167(14):9933-9939, 1992.
Marie et al., *EurJ Biochem.* 262(1):155-165, 1999.
Mashimo et al., *Genomics* 82537-552, 2003.
McKusick et al., 164350, *Online Medelian Inheritance in Man*, 1986.
Muller et al., *J. Bio. Chem.* 265(7):3803-3808, 1990.
Olson, *Am. J. Hum. Genet.* 64:18-23, 1999.
Perelygin et al., *PNAS* 99(14):9322-9327, 2002.
Player et al., *Pharmacol. Ther.* 78(2):55-113, 1998.
Rasooly, 603350, *Online Medelian Inheritance in Man*, 1998.
Rebouillat and Hovanessian, *J. Interferon & Cytokine Res.* 19:295-308, 1999.
Replicated Natural Resistance, http://www.illumigen.com/technologly/html, 2003.
Rysiecki et al., *J. Interferon Res.* 9:649-657, 1989.
Salzberg et al., *J. Cell Science* 109:1517-1526, 1996.
Samuel, *PNAS* 99(18):11555-11557, 2002.
Schwartz et al., *Mol. Cell.Bio.* 9(9):3897-3903, 1989.
Taguchi et al., *J. General Virology* 85:959-969, 2004.
Urosevic, *Immunol. Cell Bio.* 81(3):224, 2003.
Wells et al., *Experimental Cell Res.* 159:27-36, 1985.
Xiang et al., *Cancer Res.* 63:6795-6801, 2003.
Zubriski et al., *FASEB J.* 16(4):A152, 2002.
Zullo et al., *Cell* 43(2):793-800, 1985.
Accession No. NP_001027581.1—Pruitt, K., et. al., Reference Sequence (RefSeq) Database (http://www.ncbi.nlm.nih.gov/books/NBK21091/), Release 16 dated Mar. 17, 2006.
Accession No. NP_002525.1—Pruitt, K., et. al., Reference Sequence (RefSeq) Database (http://www.ncbi.nlm.nih.gov/books/NBK21091/), Release 16 dated Mar. 17, 2006.
Accession No. NP_058132.1—Pruitt, K., et. al., Reference Sequence (RefSeq) Database (http://www.ncbi.nlm.nih.gov/books/NBK21091/), Release 16 dated Mar. 17, 2006.
Accession No. P00973—Ota,T., et al., "Complete sequencing and characterization of 21,243 full-length human cDNAs," Nat. Genet. 36:40-45 (2004).
Genbank Accession No. NM 002534, May 2000.
Bae, et al., Journal of Biological Chemistry, 275, No. 18, pp. 13588-13596, 2000.
Marie, et al, The Journal of Biological Chemistry, 267(14):9933-9939, 1992.
Mashimo, et al, PNAS, 99(17):11311-11316, 2002.
Wathelet, et al., FEBS Letters, vol. 196, 113-120, Feb. 1986.
Accession No. A22842. Jul. 21, 2000.
Office Action for Japanese application 2006536883 citing WO93/07283 (JP10-506001).
Sigma Catalog, 1993 (p. 1089, Catalog No. G5149).
Accession No. AC004551, Apr. 11, 1998.
GenBank: BAA00047.1 Shiojiri,S., Fukunaga,R., Ichii,Y. and Sokawa,Y. "Structure and expression of a cloned cDNA for human" (2'-5')oligoadenylate synthetase J. Biochem. 99 (5), 1455-1464 (1986).
Accession No. Accession AAP36147.1, May 13, 2003, Kalnine,N., Chen,X., Rolfs,A., Halleck,A., Hines,L., Eisenstein,S., Koundinya,M., Raphael,J., Moreira,D., Kelley,T., LaBaer,J., Lin,Y., Phelan,M. and Farmer,A. Cloning of human full-length CDSs in BD Creator(TM) System Donor vector.
GenBank: CAA26633.12 Sep 9, 2004, Benech,P., Mory,Y., Revel,M. and Chebath,J. "Structure of two forms of the interferon-induced (2'-5') oligo A synthetase of human cells based on cDNAs and gene sequences" EMBO J. 4 (9), 2249-2256 (1985).
GenBank: AAB59553.1 Dec 14, 2000 ? Benech,P., Mory,Y., Revel,M. and Chebath,J. "Structure of two forms of the interferon-induced (2'-5') oligo A synthetase of human cells based on cDNAs and gene sequences" EMBO J. 4 (9), 2249-2256 (1985).
Genbank Accession No. NM 002534, PRI= Jan 10, 2014, Saunders,M.E., Gewert,D.R., Tugwell,M.E., McMahon,M. and Williams,B.R., Human 2-5A synthetase: characterization of a novel cDNA andcorresponding gene structure, EMBO J. 4 (7), 1761-1768 (1985).
Australian Examiner's Report, Nov. 23, 2010 for Serial No. 2004283294.
Bae, et al., "Arginine-rich anti-vascular endothelial growth factor peptides inhibit tumor growth and metastasis by blocking angiogenesis," Journal of Biological Chemistry, 275, No. 18, pp. 13588-13596, 2000.
Database DBSNP [Online] http://www.ncbi.nlm.nih.gov/snp/?term=7955146 NCKI; retrieved from NCBI SNP Database accession No. 7955146, originally accessed for European Search Report on Jun. 12, 2009, original date of publication unknown.
Marie, et al, "The 69-kDa 2-5A synthetase is composed of two homologous and adjacent functional domains" The Journal of Biological Chemistry, 267(14):9933-9939, 1992.
Mashimo, et al, "A nonsense mutation in the gene encoding 2'-5'-oligoadenylate synthetase/L1 isoform is associated with West Nile virus susceptibility in laboratory mice" PNAS, 99(17):11311-11316, 2002.
Ngo et al, Computational Complexity, Protein Structure Prediction, and the Levinthal Paradox, in the Protein Folding Problem and Tertiary Structure Prediction, 1994, Merz, et al (ed.), Birkhauser, Boston MA, p. 433 and 492-495.
Qiagen Product Guide, 1997, p. 106-110.
Schattner, A et al:, "No evidence for autoimmunity in schizophrenia", Journal of Autoimmunity: 9(5): 661-666 1996.
Wathelet, et al., "Full-length sequence and expression of the 42 kDa 2-5A synthetase induced by human interferon," FEBS Letters, vol. 196, 113-120, Feb. 1986.
Zarghami, M et al: "Studies on the Association between 2'5'-Oligoadenylate Synthetase and Type 1 Diabetes" Tissue Antigens, 59(2 Suppl):53 2002.
Accession No. A22842. PRI=Jul. 21, 2000, Benech,P., Mory, Y., Revel,M. and Chebath,J. "Structure of two forms of the interferon-induced (2'-5') oligo A synthetase of human cells based on cDNAs and gene sequences," EMBO J. 4 (9), 2249-2256, 1985.
Office Action for Russian application 2007144986 citing WO91/11520 (RU2108386) (Apr. 10, 1998).
Office Action for Japanese application 2006536883 citing WO93/07283 (JP10-506001) mailed Nov. 15, 2011.
Lucas, et al., "Infection of mouse neurones by West Nile virus is modulated by the interferon-inducible 2'-5' oligoadenylate synthetase 1b protein," Immunology and Cell Biology, vol. 81, No. 3, Jun. 2003, pp. 230-236.
Mashimo, et al., "A nonsense mutation in the gene encoding 2'-5'-oligoadenylate sythetase/L1 isoform is associated with West Nile virus susceptibility in laboratory mice," PNAS, vol. 99, No. 17, 2002, pp. 11311-11316.
Office Action mailed Jun. 24, 2014 in Korean Application No. 10-2007-7028236.
Office Action dated Apr. 1, 2010 in Russian Application No. 2007144986.
Office Action dated Apr. 10, 2013 in Israel Application No. 187079.
Office Action dated Feb. 10, 2011 in Russian Application No. 2007144986.
Office Action dated Jan. 31, 2014 in Canadian Applicaiton No. 2607575.
Office Action dated Jul. 21, 2011 in Russian Application No. 2007144986.
Office Action mailed Jun. 19, 2014 in New Zealand Application No. 603105.
Office Action dated Mar. 9, 2014 in Israel Application No. 187079.
Office Action dated May 26, 2009 in Australian Application No. 2004283294.
Office Action mailed on Apr. 3, 2014 in U.S. Appl. No. 13/676,928.
Office Action mailed Aug. 3, 2010 in Japanese Application No. 2006-536883.
Office Action mailed Jan. 8, 2013 in Japanese Application No. 2006-536883.

(56) References Cited

OTHER PUBLICATIONS

Office Action mailed Jan. 7, 2014 in Japanese Application No. 2012-111782.
Re-Examination Report mailed Jun. 17, 2014 in Japanese Application No. 2006-536883.
Richard, et al., "Cell-penetrating Peptides. A Reevaluation of the Mechanism of Cellular Uptake," Journal of Biological Chemistry, Vo. 278, No. 1, Jan. 3, 2003, pp. 585-590.
Sarkar, et al., "The Nature of the Catalytic Domain of 2'-5'-Oligoadenylate Synthetases," Journal of Biological Chemistry, vol. 274, No. 36, Sep. 1999, pp. 25535-25542.
Strausberg, et al., "Generation and Initial Analysis of More than 15,000 Full-Length Human and Mouse cDNA Sequences", PNAS, vol. 99 (26), pp. 16899-16903, Dec. 24, 2002.
Yakub, et al., "Single Nucleotide Polymorphisms in Genes for 2'-5'-Oligoadenylate Synthetase and RNase L in Patients Hospitalized with West Nile Virus Infection," Journal of Infectious Diseases, vol. 192, No. 10, Nov. 2005, pp. 1741-1748.

FIGURE 1

PREFERRED THERAPEUTIC FORM OF OAS1

SEQ ID NO: 1

```
1   MMDLRNTPAKSLDKFIEDYLLPDTCFRMQINHAIDIICGFLKERCFRGSSYPVCVSKVVK  60
61  GGSSGKGTTLRGRSDADLVVFLSPLTTFQDQLNRRGEFIQEIRRQLEACQRERAFSVKFE  120
121 VQAPRWGNPRALSFVLSSLQLGEGVEFDVLPAFDALGQLTGSYKPNPQIYVKLIEECTDL  180
181 QKEGEFSTCFTELQRDFLKQRPTKLKSLIRLVKHWYQNCKKKLGKLPPQYALELLTVYAW  240
241 ERGSMKTHFNTAQGFRTVLELVINYQQLCIYWTKYYDFKNPIIEKYLRRQLTKPRPVILD  300
301 PADPTGNLGGGDPKGWRQLAQEAEAWLNYPCFKNWDGSPVSSWILL  346
```

FIGURE 2
LIST OF AMINO ACID SUBSTITUTIONS USEFUL IN THERAPEUTIC FORMS OF OAS1

| Position | Amino Acid Substitutions |
|---|---|
| 1 | M or - (Deleted) |
| 31 | D or N |
| 115 | L or F |
| 127 | G or R |
| 162 | S or G |
| 295 | R or T |
| 315 | G or R |

FIGURE 3
LIST OF PRIMATE AMINO ACID MODIFICATIONS USEFUL IN THERAPEUTIC FORMS OF OAS1

| Position | Amino Acid Substitutions |
|---|---|
| 24 | Lys or Thr |
| 25 | His or Cys |
| 28 | Thr or Lys or Met |
| 36 | Thr or Ile |
| 47 | Gln or Arg |
| 53 | Ala or Val |
| 54 | Arg or Cys |
| 54 | Arg or His or Cys |
| 64 | Phe or Ser |
| 69 | Ala or Thr |
| 69 | Ala or Ser or Thr |
| 74 | Ile or Ser |
| 104 | Lys or Arg |
| 108 | Val or Ala |
| 112 | Glu insertion |
| 113 | Ser or Arg |
| 114 | Ile or Ala |
| 116 | Arg or Ser or Ala |
| 117 | Glu or Val |
| 118 | Val or Lys |
| 119 | Termination or Phe |
| 127 | Asp or Gly |
| 130 | Cys or Arg |
| 139 | Phe or Leu |
| 142 | Arg or Gly |
| 160 | Ile or Thr |
| 161 | Asp or Gly |
| 166 | Asp or Asn |
| 175 | Lys or Glu |
| 179 | Tyr or Asp |
| 200 | Glu or Gln |
| 226 | Pro insertion |
| 242 | Gln or Arg |
| 246 | Glu or Lys |
| 248 | Asp or His |
| 250 | Ile or Asn |
| 254 | Glu or Gly |
| 274 | Val or Lys |
| 279 | Glu or Lys |
| 282 | Ser or Ile |
| 284 | Lys or Glu |
| 288 | Ser or Arg |
| 289 | Arg or Arg |
| 292 | Glu or Thr |
| 292 | Arg or Thr |

FIGURE 3 (cont.)

| | |
|---|---|
| 292 | Ser or Thr |
| 314 | Ile or Lys |
| 335 | Termination or Trp |
| 347+ | Thr or Ala |
| 347^ | Pro or Thr |
| 349+ | Ser or Ser |
| 350+ | Asp or Asn |
| 352+ | Gly or Glu or Ala |
| 353+ | Arg or Asp |
| 354+ | Termination or Asp |
| 356+ | Ser or Thr |
| 357+ | Tyr or Asp |
| 361+ | Met or Arg |
| 361^ | Glu or Gly |
| 363* | Lys or Glu |
| 363+ | Pro or Gln |
| 364+ | Gln or Lys |
| 364^ | Val or Leu |
| 365+ | His or Tyr |
| 369+ | Gln or Arg or Gly |
| 371+ | Tyr or His |
| 372^ | Ala or Ala |
| 373+ | Cys or Tyr |
| 374+ | Ser or Pro |
| 375+ | Tyr or His |
| 378+ | Gln or His |
| 379+ | Ser or Arg |
| 382+ | Ile or Thr |
| 384^ | His or Gln |
| 385^ | Leu or Phe |
| 388+ | Ala or Thr |
| 389+ | Arg or Pro |
| 394+ | Asn or Asp |
| 399^ | Arg or Ser |

\* Positions indicated with \* refer to forms of OAS1 that are carboxyl-terminus homologous to Genbank accession NP_002525.1 (for example SEQ ID NO:3).

+ Positions indicated with + refer to forms of OAS1 that are carboxyl-terminus homologous to Genbank accession NP_058132.1 (for example SEQ ID NO:2).

^ Positions indicated with ^ refer to forms of OAS1 that are carboxyl-terminus homologous to Genbank accession NP_001027581.1 (for example SEQ ID NO:4).

All other unmarked positions refer to all forms of OAS1.

FIGURE 4
PRIMATE MUTATIONS IN OAS1

| Position of first base in mutation in Reference Genbank accession NT_009775.15 | Ateles geoffroyi (agegeo01) | Gorilla gorilla (ggogor01) | Lagothrix lagotricha (llaglago01) | Macaca arctoides (marcto01) | Macaca fascicularis (mfascio01) | Macaca mulatta (mmulat01) | Macaca nemestrina (mnemens101) | Pongo pygmaeus abelii (ppabeli01) | Pongo pygmaeus abelii (ppabeli02) | Pan Paniscus (ppanisco01) | Pan paniscus (ppanisco02) | Pan troglodytes (ptroglo001) | Pan troglodytes verus (ptverus01) | Pan troglodytes verus (ptverus02) | Saguinus labiatus (slabiato1) | Codon Alt(s)/Ref | Amino Acid Position | Codon Position | Amino Acids Variants (Alternates/Ref) |
|---|---|---|---|---|---|---|---|---|---|---|---|---|---|---|---|---|---|---|---|
| 3914389 | | | | | | | | | | A/G | | | | | | CTA/CTG | 12 | 3 | Leu/Leu |
| 3914424 | | | | CA/TG | | | | | | | | | | | | AAG/ACG | 24 | 2 | Lys/Thr |
| 3914426 | | | | T/C | | | | | CA/TG | | | | | | | CAT/TGT | 25 | 1+2 | His/Cys |
| 3914431 | | | | | | | | | | | | | | | | TTT/TTC | 26 | 3 | Phe/Phe |
| 3914436 | | | | | | | | | | C/T | | A/T | A/T | A/C | | ACG/AAG/ATG | 28 | 2 | Thr/Lys/Met |
| 3914455 | | | | | | | | C/T | C/T | | | | | | | ATC/ATT | 34 | 3 | Ile/Ile |
| 3914460 | | | | | | | | C/T | C/T | | | | | | | ACC/ATC | 36 | 2 | Thr/Ile |
| 3914493 | | | | | | | | | | | | A/G | A/G | A/G | | CAA/CGA | 47 | 2 | Gln/Arg |
| 3914511 | | | | | | | | C/T | T/T | | | | | | | GCG/GTG | 53 | 2 | Ala/Val |
| 3914512 | | | | AC/GT | | | | | | | | | | | | GTACGT/GTGTGT | 53-54 | 3+1 | ValArg/ValCys |
| 3914513 | | | | | | | | CG/TG | CA/TG | | | | CA/TG | CA/TG | | CGT/CAT/TGT | 54 | 2 | ArgHis/Cys |
| 3915860 | | | | | | | | | | | | | | | TC/CA | TTC/TCA | 64 | 2+3 | Phe/Ser |
| 3915861 | G/A | | G/A | T/A | T/A | T/A | T/A | G/A | G/A | | | | | | | TCG/TCT/TCA | 64 | 3 | Ser/Ser |
| 3915867 | A/G | | A/G | A/G | A/G | A/G | A/G | | | | | | | | A/G | AAA/AAG | 66 | 3 | Lys/Lys |
| 3915873 | | | TG/CA | | | | | | | | | | | | | ACTGCC/ACCACC | 68-69 | 3+1 | ThrAla/ThrThr |
| 3915874 | G/A | | | | | | | G/A | G/A | | | | | | G/C | GCC/TCC/ACC | 69 | 1 | Ala/Ser/Thr |
| 3915886 | A/C | | A/C | | | | | | | | | | | | A/C | AGA/CGA | 73 | 1 | Arg/Arg |
| 3915889 | | | | | | | | | | | | | | | AT/TC | ATT/TCT | 74 | | Ile/Ser |
| 3915980 | | | | | | | | A/G | A/G | | | | | | | AAA/AGA | 104 | 2 | Lys/Arg |
| 3915992 | | | | | | | | | | T/C | T/C | | | | | GTC/GCC | 108 | 2 | Val/Ala |
| 3916003 | | | | | | | | --/AG | --/AG | GAG/-- | GAG/-- | GAG/-- | GAG/-- | GAG/-- | | GAG/-- | 112 | 1 | Glu/-- |
| 3916008 | | | | | | | | | | | | G/T | | | | AG--CA/AGAGCA | 113-119 | Frameshift | SerIlePheArgGluVal Term/ArgAlaPheSer ValLysPhe |
| 3916015 | | | | | | | | | | | | | | | | GCC/TCC | 116 | 1 | Ala/Ser |
| 3916029 | | A/G | | | | | | | | | | | | | | ACG/GAG | 120 | 3 | Glu/Glu |
| 3916049 | | | | | | | | A/G | A/G | | | | A/G | A/G | | GAC/GGC | 127 | 2 | Asp/Gly |
| 3916057 | | T/C | | | | | | | | | | | | | | TGT/CGT | 130 | 1 | Cys/Arg |
| 3916084 | | | | | | | | T/C | T/C | | | | | | | TTC/CTC | 139 | 1 | Phe/Leu |
| 3916092 | | | | | | | | A/G | A/G | T/C | T/C | | | | | CTT/CTC | 141 | 3 | Leu/Leu |
| 3916093 | | | | | | | | A/G | A/G | | | | | | | AGG/GGG | 142 | 1 | Arg/Gly |
| 3916101 | | | | | | | | A/G | A/G | | | | | | | GGA/GGG | 144 | 3 | Gly/Gly |

FIGURE 4 (cont.)
PRIMATE MUTATIONS IN OAS1

| Position of first base in mutation in Reference Genbank accession NT_009775.15 | Ateles geoffroyi (ageoffr01) | Gorilla gorilla (ggogo01) | Lagothrix lagotricha (llagotr01) | Macaca arctoides (marcto01) | Macaca fascicularis (mfascic01) | Macaca mulatta (mmulatt01) | Macaca nemestrina (mnemesti01) | Pongo pygmaeus abelii (ppabeli01) | Pongo pygmaeus abelii (ppabeli02) | Pan paniscus (ppanisc01) | Pan paniscus (ppanisc02) | Pan troglodytes (ptrogl001) | Pan troglodytes verus (ptverus01) | Pan troglodytes verus (ptverus02) | Saguinus labiatus (slabiat01) | Codon Alt(s)/Ref | Amino Acid Position | Codon Position | Amino Acids Variants (Alternates/Ref) |
|---|---|---|---|---|---|---|---|---|---|---|---|---|---|---|---|---|---|---|---|
| 3918374 | | | | | | | | | | T/C | T/C | A/G | A/G | A/G | | ATT/ACT | 160 | 2 | Ile/Thr |
| 3918377 | | A/G | | | | | | | | G/A | G/A | G/A | G/A | G/A | | GAC/GGC | 161 | 2 | Asp/Gly |
| 3918391 | | T/G | | | | | | | | T/C | T/C | | | | | GAC/AAC | 166 | 1 | Asp/Asn |
| 3918417 | | | | | | | | | | | | | | | | ATT/ATC | 174 | 3 | Ile/Ile |
| 3918418 | | | | | | | | | | T/G | T/G | T/G | T/G | T/G | | AAG/GAG | 175 | 1 | Lys/Glu |
| 3918430 | | | | | | | | | | | | | | | | TAC/GAC | 179 | 1 | Tyr/Asp |
| 3918493 | | | | | | | | | | G/C | G/C | | | | | GAG/CAG | 200 | 1 | Glu/Gln |
| 3923844 | CCA/-- | | | | | | | | | | | | | | | CCACTG/CTG | 226 | 1 | ProLeu/Leu |
| 3923846 | | | | | | | | A/G | | | | | | | | CTA/CTG | 226 | 3 | Leu/Leu |
| 3923876 | A/G | | | | | | | A/C | | | | | | | | ACA/ACG | 236 | 3 | Thr/Thr |
| 3923892 | A/G | A/G | | | | | | | | | | | | | | AGA/CGA | 242 | 1 | Arg/Arg |
| 3923893 | | | | | | | | | | | | A/G | A/G | A/G | | CAA/CGA | 242 | 2 | Gln/Arg |
| 3923904 | | | | | | | | | | | | G/A | G/A | G/A | | GAA/AAA | 246 | 1 | Glu/Lys |
| 3923910 | G/C | | | | | | | | | | | G/C | G/C | | | GAT/CAT | 248 | 1 | Asp/His |
| 3923917 | T/A | | | | | | | | | | | | | | | ATC/AAC | 250 | 2 | Ile/Asn |
| 3923929 | | | | | | | | | | | | A/G | A/G | A/G | | GAA/GGA | 254 | 2 | Glu/Gly |
| 3923988 | GT/AA | | | | | | | G/A | G/A | | | | | | | GTG/AAG | 274 | 1+2 | Val/Lys |
| 3924003 | | | | | | | | | | | | G/A | G/A | G/A | | GAA/AAA | 279 | 1 | Glu/Lys |
| 3924013 | G/T | | | | | | | A/G | A/G | | | | | | | AGT/ATT | 282 | 2 | Ser/Ile |
| 3924018 | | | | | | | | C/A | C/A | | | | | | | AAA/GAA | 284 | 1 | Lys/Glu |
| 3924032 | C/A | | | | | | | | | C/T | C/A | | | | | AGC/AGA | 288 | 3 | Ser/Arg |
| 3924035 | | A/G | | | | | | | | | | A/G | A/G | A/G | | AGA/AGG | 289 | 3 | Arg/Arg |
| 3924042 | | | | | | | | | | GA/AC | GA/AC | | | | | GAG/ACG | 292 | 1+2 | Glu/Thr |
| 3924043 | | G/C | | | | | | G/C | | | | | | | | AGG/ACG | 292 | 2 | Arg/Thr |
| 3924044 | GC/CG | | | | | | | | | | | | | | | AGC/ACG | 292 | 2+3 | Ser/Thr |
| 3924853 | | | | | | | | | | T/C | T/C | | | | | INTRON | | | |
| 3924882 | A/G | | | | | | | | | A/G | A/G | | | | | GCA/GCG | 302 | 3 | Ala/Ala |
| 3924917 | | | | | | | | TT/AG | TT/AG | | | | | | | ATT/AAG | 314 | 2+3 | Ile/Lys |
| 3924981 | | | | | | | | | | | C/G | | A/G | A/G | | TGA/TGG | 335 | 3 | Term/Trp Cys/Trp |
| 3925062 | | C/T | | | | | | C/T | C/T | | C/T | | | | | TGC/TGG | 362* | 3 | His/His |
| 3925063 | | A/G | | | | | | | | | | | | | | CAC/CAT | 363* | 1 | Lys/Glu |
| 3926703 | | | A/G | | | | | | | | | | | | | AAA/GAA | 347+ | 1 | Thr/Ala |
| 3926711 | | | | | | | | T/C | T/C | | | | | | | ACT/GCT | 349+ | 3 | Ser/Ser |
| 3926712 | G/A | G/A | G/A | G/A | G/A | G/A | G/A | G/A | G/A | G/A | G/A | | | | | AGT/AGC | 350+ | 1 | Asp/Asn |
| 3926719 | AG/CA | | AG/CA | AA/CA | AA/CA | AA/CA | AA/CA | AA/CA | AA/CA | | | | | | | GAG/ GAA/GCA | 352+ | 2+3 | Glu/Glu/Ala |

FIGURE 4 (cont.)
PRIMATE MUTATIONS IN OAS1

| Position of first base in mutation in Reference Genbank accession NT_009775.15 | Ateles geoffroyi (ageo01) | Gorilla gorilla (ggor01) | Lagothrix lagotricha (llag01) | Macaca arctoides (marc01) | Macaca fascicularis (mfasc01) | Macaca mulatta (mmul01) | Macaca nemestrina (mnem01) | Pongo pygmaeus abelii (ppabe01) | Pongo pygmaeus abelii (ppabe02) | Pan Paniscus (ppan01) | Pan paniscus (ppan02) | Pan troglodytes (ptrog01) | Pan troglodytes verus (ptverus01) | Pan troglodytes verus (ptverus02) | Saguinus labiatus (slabia01) | Codon Alt(s)/Ref | Amino Acid Position | Codon Position | Amino Acids Variants (Alternates/Ref) |
|---|---|---|---|---|---|---|---|---|---|---|---|---|---|---|---|---|---|---|---|
| 3926719 | | --/CA | | | | | | | | | | | | | | GGACGAT GA/GCAG ACGAT | 352-354+ | 2+3 | GlyArgTerm/AlaAspAsp |
| 3926723 | | | | T/A | T/A | T/A | T/A | T/C | T/C | | | | | | | GAT/GAC | 353+ | 3 | Asp/Asp |
| 3926730 | | | T/G | T/G | T/G | T/G | T/G | T/G | T/G | | | | | | | TCC/ACC | 356+ | 1 | Ser/Thr |
| 3926733 | | | T/G | T/G | T/G | T/G | T/G | T/G | T/G | | | | | | | TAC/GAC | 357+ | 1 | Tyr/Asp |
| 3926746 | | | | | | | | T/G | T/G | | | | | | | ATG/AGG | 361+ | 2 | Met/Arg |
| 3926752 | | | | C/A | C/A | C/A | C/A | CA/AG | CA/AG | | | | | | | CCA/CAG | 363+ | 2+3 | Pro/Gln |
| 3926754 | | | | C/A | C/A | C/A | C/A | C/A | C/A | | | | | | | CAA/AAA | 364+ | 1 | Gln/Lys |
| 3926757 | | | | C/T | C/T | C/T | C/T | C/T | C/T | | | | | | | CAT/TAT | 365+ | 1 | His/Tyr |
| 3926768 | | | CAG/TGG | CCA/TGG | CCA/TGG | CCA/TGG | CCA/TGG | CAG/TGG | CAG/TGG | | | | | | | ATCCAA/ATCAGA/ATTGGA | 368-369+ | 3+1+2 | IleGln/IleArg/IleGly |
| 3926775 | | | T/C | T/C | T/C | T/C | T/C | | | | | | | | | TAT/CAT | 371+ | 1 | Tyr/His |
| 3926782 | | | | G/A | G/A | G/A | G/A | | | | | | | | | TGC/TAC | 373+ | 2 | Cys/Tyr |
| 3926784 | | | | T/C | T/C | T/C | T/C | T/C | | | | | | | | TCT/CCT | 374+ | 1 | Ser/Pro |
| 3926787 | | | | T/C | A/T | T/C | T/C | | | | | | | | | TAT/CAT | 375+ | 1 | Tyr/His |
| 3926798 | | | | C/A | C/A | C/A | C/A | C/A | C/A | | | | | | | CAA/CAT | 378+ | 3 | Gln/His |
| 3926801 | | | | C/A | C/A | C/A | C/A | C/A | C/A | | | | | | | AGC/AGA | 379+ | 3 | Ser/Arg |
| 3926809 | | | | | | | | | | | | | | | | CCC/ACC | 347^ | 1 | Pro/Thr |
| 3926826 | | | | | | | | | | | | | | | | ATA/ACA | 382+ | 2 | Ile/Thr |
| 3926828 | | | | | | | | | | G/A | G/A | | | | | GCC/ACC | 383+ | 1 | Ala/Thr |
| 3926830 | | | | T/C | | | T/C | | | | | | | | | ACT/ACC | 388+ | 3 | Thr/Thr |
| 3926844 | | | | GA/CA | GA/CA | GG/CA | GA/CA | | | | | | | | | CGA/CGG/CCA | 389+ | 2+3 | Arg/Arg/Pro |
| 3926844 | | | | A/G | A/G | A/G | A/G | A/G | A/G | | | | | | | AAC/GAC | 394+ | 1 | Asn/Asp |
| 3926852 | | | | A/G | A/G | A/G | A/G | A/G | A/G | | | | | | | GAA/GGA | 361^ | 2 | Glu/Gly |
| 3926852 | | | | A/C | A/C | A/C | A/C | G/C | G/C | | | | | | | ACA/ACC/ACG | 396+ | 3 | Thr/Thr/Thr |
| 3926878 | | | | A/C | A/C | A/C | A/C | G/C | G/C | | | | | | | GTG/CTG | 364^ | 1 | Val/Leu |
| 3926914 | | | | | | | | C/A | C/A | | | | | | | GCC/GCA | 372^ | 3 | Ala/Ala |
| 3926914 | | | | | | | | C/G | C/G | | | | | | | CAC/CAG | 384^ | 3 | His/Gln |
| 3926919 | | | | | | | | C/T | C/T | | | | | | | CTC/TTC | 385^ | 1 | Leu/Phe |
| 3926959 | | | | | | | | G/C | G/C | | | | | | | AGG/AGC | 399^ | 3 | Arg/Ser |

Amino acid positions are with reference to all isoforms of OAS1 (for example, SEQ ID NO:1-4 and Genbank accessions NP_002525.1 and NP_058132.1) except where * indicates position relative to NP_002525.1 homologous forms only,
+ indicates position relative to NP_058132.1 homologous forms only, and ^ indicates position relative to NP_001027581.1 homologous forms only.

FIGURE 5
ADDITIONAL OAS1 ISOFORMS OF THE INVENTION

SEQ ID NO:2 (Human OAS1 Isoform E18/p46 from NT_009775.15 Chrom 12q24.1 with nucleotide endpoints 3914354,3926867)

```
  1  MMDLRNTPAKSLDKFIEDYLLPDTCFRMQINHAIDIICGFLKERCFRGSSYPVCVSKVVK
 61  GGSSGKGTTLRGRSDADLVVFLSPLTTFQDQLNRRGEFIQEIRRQLEACQRERAFSVKFE
121  VQAPRWGNPRALSFVLSSLQLGEGVEFDVLPAFDALGQLTGGYKPNPQIYVKLIEECTDL
181  QKEGEFSTCFTELQRDFLKQRPTKLKSLIRLVKHWYQNCKKKLGKLPPQYALELLTVYAW
241  ERGSMKTHFNTAQGFRTVLELVINYQQLCIYWTKYYDFKNPIIEKYLRRQLTKPRPVILD
301  PADPTGNLGGGDPKGWRQLAQEAEAWLNYPCFKNWDGSPVSSWILLAESNSADDETDDPR
361  RYQKYGYIGTHEYPHFSHRPSTLQAASTPQAEEDWTCTIL
```

SEQ ID NO:3 (Human OAS1 Isoform E16/p40 from NT_009775.15 Chrom 12q24.1 with nucleotide endpoints 3914354,3925071)

```
  1  MMDLRNTPAKSLDKFIEDYLLPDTCFRMQINHAIDIICGFLKERCFRGSSYPVCVSKVVK
 61  GGSSGKGTTLRGRSDADLVVFLSPLTTFQDQLNRRGEFIQEIRRQLEACQRERAFSVKFE
121  VQAPRWGNPRALSFVLSSLQLGEGVEFDVLPAFDALGQLTGGYKPNPQIYVKLIEECTDL
181  QKEGEFSTCFTELQRDFLKQRPTKLKSLIRLVKHWYQNCKKKLGKLPPQYALELLTVYAW
241  ERGSMKTHFNTAQGFRTVLELVINYQQLCIYWTKYYDFKNPIIEKYLRRQLTKPRPVILD
301  PADPTGNLGGGDPKGWRQLAQEAEAWLNYPCFKNWDGSPVSSWILLVRPPASSLPFIPAP
361  LHEA
```

SEQ ID NO:4 (Human OAS1 Isoform p48 from NT_009775.15 Chrom 12q24.1 with nucleotide endpoints 3914354,3927007)

```
  1  MMDLRNTPAKSLDKFIEDYLLPDTCFRMQINHAIDIICGFLKERCFRGSSYPVCVSKVVK
 61  GGSSGKGTTLRGRSDADLVVFLSPLTTFQDQLNRRGEFIQEIRRQLEACQRERAFSVKFE
121  VQAPRWGNPRALSFVLSSLQLGEGVEFDVLPAFDALGQLTGGYKPNPQIYVKLIEECTDL
181  QKEGEFSTCFTELQRDFLKQRPTKLKSLIRLVKHWYQNCKKKLGKLPPQYALELLTVYAW
241  ERGSMKTHFNTAQGFRTVLELVINYQQLCIYWTKYYDFKNPIIEKYLRRQLTKPRPVILD
301  PADPTGNLGGGDPKGWRQLAQEAEAWLNYPCFKNWDGSPVSSWILLTQHTPGSIHPTGRR
361  GLDLHHPLNASASWGKGLQCYLDQFLHFQVGLLIQRGQSSSVSWCIIQDRTQVS
```

FIGURE 5 (cont.)

SEQ ID NO:5 (Gorilla gorilla OAS1 Isoform E18 homolog)
```
  1  MMDLRNTPAKSLDKFIEDYLLPDTCFRMQINHAIDIICGFLKERCFRGSSYPVCVSKVVK
 61  GGSSGKGTALRGRSDADLVVFLSPLTTFQDQLNRRGEFIQEIRRQLEACQRERAFSVKFE
121  VQAPRWGNPCALSFVLSSLQLGEGVEFDVLPAFDALGQLTGGYKPNPQIYVKLIKECTYL
181  QKEGEFSTCFTELQRDFLKQRPTKLKSLIRLVKHWYQNCKKKLGKLPPQYALELLTVYAW
241  EQGSMKTHFNTAQGFRTVLELVINYQQLCIYWTKYYDFKNPIIEKYLRRQLRKPRPVILD
301  PADPTGNLGGGDPKGWRQLAQEAEAWLNYPCFKNWDGSPVSSWILLAESDSGR
```

SEQ ID NO:6 (Gorilla gorilla OAS1 Isoform E16 homolog)
```
  1  MMDLRNTPAKSLDKFIEDYLLPDTCFRMQINHAIDIICGFLKERCFRGSSYPVCVSKVVK
 61  GGSSGKGTALRGRSDADLVVFLSPLTTFQDQLNRRGEFIQEIRRQLEACQRERAFSVKFE
121  VQAPRWGNPCALSFVLSSLQLGEGVEFDVLPAFDALGQLTGGYKPNPQIYVKLIKECTYL
181  QKEGEFSTCFTELQRDFLKQRPTKLKSLIRLVKHWYQNCKKKLGKLPPQYALELLTVYAW
241  EQGSMKTHFNTAQGFRTVLELVINYQQLCIYWTKYYDFKNPIIEKYLRRQLRKPRPVILD
301  PADPTGNLGGGDPKGWRQLAQEAEAWLNYPCFKNWDGSPVSSWILLVRPPASSLPFIPAP
361  LHKA
```

SEQ ID NO:7 (Gorilla gorilla OAS1 Isoform p48 homolog)
```
  1  MMDLRNTPAKSLDKFIEDYLLPDTCFRMQINHAIDIICGFLKERCFRGSSYPVCVSKVVK
 61  GGSSGKGTALRGRSDADLVVFLSPLTTFQDQLNRRGEFIQEIRRQLEACQRERAFSVKFE
121  VQAPRWGNPCALSFVLSSLQLGEGVEFDVLPAFDALGQLTGGYKPNPQIYVKLIKECTYL
181  QKEGEFSTCFTELQRDFLKQRPTKLKSLIRLVKHWYQNCKKKLGKLPPQYALELLTVYAW
241  EQGSMKTHFNTAQGFRTVLELVINYQQLCIYWTKYYDFKNPIIEKYLRRQLKKPRPVILD
301  PADPTGNLGGGDPKGWRQLAQEAEAWLNYPCFKNWDGSPVSSWILLTQHTPGSIHPTGRR
361  GLDLHHPLNASASWGKGLQCYLDQFLHFQVGLLIQRGQSSSVSWCIIQDRTQVS
```

SEQ ID NO:8 (Pan paniscus OAS1 Isoform E18 homolog)
```
  1  MMDLRNTPAKSLDKFIEDYLLPDTCFRTQINHAIDIICGFLKERCFRGSSYPVCVSKVVK
 61  GGSSGKGTTLRGRSDADLVVFLSPLTTFQDQLNRRGEFIQEIRRQLEVCQREERAFSVKF
121  EVQAPRWDNPRALSFVLSSLQLGEGVEFDVLPAFDALGQLIGGYKPDPQIYVKLIEECTY
181  LQKEGEFSTCFTELQRDFLKERPTKLKSLIRLVKHWYQNCKKKLGKLPPQYALELLTVYA
```

FIGURE 5 (cont.)

241 WERGSMKTHFNTAQGFRTVLELVINYQQLCIYWTKYYDFKNPIIEKYLSRQLEKPRPVIL

301 DPADPTGNLGGGDPKGWRQLAQEAEAWLNYPCFKNXDGSPVSSWILLAESDSADDETDDP

361 RRYQKYGYIGTHEYPHFSHRPSTLQAASAPQAEEDWTCTIL

SEQ ID NO:9 (Pan paniscus OAS1 Isoform E16 homolog)
1 MMDLRNTPAKSLDKFIEDYLLPDTCFRTQINHAIDIICGFLKERCFRGSSYPVCVSKVVK

61 GGSSGKGTTLRGRSDADLVVFLSPLTTFQDQLNRRGEFIQEIRRQLEVCQREERAFSVKF

121 EVQAPRWDNPRALSFVLSSLQLGEGVEFDVLPAFDALGQLIGGYKPDPQIYVKLIEECTY

181 LQKEGEFSTCFTELQRDFLKERPTKLKSLIRLVKHWYQNCKKKLGKLPPQYALELLTVYA

241 WERGSMKTHFNTAQGFRTVLELVINYQQLCIYWTKYYDFKNPIIEKYLSRQLEKPRPVIL

301 DPADPTGNLGGGDPKGWRQLAQEAEAWLNYPCFKNXDGSPVSSWILLVRPPASSLPFIPA

361 PLHEA

SEQ ID NO:10 (Pan paniscus OAS1 Isoform p48 homolog)
1 MMDLRNTPAKSLDKFIEDYLLPDTCFRKQINHAIDIICGFLKERCFRGSSYPVCVSKVVK

61 GGSSGKGTTLRGRSDADLVVFLSPLTTFQDQLNRRGEFIQEIRRQLEVCQREERAFSVKF

121 EVQAPRWDNPRALSFVLSSLQLGEGVEFDVLPAFDALGQLIGGYKPDPQIYVKLIEECTY

181 LQKEGEFSTCFTELQRDFLKERPTKLKSLIRLVKHWYQNCKKKLGKLPPQYALELLTVYA

241 WERGSMKTHFNTAQGFRTVLELVINYQQLCIYWTKYYDFKNPIIEKYLSRQLEKPRPVIL

301 DPADPTGNLGGGDPKGWRQLAQEAEAWLNYPCFKNXDGSPVSSWILLTQHTPGSIRPTGR

361 RGLDLHHPLNASASWGKGLQCYLDQFLHFQVGLLIQRGQSSSVSWCIIQDRTQVS

SEQ ID NO:11 (Pan troglodytes verus OAS1 homolog)
1 MMDLRNTPAKSLDKFIEDYLLPDKCFRKQINHAIDIICGFLKERCFQGSSYPVHVSKVVK

61 GGSSGKGTTLRGRSDADLVVFLSPLTTFQDQLNRRGEFIQEIRRQLEACQREERAFSVKF

121 EVQAPRWDNPRALSFVLSSLQLGEGVEFDVLPAFDALGQLTDGYKPDPQIYVKLIEECTY

181 LQKEGEFSTCFTELQRDFLKQRPTKLKSLIRLVKHWYQNCKKKLGKLPPQYALELLTVYA

241 WEQGSMETDFNTAQEFRTVLELVINYQQLCIYWTKYYDFENPIIEKYLRRQLTKPRPVIL

301 DPADPTGNLGGGDPKGWRQLAQEAEAWLNYPCFKN

SEQ ID NO:12 (Pan troglodytes OAS1 homolog)
1 MMDLRNTPAKSLDKFIEDYLLPDKCFRKQINHAIDIICGFLKERCFQGSSYPVHVSKVVK

61 GGSSGKGTTLRGRSDADLVVFLSPLTTFQDQLNRRGEFIQEIRRQLEACQREERAFXVKF

FIGURE 5 (cont.)

```
121    EVQAPRWDNPRALSFVLSSLQLGEGVEFDVLPAFDALGQLTDGYKPDPQIYVKLIEECTY

181    LQKEGEFSTCFTELQRDFLKQRPTKLKSLIRLVKHWYQNCKKKLGKLPPQYALELLTVYA

241    WEQGSMETDFNTAQEFRTVLELVINYQQLCIYWTKYYDFENPIIEKYLRRQLTKPRPVIL

301    DPADPTGNLGGGDPKGWRQLAQEAEAWLNYPCFKN
```

SEQ ID NO:13 (Pongo pygmaeus abelii OAS1 Short Isoform)
```
  1    MMDLRNTPAKSLDKFIEDYLLPDTHFRMQINHAIDTICGFLKERCFRGSSYPARVSKVVK

61    GGSSGKGTALRGRSDADLVVFLSPLTTFQDQLNRRGEFIQEIRKQLEACQRESIFREV
```

SEQ ID NO:14 (Pongo pygmaeus abelii OAS1 Isoform E18 homolog)
```
  1    MMDLRNTPAKSLDKFIEDYLLPDTHFRMQINHAIDTICGFLKERCFRGSSYPVHVSKVVK

61    GGSSGKGTALRGRSDADLVVFLSPLTTFQDQLNRRGEFIQEIRKQLEACQREXXFXXXXE

121    VQAPRWDNPRALSFVLSSFQLXEGVEFDVLPAFDALGQLTGGYKPDPQIYVKLIEECTDL

181    QKEGEFSTCFTELQRDFLKQRPTKLKSLIRLVKHWYQNCKKKLGKLPPQYALELLTVYAW

241    ERGSMKTHFNTAQGFRTVLELVINYQQLCIYWTKYYDFKNPIIKKYLSRQLRKPRPVILD

301    PADPTGNLGGGDPIGWRQLAQEAEAWLNYPCFKNWDGSPVSSWILLAESDSEDDETYDPR

361    MYXKYGYIRTHEYSHFSHSPSTLQAASTPQAEENWTCTIL
```

SEQ ID NO:15 (Pongo pygmaeus abelii OAS1 Isoform E16 homolog)
```
  1    MMDLRNTPAKSLDKFIEDYLLPDTHFRMQINHAIDTICGFLKERCFRGSSYPVHVSKVVK

61    GGSSGKGTALRGRSDADLVVFLSPLTTFQDQLNRRGEFIQEIRKQLEACQREXXFXXXXE

121    VQAPRWDNPRALSFVLSSFQLXEGVEFDVLPAFDALGQLTGGYKPDPQIYVKLIEECTDL

181    QKEGEFSTCFTELQRDFLKQRPTKLKSLIRLVKHWYQNCKKKLGKLPPQYALELLTVYAW

241    ERGSMKTHFNTAQGFRTVLELVINYQQLCIYWTKYYDFENPIIKKYLSRQLRKPRPVILD

301    PADPTGNLGGGDPIGWRQLAQEAEAWLNYPCFKNWDGSPVSSWILLVRPPASSLPFIPAP

361    LHEA
```

SEQ ID NO:16 (Pongo pygmaeus abelii OAS1 Isoform p48 homolog)
```
  1    MMDLRNTPAKSLDKFIEDYLLPDTHFRMQINHAIDTICGFLKERCFRGSSYPVHVSKVVK

61    GGSSGKGTALRGRSDADLVVFLSPLTTFQDQLNRRGEFIQEIRKQLEACQREXXFXXXXE

121    VQAPRWDNPRALSFVLSSFQLXEGVEFDVLPAFDALGQLTGGYKPDPQIYVKLIEECTDL

181    QKEGEFSTCFTELQRDFLKQRPTKLKSLIRLVKHWYQNCKKKLGKLPPQYALELLTVYAW

241    ERGSMKTHFNTAQGFRTVLELVINYQQLCIYWTKYYDFENPIIKKYLSRQLKKPRPVILD

301    PADPTGNLGGGDPIGWRQLAQEAEAWLNYPCFKNWDGSPVSSWILLPQHTPGSIHPTGRR
```

FIGURE 5 (cont.)

361 ELDVHHPLNASASWGKGLQCYLDHLLHFQVGLLIQRGQRSSVSWCIIQDRTQVS

In the foregoing sequences, X indicates a variant amino acid as described by the following table.

| Sequence | Amino Acid Position | Alternate Amino Acids |
|---|---|---|
| SEQ ID NO:8 | 336 | W or C |
| SEQ ID NO:9 | 336 | W or C |
| SEQ ID NO:10 | 336 | W or C |
| SEQ ID NO:12 | 117 | S or A |
| SEQ ID NO:14 | 113 | S or R |
| SEQ ID NO:15 | 113 | S or R |
| SEQ ID NO:16 | 113 | S or R |
| SEQ ID NO:14 | 114 | I or A |
| SEQ ID NO:15 | 114 | I or A |
| SEQ ID NO:16 | 114 | I or A |
| SEQ ID NO:14 | 116 | R or S |
| SEQ ID NO:15 | 116 | R or S |
| SEQ ID NO:16 | 116 | R or S |
| SEQ ID NO:14 | 117 | E or V |
| SEQ ID NO:15 | 117 | E or V |
| SEQ ID NO:16 | 117 | E or V |
| SEQ ID NO:14 | 118 | V or K |
| SEQ ID NO:15 | 118 | V or K |
| SEQ ID NO:16 | 118 | V or K |
| SEQ ID NO:14 | 119 | Term or F |
| SEQ ID NO:15 | 119 | Term or F |
| SEQ ID NO:16 | 119 | Term or F |
| SEQ ID NO:14 | 142 | R or G |
| SEQ ID NO:15 | 142 | R or G |
| SEQ ID NO:16 | 142 | R or G |
| SEQ ID NO:14 | 363 | P or Q |

MUTATIONS IN OAS1 GENES

RELATED APPLICATIONS

The present application is a continuation of U.S. patent application Ser. No. 12/248,810 filed Oct. 9, 2008, which claims the benefit of priority from U.S. patent application Ser. No. 11/416,790 filed May 3, 2006, which claims benefit from U.S. Provisional Patent Application titled MUTATIONS IN OAS1 GENES Ser. No. 60/677,680 filed May 4, 2005 under 35 U.S.C. §119. The foregoing patent applications are incorporated herein by reference in their entirety.

TECHNICAL FIELD

The present invention relates to a method for detecting a mutation in a human or non-human primate oligoadenylate synthetase gene, and to OAS1 proteins having at least one amino acid modification.

BACKGROUND OF THE INVENTION

A number of diseases have been identified to date in which natural resistance to infection exists in the human population. Alter and Moyer, *J. Acquir. Immune Defic. Syndr. Hum Retrovirol.* 18 Suppl. 1:S6-10 (1998) report hepatitis C viral infection (HCV) rates as high as 90% in high-risk groups such as injecting drug users. However, the mechanism by which the remaining 10% are apparently resistant to infection has not been identified in the literature. Proteins that play a role in HCV infection include the 2-prime, 5-prime oligoadenylate synthetases. OASs are interferon-induced proteins characterized by their capacity to catalyze the synthesis of 2-prime,5-prime oligomers of adenosine (2-5As). Hovanessian et al., *EMBO* 6: 1273-1280 (1987) found that interferon-treated human cells contain several OASs corresponding to proteins of 40 (OAS1), 46 (OAS1), 69, and 100 kD. Marie et al., *Biochem. Biophys. Res. Commun.* 160:580-587 (1989) generated highly specific polyclonal antibodies against p69, the 69-kD OAS. By screening an interferon-treated human cell expression library with the anti-p69 antibodies, Marie and Hovanessian, *J. Biol. Chem.* 267: 9933-9939 (1992) isolated a partial OAS2 cDNA. They screened additional libraries with the partial cDNA and recovered cDNAs encoding two OAS2 isoforms. The smaller isoform is encoded by two mRNAs that differ in the length of the 3-prime untranslated region.

Northern blot analysis revealed that OAS2 is expressed as four interferon-induced mRNAs in human cells. The predicted OAS2 proteins have a common 683-amino acid sequence and different 3-prime termini. According to SDS-PAGE of in vitro transcription/translation products, two isoforms have molecular masses of 69 and 71 kD. Both isoforms exhibited OAS activity in vitro. Sequence analysis indicated that OAS2 contains two OAS1-homologous domains separated by a proline-rich putative linker region. The N- and C-terminal domains are 41% and 53% identical to OAS1, respectively.

By fluorescence in situ hybridization and by inclusion within mapped clones, Hovanian et al., *Genomics* 52: 267-277 (1998) determined that the OAS1, OAS2, and OAS3 genes are clustered with a 130-kb region on 12q24.2. 2-5As bind to and activate RNase I, which degrades viral and cellular RNAs, leading to inhibition of cellular protein synthesis and impairment of viral replication.

A fourth human OAS gene, referred to as OASL, differs from OAS1, OAS2 and OAS3 in that OASL lacks enzyme activity. The OASL gene encodes a two-domain protein composed of an OAS unit fused to a 164 amino acid C-terminal domain that is homologous to a tandem repeat of ubiquitin. (Eskildsen et al., Nuc. Acids Res. 31:3166-3173, 2003; Kakuta et al., J. Interferon & Cytokine Res. 22:981-993, 2002.)

Because of their role in inhibiting viral replication and viral infection, there is a need in the art for methods and compositions that suppress viral replication related to OAS1 activity, including a profound need for inhibitor-based therapies that suppress HCV replication.

BRIEF SUMMARY OF THE INVENTION

The present invention relates to detecting hepatitis C resistance-related mutations which may be characterized as mutations in the oligoadenylate synthetase 1 gene.

In one embodiment, a genetic screening method is contemplated. The method comprises assaying a nucleic acid sample isolated from a human or non-human primate for the presence of an oligoadenylate synthetase 1 gene mutation causing an amino acid modification at one or more of positions 1, 24, 25, 28, 31, 36, 47, 53, 54, 64, 69, 74, 104, 108, 112, 113, 114, 115, 116, 117, 118, 119, 127, 130, 139, 142, 160, 161, 162, 166, 175, 179, 226, 242, 246, 248, 250, 254, 274, 279, 282, 284, 288, 289, 292, 295, 314, 315, and 335 for all oligoadenylate synthetase 1 (OAS1) forms (including without limitation SEQ ID NO:1).

In a further embodiment, a genetic screening method is contemplated. The method comprises assaying a nucleic acid sample isolated from a human or non-human primate for the presence of an oligoadenylate synthetase 1 gene mutation causing an amino acid modification at position 363 for all oligoadenylate synthetase 1 forms that are carboxyl-terminus homologous to Genbank accession NP_002525.1 (including without limitation SEQ ID NO:3).

In a yet further embodiment, a genetic screening method is contemplated. The method comprises assaying a nucleic acid sample isolated from a human or non-human primate for the presence of an oligoadenylate synthetase 1 gene mutation causing an amino acid modification at one or more of amino acid positions 347, 350, 352, 353, 354, 356, 357, 361, 363, 364, 365, 369, 371, 373, 374, 375, 378, 379, 382, 388, 389, or 394 for all oligoadenylate synthetase 1 forms that are carboxyl-terminus homologous to Genbank accession NP_058132.1 (including without limitation SEQ ID NO:2).

In a yet further embodiment, a genetic screening method is contemplated. The method comprises assaying a nucleic acid sample isolated from a human or non-human primate for the presence of an oligoadenylate synthetase 1 gene mutation causing an amino acid modification at one or more of amino acid positions 347, 361, 364, 372, 384, 385, or 399 for all oligoadenylate synthetase 1 forms that are carboxyl-terminus homologous to Genbank accession NP_001027581.1 (including without limitation SEQ ID NO:4).

In a further embodiment, the invention provides a protein having at least one amino acid modification at positions 1, 24, 25, 28, 31, 36, 47, 53, 54, 64, 69, 74, 104, 108, 112, 113, 114, 115, 116, 117, 118, 119, 127, 130, 139, 142, 160, 161, 162, 166, 175, 179, 226, 242, 246, 248, 250, 254, 274, 279, 282, 284, 288, 289, 292, 295, 314, 315, and 335 for all oligoadenylate synthetase 1 (OAS1) forms (including without limitation SEQ ID NO:1), and use of the protein to prepare a diagnostic for resistance to viral infection, preferably flaviviral infection, most preferably hepatitis C infection. In specific embodiments, the diagnostic is an antibody.

In a further embodiment, the invention provides a OAS1 protein having an amino acid modification at position 363 for all oligoadenylate synthetase 1 forms that are carboxyl-terminus homologous to Genbank accession NP_002525.1 (including without limitation SEQ ID NO:3), and use of the protein to prepare a diagnostic for resistance to viral infection, preferably flaviviral infection, most preferably hepatitis C infection. In specific embodiments, the diagnostic is an antibody.

In a further embodiment, the invention provides a OAS1 protein having at least one amino acid modification at positions 347, 350, 352, 353, 354, 356, 357, 361, 363, 364, 365, 369, 371, 373, 374, 375, 378, 379, 382, 388, 389, and 394 for all oligoadenylate synthetase 1 forms that are carboxyl-terminus homologous to Genbank accession NP_058132.1 (including without limitation SEQ ID NO:2) and use of the protein to prepare a diagnostic for resistance to viral infection, preferably flaviviral infection, most preferably hepatitis C infection. In specific embodiments, the diagnostic is an antibody.

In a yet further embodiment, the invention provides a OAS1 protein having at least one amino acid modification at positions 347, 361, 364, 372, 384, 385, or 399 for all oligoadenylate synthetase 1 forms that are carboxyl-terminus homologous to Genbank accession NP_001027581.1 (including without limitation SEQ ID NO: 4) and use of the protein to prepare a diagnostic for resistance to viral infection, preferably flaviviral infection, most preferably hepatitis C infection. In specific embodiments, the diagnostic is an antibody.

In a still further embodiment, the invention provides a therapeutic compound for preventing or inhibiting infection by a virus, preferably a flavivirus, most preferably hepatitis C virus, wherein the therapeutic compound is a protein having at least one amino acid modification according to the invention. In other embodiments the therapeutic compound is a polynucleotide, such as DNA or RNA, encoding the protein.

In a still further embodiment, the invention provides a therapeutic compound for preventing or inhibiting infection by a virus, preferably a flavivirus, most preferably a hepatitis C virus, wherein the therapeutic compound is a protein encoded by OAS1 of the invention having one or more of the disclosed amino acid modifications.

In a still further embodiment, the invention provides a therapeutic compound for preventing or inhibiting infection by a virus, preferably a flavivirus, most preferably hepatitis C virus, wherein the therapeutic compound mimics the beneficial effects of at least one mutation of the invention. The therapeutic compound can be a small molecule, protein, peptide, DNA or RNA molecule, or antibody.

In a still further embodiment, the invention provides a therapeutic compound for preventing or treating cancer, preferably prostate cancer, wherein the therapeutic compound is a protein encoded by an OAS1 gene having at least one mutation of the invention. In other embodiments the therapeutic compound is a polynucleotide, such as DNA or RNA, encoding the protein.

In a still further embodiment, the invention provides a therapeutic compound for preventing or treating cancer, preferably prostate cancer, wherein the therapeutic compound is a OAS1 protein having at least one amino acid modification of the invention:

In a still further embodiment, the invention provides a therapeutic compound for preventing or treating cancer, preferably prostate cancer, wherein the therapeutic compound mimics the beneficial effects of at least one mutation of the invention. The therapeutic compound can be a small molecule, protein, peptide, DNA or RNA molecule, or antibody.

In further embodiments, the therapeutic compound is capable of inhibiting the activity of OAS1 or at least one sub-region or sub-function of the entire protein, and such compounds are represented by antisense molecules, ribozymes, and RNAi molecules capable of specifically binding to OAS1 polynucleotides, and by antibodies and fragments thereof capable of specifically binding to OAS1 proteins and polypeptides.

The present invention provides, in another embodiment, inhibitors of OAS1. Inventive inhibitors include, but are not limited to, antisense molecules, ribozymes, RNAi, antibodies or antibody fragments, proteins or polypeptides as well as small molecules. Exemplary antisense molecules comprise at least 10, 15 or 20 consecutive nucleotides of, or that hybridize under stringent conditions to the polynucleotide encoding OAS1 having at least one amino acid modification of the invention.

In a still further embodiment, inhibitors of OAS1 are envisioned that specifically bind to the region of the protein defined by a OAS1 polypeptide having an amino acid modification of the invention. Inventive inhibitors include but are not limited to, antibodies, antibody fragments, small molecules, proteins, or polypeptides.

In a still further embodiment, inhibitors of OAS1 are envisioned that are comprised of antisense or RNAi molecules that specifically bind or hybridize to a polynucleotide encoding an OAS1 protein having at least one amino acid modification of the invention.

In further embodiments, compositions are provided that comprise one or more OAS1 inhibitors in a pharmaceutically acceptable carrier.

Additional embodiments provide methods of decreasing OAS1 gene expression or biological activity.

Additional embodiments provide for methods of specifically increasing or decreasing the expression of certain forms of the OAS1 gene having at least one mutation as disclosed by the invention.

The invention provides an antisense oligonucleotide comprising at least one modified internucleoside linkage.

The invention further provides an antisense oligonucleotide having a phosphorothioate linkage.

The invention still further provides an antisense oligonucleotide comprising at least one modified sugar moiety.

The invention also provides an antisense oligonucleotide comprising at least one modified sugar moiety which is a 2'-O-methyl sugar moiety.

The invention further provides an antisense oligonucleotide comprising at least one modified nucleobase.

The invention still further provides an antisense oligonucleotide having a modified nucleobase wherein the modified nucleobase is 5-methylcytosine.

The invention also provides an antisense compound wherein the antisense compound is a chimeric oligonucleotide.

The invention provides a method of inhibiting the expression of human OAS1 in human cells or tissues comprising contacting the cells or tissues in vivo with an antisense compound or a ribozyme of 8 to 35 nucleotides in length targeted to a nucleic acid molecule encoding human OAS1 so that expression of human OAS1 is inhibited.

The invention further provides a method of decreasing or increasing expression of specific forms of OAS1 in vivo, such forms being defined by having at least one mutation at a position according to the invention, using antisense or RNAi compounds or ribozymes.

The invention further provides a method of modulating growth of cancer cells comprising contacting the cancer cells in vivo with an antisense compound or ribozyme of 8 to 35 nucleotides in length targeted to a nucleic acid molecule encoding human OAS1 so that expression of human OAS1 is inhibited.

The invention still further provides for identifying target regions of OAS1 polynucleotides. The invention also provides labeled probes for identifying OAS1 polynucleotides by in situ hybridization.

The invention provides for the use of an OAS1 inhibitor according to the invention to prepare a medicament for preventing or inhibiting HCV infection.

The invention further provides for directing an OAS1 inhibitor to specific regions of the OAS1 protein or at specific functions of the protein.

The invention also provides a pharmaceutical composition for inhibiting expression of OAS1, comprising an antisense oligonucleotide according to the invention in a mixture with a physiologically acceptable carrier or diluent.

The invention further provides a ribozyme capable of specifically cleaving OAS1 RNA, and a pharmaceutical composition comprising the ribozyme.

The invention also provides small molecule inhibitors of OAS1 wherein the inhibitors are capable of reducing the activity of OAS1 or of reducing or preventing the expression of OAS1 mRNA.

The invention further provides for inhibitors of OAS1 that modify specific functions of the protein other than the synthesis of 2'-5' oligoadenylates, such functions including interaction with other proteins such as Hepatitis C virus NS5A protein.

The invention further provides for compounds that alter post-translational modifications of OAS1 including but not limited to glycosylation and phosphorylation.

The invention further provides a human genetic screening method for identifying an oligoadenylate synthetase gene mutation comprising: (a) treating, under amplification conditions, a sample of genomic DNA from a human with a polymerase chain reaction (PCR) primer pair for amplifying a region of human genomic DNA containing at least one mutation of an OAS1 gene according to the invention, said treating producing an amplification product containing said region; and (b) detecting in the amplification product of step (a) the presence of a nucleotide mutation at a nucleotide position of the invention, thereby identifying said mutation.

The invention also relates to a method for detecting in a human a hepatitis C infection resistance disease allele containing a mutation comprising substitution of a non wild-type nucleotide for a wild-type nucleotide at a nucleotide position corresponding to an amino acid modification of the invention in the OAS1 protein encoded by the gene of oligoadenylate synthetase gene (OAS1), which method comprises: (a) forming a polymerase chain reaction (PCR) admixture by combining, in a PCR buffer, a sample of genomic DNA from said human and an oligoadenylate synthetase gene-specific PCR primer pair; (b) subjecting the PCR admixture to a plurality of PCR thermocycles to produce an oligoadenylate synthetase gene amplification product; and (c) treating, under hybridization conditions products produced in step (b), with a probe capable of detecting said mutation.

Also provided is an isolated OAS1 inhibitor selected from the group consisting of an antisense oligonucleotide, a ribozyme, a small inhibitory RNA (RNAi), a protein, a polypeptide, an antibody, and a small molecule. The isolated inhibitor may be an antisense molecule or the complement thereof comprising at least 15 consecutive nucleic acids of a polynucleotide sequence corresponding to a OAS1 gene mutation associated with an amino acid substitution of the invention.

The isolated OAS1 inhibitor may be selected from the group consisting of an antibody and an antibody fragment. Also provided is a composition comprising a therapeutically effective amount of at least one OAS1 inhibitor in a pharmaceutically acceptable carrier.

The invention also relates to a method of inhibiting the expression of OAS1 in a mammalian cell, comprising administering to the cell an OAS1 inhibitor selected from the group consisting of an antisense oligonucleotide, a ribozyme, a protein, an RNAi, a polypeptide, an antibody, and a small molecule.

The invention further relates to a method of inhibiting the expression of OAS1 gene expression in a subject, comprising administering to the subject, in a pharmaceutically effective vehicle, an amount of an antisense oligonucleotide which is effective to specifically hybridize to all or part of a selected target nucleic acid sequence derived from said OAS1 gene.

The invention still further relates to a method of preventing infection by a flavivirus in a human subject susceptible to the infection, comprising administering to the human subject an OAS1 inhibitor selected from group consisting of an antisense oligonucleotide, a ribozyme, an RNAi, a protein, a polypeptide, an antibody, and a small molecule, wherein said OAS1 inhibitor prevents infection by said flavivirus.

BRIEF DESCRIPTION OF THE FIGURES

FIG. 1 is an amino acid sequence of a therapeutic form of OAS1 protein (SEQ ID NO:1).

FIG. 2 is a table listing amino acid substitutions useful in all therapeutic forms of OAS1.

FIG. 3 is a table listing primate OAS1 amino acid modifications useful in therapeutic forms of OAS1. Positions indicated with * refer to forms of OAS1 that are carboxyl-terminus homologous to Genbank accession NP_002525.1. Positions indicated with + refer to forms of OAS1 that are carboxyl-terminus homologous to Genbank accession NP_0581321. Positions indicated with ^ refer to forms of OAS1 that are carboxyl-terminus homologous to Genbank accession NP_001027581.1.

FIG. 4 is a chart indicating the positions of mutations of primate OAS1 genes and corresponding amino acid modifications. Position 3916008 corresponds to amino acid variant SerIlePheArgGluVal (SEQ ID NO:18) and reference amino acid sequence ArgAlaPheSerValLysPhe (SEQ ID NO:19).

FIG. 5 is a listing of additional OAS1 isoforms of the present invention, including human and non-human primate forms. Also provided are mutations of the primate isoforms. These isoforms, either alone or together with any mutations identified in the present invention, are useful for the diagnostic, therapeutic, and other purposes described herein.

DETAILED DESCRIPTION OF THE INVENTION

This invention relates to novel mutations in the oligoadenylate synthetase 1 gene, use of these mutations for diagnosis of susceptibility or resistance to viral infection, to proteins encoded by a gene having a mutation according to the invention, and to prevention or inhibition of viral infection using the proteins, antibodies, and related nucleic acids. These mutations correlate with resistance of the carrier to infection with flavivirus, particularly hepatitis C virus.

Much of current medical research is focused on identifying mutations and defects that cause or contribute to disease.

Such research is designed to lead to compounds and methods of treatment aimed at the disease state. Less attention has been paid to studying the genetic influences that allow people to remain healthy despite exposure to infectious agents and other risk factors. The present invention represents a successful application of a process developed by the inventors by which specific populations of human subjects are ascertained and analyzed in order to discover genetic variations or mutations that confer resistance to disease. The identification of a sub-population segment that has a natural resistance to a particular disease or biological condition further enables the identification of genes and proteins that are suitable targets for pharmaceutical intervention, diagnostic evaluation, or prevention, such as prophylactic vaccination.

A sub-population segment was previously identified and disclosed in co-pending application Ser. No. 10/972,135 and was comprised of individuals who, despite repeated exposure to hepatitis C virus (HCV) have nonetheless remained sero-negative, while cohorts have become infected (sero-positive). The populations studied included hemophiliac patients subjected to repeated blood transfusions, and intravenous drug users who become exposed through shared needles and other risk factors.

The present disclosure provides mutations identified in OAS1 genes of non-human primates, as described in Example 1.

Application Ser. No. 10/972,135 provides disclosure related to HCV infection; definitions; modes of practicing the invention; polynucleotide analysis; preparation of polynucleotide primers; polymerase chain reaction; nucleic acid sequence analysis; detection of membrane-immobilized target sequences; scanning techniques for detection of base substitutions; therapeutic agents for restoring and/or enhancing OAS1 function; therapeutic agents for inhibition of OAS1 function; ribozymes; RNAi; proteins and polypeptides; small molecules; methods for assessing the efficacy of OAS1 inhibitors; and pharmaceutical compositions. Application Ser. No. 10/972,135 is hereby incorporated herein by reference in its entirety.

The polypeptides of the present invention are able, as part of their native function, to transduce across a cell membrane and mediate their antiviral effects in the absence of a delivery vector or expression vehicle. The cell transduction properties of basic, positively charged proteins has been previously described and is well known to those skilled in the art (Ryser and Hancock, Science. 1965 Oct. 22; 150 (695):501-3).

In the case where the polypeptides are prepared as a liquid formulation and administered by injection, preferably the solution is an isotonic salt solution containing 140 millimolar sodium chloride and 10 millimolar calcium at pH 7.4. The injection may be administered, for example, in a therapeutically effective amount, preferably in a dose of about 1 μg/kg body weight to about 5 mg/kg body weight daily, taking into account the routes of administration, health of the patient, etc.

The polypeptide(s) of the present invention may be employed in combination with a suitable pharmaceutical carrier. Such compositions comprise a therapeutically effective amount of the protein, and a pharmaceutically acceptable carrier or excipient. Such a carrier includes but is not limited to saline, buffered saline, dextrose, water, glycerol, ethanol, and combinations thereof. The formulation should suit the mode of administration.

The polypeptide(s) of the present invention can also be modified by chemically linking the polypeptide to one or more moieties or conjugates to enhance the activity, cellular distribution, or cellular uptake of the polypeptide(s). Such moieties or conjugates include lipids such as cholesterol, cholic acid, thioether, aliphatic chains, phospholipids and their derivatives, polyamines, polyethylene glycol (PEG), palmityl moieties, and others as disclosed in, for example, U.S. Pat. Nos. 5,514,758, 5,565,552, 5,567,810, 5,574,142, 5,585,481, 5,587,371, 5,597,696 and 5,958,773.

The polypeptides of the present invention may also be modified to target specific cell types for a particular disease indication, including but not limited to liver cells in the case of hepatitis C infection. As can be appreciated by those skilled in the art, suitable methods have been described that achieve the described targeting goals and include, without limitation, liposomal targeting, receptor-mediated endocytosis, and antibody-antigen binding. In one embodiment, the asiaglycoprotein receptor may be used to target liver cells by the addition of a galactose moiety to the polypeptide(s). In another embodiment, mannose moieties may be conjugated to the polypeptide(s) in order to target the mannose receptor found on macrophages and liver cells. As one skilled in the art will recognize, multiple delivery and targeting methods may be combined. For example, the polypeptide(s) of the present invention may be targeted to liver cells by encapsulation within liposomes, such liposomes being conjugated to galactose for targeting to the asialoglycoprotein receptor.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptide of the present invention may be employed in conjunction with other therapeutic compounds.

When the polypeptide(s) of the present invention are used as a pharmaceutical, they can be given to mammals, in a suitable vehicle. When the polypeptides of the present invention are used as a pharmaceutical as described above, they are given, for example, in therapeutically effective doses of about 10 μg/kg body weight to about 10 mg/kg body weight daily, taking into account the routes of administration, health of the patient, etc. The amount given is preferably adequate to achieve prevention or inhibition of infection by a virus, preferably a flavivirus, most preferably RSV and HCV, prevention or treatment of cancer, inflammation, diabetes, or other diseases.

The proteins, their fragments or other derivatives, or analogs thereof, or cells expressing them can be used as an immunogen to produce antibodies thereto. These antibodies can be, for example, polyclonal, monoclonal, chimeric, single chain, Fab fragments, or the product of an Fab expression library. Various procedures known in the art may be used for the production of polyclonal antibodies.

Antibodies generated against the polypeptide(s) of the present invention can be obtained by direct injection of the polypeptide into an animal or by administering the polypeptide to an animal, preferably a nonhuman. The antibody so obtained will then bind the polypeptide itself. In this manner, even a sequence encoding only a fragment of the polypeptide can be used to generate antibodies binding the whole native polypeptide. Moreover, a panel of such antibodies specific to a large number of polypeptides can be used.

For preparation of monoclonal antibodies, any technique which provides antibodies produced by continuous cell line cultures can be used. Examples include the hybridoma technique (Kohler and Milstein, 1975, *Nature,* 256:495-597), the trioma technique, the human B-cell hybridoma technique (Kozbor, et al., 1983, *Immunology Today* 4:72), and the EBVhybridoma technique to produce human monoclonal antibodies (Coe, et al., 1985, *Monoclonal Antibodies and Cancer Therapy*, Alan R. Liss, Inc. pp. 77-96).

Techniques described for the production of single chain antibodies (U.S. Pat. No. 4,946,778) can be adapted to produce single chain antibodies to immunogenic polypeptide products of this invention.

The antibodies can be used in methods relating to the localization and activity of the protein sequences of the invention, e.g., for imaging these proteins, measuring levels thereof in appropriate physiological samples, and the like.

The invention provides for polypeptides that differ from the polypeptides of FIGS. 1-5 by 1 to 34 amino acids, such differences may include substitutions, insertions, deletions, the incorporation of modified amino acids or amino acid derivatives, and the addition or deletion of amino acids from the C-terminus or N-terminus of the polypeptides. The invention provides for therapeutic and prophylactic uses of these polypeptides including but not limited to the treatment of virus infection, neoplasm, cancer, diabetes, and to promote cell growth and differentiation and tissue regeneration. The invention provides for polynucleotides encoding the polypeptides of the invention and uses thereof including but not limited to uses in manufacturing the polypeptides, as gene therapies, as diagnostic tools, etc.

Pharmaceutical Compositions

The invention provides pharmaceutical compositions of the polypeptides as active ingredients for a therapeutic application. These compositions can also be used in the method of the present invention. In general the pharmaceutical composition for inhibiting virus infection, cancer, neoplasm, inflammation, or other disease in a mammal or subject includes an effective amount of at least one polypeptide as described above needed for the practice of the invention, or a fragment thereof shown to have the same effect, and a pharmaceutically physiologically acceptable carrier or diluent. According to the present invention, a pharmaceutical composition can be composed of two or more of the polypeptides of FIGS. 1-5 in combination. The pharmaceutical composition may further be composed of a single polypeptide that contains one or more of the modifications of FIGS. 1-5 within a contiguous molecule.

The compositions can be administered orally, subcutaneously, or parenterally including intravenous, intraarterial, intramuscular, intraperitoneally, and intranasal administration, as well as intrathecal and infusion techniques as required. The pharmaceutically acceptable carriers, diluents, adjuvants and vehicles as well as implant carriers generally refer to inert, non-toxic solid or liquid fillers, diluents or encapsulating material not reacting with the active ingredients of the invention. Cationic lipids may also be included in the composition to facilitate polypeptide uptake. Implants of the compounds are also useful. In general, the pharmaceutical compositions are sterile.

The present invention relates to compositions of the polypeptides to which a detectable label is attached, such as a fluorescent, chemiluminescent or radioactive molecule.

Another example is a pharmaceutical composition which may be formulated by known techniques using known materials, see, Remington's Pharmaceutical Sciences, 18th Ed. (1990, Mack Publishing Co., Easton, Pa. 18042) pp. 1435-1712, which are herein incorporated by reference. Generally, the formulation will depend on a variety of factors such as administration, stability, production concerns and other factors. The polypeptides of FIGS. 1-5 may be administered by injection or by pulmonary administration via inhalation. Enteric dosage forms may also be available, and therefore oral administration may be effective. The polypeptides of the invention may be inserted into liposomes or other microcarriers for delivery, and may be formulated in gels or other compositions for sustained release. Although preferred compositions will vary depending on the use to which the composition will be put, generally, for the polypeptides of the present invention, preferred pharmaceutical compositions are those prepared for subcutaneous injection or for pulmonary administration via inhalation, although the particular formulations for each type of administration will depend on the characteristics of the specific polypeptide.

Therapeutic formulations of the polypeptides or polypeptide conjugates of the invention are typically administered in a composition that includes one or more pharmaceutically acceptable carriers or excipients. Such pharmaceutical compositions may be prepared in a manner known per se in the art to result in a polypeptide pharmaceutical that is sufficiently storage-stable and is suitable for administration to humans or animals.

The polypeptides or polypeptide conjugates of the invention can be used "as is" and/or in a salt form thereof. Suitable salts include, but are not limited to, salts with alkali metals or alkaline earth metals, such as sodium, potassium, calcium and magnesium, as well as e.g. zinc salts. These salts or complexes may by present as a crystalline and/or amorphous structure.

"Pharmaceutically acceptable" means a carrier or excipient that at the dosages and concentrations employed does not cause any untoward effects in the patients to whom it is administered. Such pharmaceutically acceptable carriers and excipients are well known in the art (see Remington's Pharmaceutical Sciences, 18th edition, A. R. Gennaro, Ed., Mack Publishing Company (1990); Pharmaceutical Formulation Development of Peptides and Proteins, S. Frokjaer and L. Hovgaard, Eds., Taylor & Francis (2000); and Handbook of Pharmaceutical Excipients, 3rd edition, A. Kibbe, Ed., Pharmaceutical Press (2000)).

The composition of the invention may be administered alone or in conjunction with other therapeutic agents. Ribavirin and interferon alpha, for example, have been shown to be an effective treatment for HCV infection when used in combination. Their efficacy in combination exceeds the efficacy of either drug product when used alone. The compositions of the invention may be administered alone or in combination with interferon, ribavirin and/or a variety of small molecules that are being developed against both viral targets (viral proteases, viral polymerase, assembly of viral replication complexes) and host targets (host proteases required for viral processing, host kinases required for phosphorylation of viral targets such as NS5A and inhibitors of host factors required to efficiently utilize the viral IRES). Cytokines may be co-administered, such as for example IL-2, IL-12, IL-23, IL-27, or IFN-gamma. These agents may be incorporated as part of the same pharmaceutical composition or may be administered separately from the polypeptides or conjugates of the invention, either concurrently or in accordance with another treatment schedule. In addition, the polypeptides, polypeptide conjugates or compositions of the invention may be used as an adjuvant to other therapies.

A "patient" for the purposes of the present invention includes both humans and other mammals. Thus the methods are applicable to both human therapy and veterinary applications The pharmaceutical composition comprising the polypeptide or conjugate of the invention may be formulated in a variety of forms, e.g. as a liquid, gel, lyophilized, or as a compressed solid. The preferred form will depend upon the particular indication being treated and will be apparent to one skilled in the art.

The administration of the formulations of the present invention can be performed in a variety of ways, including, but not limited to, orally, subcutaneously, intravenously, intracerebrally, intranasally, transdermally, intraperitoneally, intramuscularly, intrapulmonary, intrathecally, vaginally, rectally, intraocularly, or in any other acceptable manner. The formulations can be administered continuously by infusion, although bolus injection is acceptable, using techniques well known in the art, such as pumps (e.g., subcutaneous osmotic pumps) or implantation. In some instances the formulations may be directly applied as a solution or spray.

An example of a pharmaceutical composition is a solution designed for parenteral administration. Although in many cases pharmaceutical solution formulations are provided in liquid form, appropriate for immediate use, such parenteral formulations may also be provided in frozen or in lyophilized form. In the former case, the composition must be thawed prior to use. The latter form is often used to enhance the stability of the active compound contained in the composition under a wider variety of storage conditions, as it is recognized by those skilled in the art that lyophilized preparations are generally more stable than their liquid counterparts. Such lyophilized preparations are reconstituted prior to use by the addition of one or more suitable pharmaceutically acceptable diluents such as sterile water for injection or sterile physiological saline solution.

Parenterals may be prepared for storage as lyophilized formulations or aqueous solutions by mixing, as appropriate, the polypeptide having the desired degree of purity with one or more pharmaceutically acceptable carriers, excipients or stabilizers typically employed in the art (all of which are termed "excipients"), for example buffering agents, stabilizing agents, preservatives, isotonifiers, non-ionic detergents, antioxidants and/or other miscellaneous additives.

Buffering agents help to maintain the pH in the range which approximates physiological conditions. They are typically present at a concentration ranging from about 2 mM to about 50 mM. Suitable buffering agents for use with the present invention include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additional possibilities are phosphate buffers, histidine buffers and trimethylamine salts such as Tris.

Preservatives are added to retard microbial growth, and are typically added in amounts of about 0.2%-1% (w/v). Suitable preservatives for use with the present invention include phenol, benzyl alcohol, meta-cresol, methyl paraben, propyl paraben, octadecyldimethylbenzyl ammonium chloride, benzalkonium halides (e.g. benzalkonium chloride, bromide or iodide), hexamethonium chloride, alkyl parabens such as methyl or propyl paraben, catechol, resorcinol, cyclohexanol and 3-pentanol.

Isotonicifiers are added to ensure isotonicity of liquid compositions and include polyhydric sugar alcohols, preferably trihydric or higher sugar alcohols, such as glycerin, erythritol, arabitol, xylitol, sorbitol and mannitol. Polyhydric alcohols can be present in an amount between 0.1% and 25% by weight, typically 1% to 5%, taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, omithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur-containing reducing agents, such as urea, glutathione, thioctic acid, sodium thioglycolate, thioglycerol, alpha-monothioglycerol and sodium thiosulfate; low molecular weight polypeptides (i.e. <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran. Stabilizers are typically present in the range of from 0.1 to 10,000 parts by weight based on the active protein weight.

Non-ionic surfactants or detergents (also known as "wetting agents") may be present to help solubilize the therapeutic agent as well as to protect the therapeutic polypeptide against agitation-induced aggregation, which also permits the formulation to be exposed to shear surface stress without causing denaturation of the polypeptide. Suitable non-ionic surfactants include polysorbates (20, 80, etc.), polyoxamers (184, 188 etc.), Pluronic® polyols, polyoxyethylene sorbitan monoethers (Tween®-20, Tween®-80, etc.).

Additional miscellaneous excipients include bulking agents or fillers (e.g. starch), chelating agents (e.g. EDTA), antioxidants (e.g., ascorbic acid, methionine, vitamin E) and cosolvents.

The active ingredient may also be entrapped in microcapsules prepared, for example, by coascervation techniques or by interfacial polymerization, for example hydroxymethylcellulose, gelatin or poly-(methylmethacylate) microcapsules, in colloidal drug delivery systems (for example liposomes, albumin microspheres, microemulsions, nanoparticles and nanocapsules) or in macroemulsions. Such techniques are disclosed in Remington's Pharmaceutical Sciences, supra.

In one aspect of the invention the composition is a liquid composition, such as an aqueous composition, and comprises a sulfoalkyl ether cyclodextrin derivative.

Parenteral formulations to be used for in vivo administration must be sterile. This is readily accomplished, for example, by filtration through sterile filtration membranes.

Suitable examples of sustained-release preparations include semi-permeable matrices of solid hydrophobic polymers containing the polypeptide or conjugate, the matrices having a suitable form such as a film or microcapsules. Examples of sustained-release matrices include polyesters, hydrogels (for example, poly(2-hydroxyethyl-methacrylate) or poly(vinylalcohol)), polylactides, copolymers of L-glutamic acid and ethyl-L-glutamate, non-degradable ethylene-vinyl acetate, degradable lactic acid-glycolic acid copolymers such as the ProLease® technology or Lupron Depot® (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for long periods such as up to or over 100 days, certain hydrogels release proteins for shorter time periods. When encapsulated polypeptides remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Oral administration of the peptides and peptide conjugates is an intended practice of the invention. For oral administration, the pharmaceutical composition may be in solid or liquid form, e.g. in the form of a capsule, tablet, suspension, emulsion or solution. The pharmaceutical composition is preferably made in the form of a dosage unit containing a given amount of the active ingredient. A suitable daily dose for a human or other mammal may vary widely depending on the condition of the patient and other factors, but can be determined by persons skilled in the art using routine methods.

Solid dosage forms for oral administration may include capsules, tablets, suppositories, powders and granules. In such solid dosage forms, the active compound may be admixed with at least one inert diluent such as sucrose, lactose, or starch. Such dosage forms may also comprise, as is normal practice, additional substances, e.g. lubricating agents such as magnesium stearate. In the case of capsules, tablets and pills, the dosage forms may also comprise buffering agents. Tablets and pills can additionally be prepared with enteric coatings.

The polypeptides or conjugates may be admixed with adjuvants such as lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, they may be dissolved in saline, water, polyethylene glycol, propylene glycol, ethanol, oils (such as corn oil, peanut oil, cottonseed oil or sesame oil), tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be subjected to conventional pharmaceutical operations such as sterilization and/or may contain conventional adjuvants such as preservatives, stabilizers, wetting agents, emulsifiers, buffers, fillers, etc., e.g. as disclosed elsewhere herein.

Liquid dosage forms for oral administration may include pharmaceutically acceptable emulsions, solutions, suspensions, syrups and elixirs containing inert diluents commonly used in the art, such as water. Such compositions may also comprise adjuvants such as wetting agents, sweeteners, flavoring agents and perfuming agents.

Formulations suitable for pulmonary administration are intended as part of the invention. Formulations suitable for use with a nebulizer, either jet or ultrasonic, will typically comprise the polypeptide or conjugate dissolved in water at a concentration of, e.g., about 0.01 to 25 mg of conjugate per mL of solution, preferably about 0.1 to 10 mg/mL. The formulation may also include a buffer and a simple sugar (e.g., for protein stabilization and regulation of osmotic pressure), and/or human serum albumin ranging in concentration from 0.1 to 10 mg/ml. Examples of buffers that may be used are sodium acetate, citrate and glycine. Preferably, the buffer will have a composition and molarity suitable to adjust the solution to a pH in the range of 3 to 9. Generally, buffer molarities of from 1 mM to 50 mM are suitable for this purpose. Examples of sugars which can be utilized are lactose, maltose, mannitol, sorbitol, trehalose, and xylose, usually in amounts ranging from 1% to 10% by weight of the formulation.

The nebulizer formulation may also contain a surfactant to reduce or prevent surface induced aggregation of the protein caused by atomization of the solution in forming the aerosol. Various conventional surfactants can be employed, such as polyoxyethylene fatty acid esters and alcohols, and polyoxyethylene sorbitan fatty acid esters. Amounts will generally range between 0.001% and 4% by weight of the formulation. An especially preferred surfactant for purposes of this invention is polyoxyethylene sorbitan monooleate.

Specific formulations and methods of generating suitable dispersions of liquid particles of the invention are described in WO 94/20069, U.S. Pat. No. 5,915,378, U.S. Pat. No. 5,960,792, U.S. Pat. No. 5,957,124, U.S. Pat. No. 5,934,272, U.S. Pat. No. 5,915,378, U.S. Pat. No. 5,855,564, U.S. Pat. No. 5,826,570 and U.S. Pat. No. 5,522,385 which are hereby incorporated by reference.

Formulations for use with a metered dose inhaler device will generally comprise a finely divided powder. This powder may be produced by lyophilizing and then milling a liquid conjugate formulation and may also contain a stabilizer such as human serum albumin (HSA). Typically, more than 0.5% (w/w) HSA is added. Additionally, one or more sugars or sugar alcohols may be added to the preparation if necessary. Examples include lactose maltose, mannitol, sorbitol, sorbitose, trehalose, xylitol, and xylose. The amount added to the formulation can range from about 0.01 to 200% (w/w), preferably from approximately 1 to 50%, of the conjugate present. Such formulations are then lyophilized and milled to the desired particle size.

The properly sized particles are then suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant. This mixture is then loaded into the delivery device. An example of a commercially available metered dose inhaler suitable for use in the present invention is the Ventolin metered dose inhaler, manufactured by Glaxo Inc., Research Triangle Park, N.C., USA.

Formulations for powder inhalers will comprise a finely divided dry powder containing polypeptides or polypeptide conjugates and may also include a bulking agent, such as lactose, sorbitol, sucrose, or mannitol in amounts which facilitate dispersal of the powder from the device, e.g., 50% to 90% by weight of the formulation. The particles of the powder shall have aerodynamic properties in the lung corresponding to particles with a density of about 1 $g/cm^2$ having a median diameter less than 10 micrometers, preferably between 0.5 and 5 micrometers, most preferably of between 1.5 and 3.5 micrometers. An example of a powder inhaler suitable for use in accordance with the teachings herein is the Spinhaler powder inhaler, manufactured by Fisons Corp., Bedford, Mass., USA. The powders for these devices may be generated and/or delivered by methods disclosed in U.S. Pat. No. 5,997,848, U.S. Pat. No. 5,993,783, U.S. Pat. No. 5,985,248, U.S. Pat. No. 5,976,574, U.S. Pat. No. 5,922,354, U.S. Pat. No. 5,785,049 and U.S. Pat. No. 5,654,007.

Mechanical devices designed for pulmonary delivery of therapeutic products, include but are not limited to nebulizers, metered dose inhalers, and powder inhalers, all of which are familiar to those of skill in the art. Specific examples of commercially available devices suitable for the practice of this invention are the Ultravent nebulizer, manufactured by Mallinckrodt, Inc., St. Louis, Mo., USA; the Acorn II nebulizer, manufactured by Marquest Medical Products, Englewood, Colo., USA; the Ventolin metered dose inhaler, manufactured by Glaxo Inc., Research Triangle Park, N.C., USA; the Spinhaler powder inhaler, manufactured by Fisons Corp., Bedford, Mass., USA the "standing cloud" device of Nektar Therapeutics, Inc., San Carlos, Calif., USA; the AIR inhaler manufactured by Alkermes, Cambridge, Mass., USA; and the AERx pulmonary drug delivery system manufactured by Aradigm Corporation, Hayward, Calif., USA.

The present invention also provides kits including the polypeptides, conjugates, polynucleotides, expression vectors, cells, methods, compositions, and systems, and apparatuses of the invention. Kits of the invention optionally comprise at least one of the following of the invention: (1) an apparatus, system, system component, or apparatus component as described herein; (2) at least one kit component comprising a polypeptide or conjugate or polynucleotide of the invention; a plasmid expression vector encoding a polypeptide of the invention; a cell expressing a polypeptide of the invention; or a composition comprising at least one of any such component; (3) instructions for practicing any method described herein, including a therapeutic or prophylactic method, instructions for using any component identified in (2) or any composition of any such component; and/or instructions for operating any apparatus, system or component described herein; (4) a container for holding said at least one such component or composition, and (5) packaging materials.

In a further aspect, the present invention provides for the use of any apparatus, component, composition, or kit described above and herein, for the practice of any method or assay described herein, and/or for the use of any apparatus, component, composition, or kit to practice any assay or method described herein.

Chemical Modifications, Conjugates, and Fusions

Any polypeptide of the invention may be present as part of a larger polypeptide sequence, e.g. a fusion protein, such as occurs upon the addition of one or more domains or subsequences for stabilization or detection or purification of the polypeptide. A polypeptide purification subsequence may include, e.g., an epitope tag, a FLAG tag, a polyhistidine sequence, a GST fusion, or any other detection/purification subsequence or "tag" known in the art. These additional domains or subsequences either have little or no effect on the activity of the polypeptide of the invention, or can be removed by post synthesis processing steps such as by treatment with a protease, inclusion of an intein, or the like.

The invention includes fusion proteins comprising a polypeptide of the invention, e.g., as described herein, fused to an Ig molecule, e.g., a human IgG Fc ("fragment crystallizable," or fragment complement binding) hinge, CH2 domain and CH3 domain, and nucleotide sequences encoding such fusion protein. Fc is the portion of the antibody responsible for binding to antibody receptors on cells and the C1q component of complement. These fusion proteins and their encoding nucleic acids are useful as prophylactic and/or therapeutic drugs or as diagnostic tools (see also, e.g., Challita-Eid, P. et al. (1998) J. Immunol 160:3419-3426; Sturmhoefel, K. et al. (1999) Cancer Res 59:4964-4972). The invention also includes fusion proteins comprising a polypeptide of the invention, fused to an albumin molecule, such as human serum albumin (HSA), as described, for example, in U.S. Pat. No. 5,876,969, and nucleotide sequences encoding the fusion protein. The Ig and albumin fusion proteins may exhibit increased polypeptide serum half-life and/or functional in vivo half-life, reduced polypeptide antigenicity, increased polypeptide storage stability, or increasing bioavailability, e.g. increased $AUC_{sc}$, and are thus may be useful as prophylactic and/or therapeutic drugs.

All of the polypeptides of the invention have an inherent ability to transduce across cellular membranes and affect therapeutic functions within cells. The invention therefore provides for the use of the polypeptides of the invention to enhance the cell permeability or transducibility of any other molecule. The invention further provides for the use of any fragment or subfragment of the polypeptides of the invention to enhance the cell permeability of any other molecule, such fragments or subfragments being of about 5 amino acids in length, of about 10 amino acids in length, such as 15 amino acids in length, e.g. about 20 amino acids in length, of about 25 amino acids in length, of about 30 amino acids in length, such as 35 amino acids in length, of about 35-50 amino acids in length, of about 50-100 amino acids in length, such as 75 amino acids in length, e.g. 100-125 amino acids in length.

Any polypeptide of the invention may also comprise one or more modified amino acid. The modified amino acid may be, e.g., a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent. The presence of modified amino acids may be advantageous in, for example, (a) increasing polypeptide serum half-life and/or functional in vivo half-life, (b) reducing polypeptide antigenicity, (c) increasing polypeptide storage stability, or (d) increasing bioavailability, e.g. increasing the $AUC_{sc}$. Amino acid(s) are modified, for example, co-translationally or post-translationally during recombinant production (e.g., N-linked glycosylation at N—X—S/T motifs during expression in mammalian cells) or modified by synthetic means.

The term "conjugate" (or interchangeably "polypeptide conjugate" or "conjugated polypeptide") is intended to indicate a heterogeneous (in the sense of composite) molecule formed by the covalent attachment of one or more polypeptides of the invention to one or more non-polypeptide moieties. The term "covalent attachment" means that the polypeptide and the non-polypeptide moiety are either directly covalently joined to one another, or else are indirectly covalently joined to one another through an intervening moiety or moieties, such as a bridge, spacer, or linkage moiety or moieties. Preferably, a conjugated polypeptide is soluble at relevant concentrations and conditions, i.e. soluble in physiological fluids such as blood. Examples of conjugated polypeptides of the invention include glycosylated and/or PEGylated polypeptides. The term "non-conjugated polypeptide" may be used to refer to the polypeptide part of the conjugated polypeptide.

The term "non-polypeptide moiety" is intended to mean a molecule that is capable of conjugating to an attachment group of the polypeptide. Preferred examples of non-polypeptide moieties include polymer molecules, sugar moieties, lipophilic compounds, or organic derivatizing agents, in particular polymer molecules or sugar moieties. It will be understood that the non-polypeptide moiety is linked to the polypeptide through an attachment group of the polypeptide. Except where the number of non-polypeptide moieties, such as polymer molecule(s), attached to the polypeptide is expressly indicated, every reference to "a non-polypeptide moiety" attached to the polypeptide or otherwise used in the present invention shall be a reference to one or more non-polypeptide moieties attached to the polypeptide.

The term "polymer molecule" is defined as a molecule formed by covalent linkage of two or more monomers, wherein none of the monomers is an amino acid residue. The term "polymer" may be used interchangeably with the term "polymer molecule".

The term "sugar moiety" is intended to indicate a carbohydrate molecule attached by in vivo or in vitro glycosylation, such as N- or O-glycosylation. An "N-glycosylation site" has the sequence N—X—S/T/C, wherein X is any amino acid residue except proline, N is asparagine and S/T/C is either serine, threonine or cysteine, preferably serine or threonine, and most preferably threonine. An "O-glycosylation site" comprises the OH-group of a serine or threonine residue.

The term "attachment group" is intended to indicate an amino acid residue group capable of coupling to the relevant non-polypeptide moiety such as a polymer molecule or a sugar moiety.

For in vivo N-glycosylation, the term "attachment group" is used in an unconventional way to indicate the amino acid residues constituting an N-glycosylation site (with the sequence N—X—S/T/C, wherein X is any amino acid residue except proline, N is asparagine and S/T/C is either serine, threonine or cysteine, preferably serine or threonine, and most preferably threonine). Although the asparagine residue of the N-glycosylation site is the one to which the sugar moiety is attached during glycosylation, such attachment cannot be achieved unless the other amino acid residues of the N-glycosylation site is present. Accordingly, when the non-polypeptide moiety is a sugar moiety and the conjugation is to be achieved by N-glycosylation, the term "amino acid residue comprising an attachment group for the non-polypeptide moiety" as used in connection with alterations of the amino acid sequence of the polypeptide of the invention is to be understood as one, two or all of the amino acid residues constituting an N-glycosylation site is/are to be altered in such a manner that either a functional N-glycosylation site is introduced into the amino acid sequence, removed from said sequence, or a functional N-glycosylation site is retained in the amino acid sequence (e.g. by substituting a serine residue, which already constitutes part of an N-glycosylation site, with a threonine residue and vice versa).

The term "introduce" (i.e., an "introduced" amino acid residue, "introduction" of an amino acid residue) is primarily intended to mean substitution of an existing amino acid residue for another amino acid residue, but may also mean insertion of an additional amino acid residue.

The term "remove" (i.e., a "removed" amino acid residue, "removal" of an amino acid residue) is primarily intended to mean substitution of the amino acid residue to be removed for another amino acid residue, but may also mean deletion (without substitution) of the amino acid residue to be removed.

The term "amino acid residue comprising an attachment group for the non-polypeptide moiety" is intended to indicate that the amino acid residue is one to which the non-polypeptide moiety binds (in the case of an introduced amino acid residue) or would have bound (in the case of a removed amino acid residue).

The term "functional in vivo half-life" is used in its normal meaning, i.e. the time at which 50% of the biological activity of the polypeptide is still present in the body/target organ, or the time at which the activity of the polypeptide is 50% of the initial value. The functional in vivo half-life may be determined in an experimental animal, such as rat, mouse, rabbit, dog or monkey. Preferably, the functional in vivo half-life is determined in a non-human primate, such as a monkey. Furthermore, the functional in vivo half-life may be determined for a sample that has been administered intravenously or subcutaneously.

As an alternative to determining functional in vivo half-life, "serum half-life" may be determined, i.e. the time at which 50% of the polypeptide circulates in the plasma or bloodstream prior to being cleared. Determination of serum half-life is often more simple than determining the functional in vivo half-life and the magnitude of serum half-life is usually a good indication of the magnitude of functional in vivo half-life. Alternatively terms to serum half-life include "plasma half-life", "circulating half-life", "serum clearance", "plasma clearance" and "clearance half-life".

Polynucleotides and Methods of Mutagenesis

The invention includes nucleic acids and polynucleotides that encode the polypeptides of the invention. The invention includes compositions produced by digesting one or more of any of the polynucleotides of the invention with a restriction endonuclease, an RNAse, or a DNAse (e.g., as is performed in certain of the recombination formats elsewhere in the specification); and compositions produced by fragmenting or shearing one or more polynucleotides of the invention by mechanical means (e.g., sonication, vortexing, and the like), which can also be used to provide substrates for recombination in the methods described herein. The invention also provides compositions produced by cleaving at least one of any of the polynucleotides of the invention. The cleaving may comprise mechanical, chemical, or enzymatic cleavage, and the enzymatic cleavage may comprise cleavage with a restriction endonuclease, an RNAse, or a DNAse.

Also included in the invention are compositions produced by a process comprising incubating one or more of the fragmented polynucleotides of the invention in the presence of ribonucleotide or deoxyribonucleotide triphosphates and a nucleic acid polymerase. This resulting composition forms a recombination mixture for many of the recombination formats noted above. The nucleic acid polymerase may be an RNA polymerase, a DNA polymerase, or an RNA-directed DNA polymerase (e.g., a "reverse transcriptase"); the polymerase can be, e.g., a thermostable DNA polymerase (e.g., VENT, TAQ, or the like).

Similarly, compositions comprising sets of oligonucleotides corresponding to more than one nucleic acids of the invention are useful as recombination substrates and are a feature of the invention. For convenience, these fragmented, sheared, or oligonucleotide synthesized mixtures are referred to as fragmented nucleic acid sets.

The invention also provides an isolated or recombinant nucleic acid encoding a polypeptide produced by mutating or recombining at least one polynucleotide of the invention.

Polynucleotides, oligonucleotides, and nucleic acid fragments of the invention can be prepared by standard solid-phase methods, according to known synthetic methods. Typically, fragments of up to about 100 bases are individually synthesized, then joined (e.g., by enzymatic or chemical ligation methods, or polymerase mediated recombination methods) to form essentially any desired continuous sequence. For example, the polynucleotides and oligonucleotides of the invention can be prepared by chemical synthesis using, e.g., classical phosphoramidite method described by, e.g., Beaucage et al. (1981) Tetrahedron Letters 22:1859-69, or the method described by Matthes et al. (1984) EMBO J 3:801-05, e.g., as is typically practiced in automated synthetic methods. According to the phosphoramidite method, oligonucleotides are synthesized, e.g., in an automatic DNA synthesizer, purified, annealed, ligated and cloned into appropriate vectors.

In addition, essentially any polynucleotide can be custom ordered from any of a variety of commercial sources, such as Operon Technologies Inc. (Alameda, Calif.) and many others. Similarly, peptides and antibodies can be custom ordered from any of a variety of sources, e.g., Celtek Peptides (Nashville, Tenn.); Washington Biotechnology, Inc. (Baltimore Md.); Global Peptide Services (Ft. Collin Colo.), and many others.

Certain polynucleotides of the invention may also be obtained by screening cDNA libraries (e.g., libraries generated by recombining homologous nucleic acids as in typical recursive sequence recombination methods) using oligonucleotide probes that can hybridize to or PCR-amplify polynucleotides which encode OAS polypeptides and fragments of those polypeptides. Procedures for screening and isolating cDNA clones are well-known to those of skill in the art. Such techniques are described in, e.g., Berger and Kimmel, Guide to Molecular Cloning Techniques, Methods in Enzymol. Vol. 152, Acad. Press, Inc., San Diego, Calif. ("Berger"); J. Sambrook and D. W. Russell, Molecular Cloning: A Laboratory Manual, Third Edition. Cold Spring Harbor Press, Cold Spring Harbor, N.Y., ("Sambrook"); and F. M. Ausubel et al. (1987-2005) Current Protocols in Molecular Biology. Wiley Interscience, New York, N.Y. ("Ausubel"). Some polynucleotides of the invention can be obtained by altering a naturally occurring sequence, e.g., by mutagenesis, recursive sequence recombination (e.g., shuffling), or oligonucleotide recombination. In other cases, such polynucleotides can be made in silico or through oligonucleotide recombination methods as described in the references cited herein.

As described in more detail herein, the polynucleotides of the invention include polynucleotides that encode polypeptides of the invention, polynucleotide sequences complementary to these polynucleotide sequences, and polynucleotides that hybridize under at least stringent conditions to the sequences defined herein. A coding sequence refers to a polynucleotide sequence encoding a particular polypeptide or domain, region, or fragment of said polypeptide. The polynucleotides of the invention may be in the form of RNA or in the form of DNA, and include mRNA, cRNA, synthetic RNA and DNA, and cDNA. The polynucleotides may be double-stranded or single-stranded, and if single-stranded, can be the coding strand or the non-coding (anti-sense, complementary) strand. The polynucleotides of the invention include the coding sequence of a polypeptide of the invention (i) in isolation, (ii) in combination with one or more additional coding sequences, so as to encode, e.g., a fusion protein, a pre-protein, a prepro-protein, or the like, (iii) in combination with non-coding sequences, such as introns, control elements, such as a promoter (e.g., naturally occurring or recombinant or shuffled promoter), a terminator element, or 5' and/or 3' untranslated regions effective for expression of the coding sequence in a suitable host, and/or (iv) in a vector, cell, or host environment in which the coding sequence is a heterologous gene.

Polynucleotides of the invention can also be found in combination with typical compositional formulations of nucleic acids, including in the presence of carriers, buffers, adjuvants, excipients, and the like, as are known to those of ordinary skill in the art. Polynucleotide fragments typically comprise at least about 200 nucleotide bases, such as at least about 250, 300, 350, 400, 450, 460, 470, or more bases. The nucleotide fragments of polynucleotides of the invention may hybridize under highly stringent conditions to a polynucleotide sequence described herein and/or encode amino acid sequences having at least one of the properties of polypeptides of the invention described herein.

The polynucleotides of the invention have a variety of uses in, for example, recombinant production (i.e., expression) of the polypeptides of the invention typically through expression of a plasmid expression vector comprising a sequence encoding the polypeptide or fragment thereof; as therapeutics; as prophylactics; as diagnostic tools; as immunogens; as adjuvants; as diagnostic probes for the presence of complementary or partially complementary nucleic acids (including for detection of a wild-type oligoadenylate synthetase nucleic acid), as substrates for further reactions, e.g., recursive sequence recombination reactions or mutation reactions to produce new and/or improved variants, and the like.

Expression Vectors, Methods of Manufacturing, Gene Therapy

Recombinant methods for producing and isolating polypeptides of the invention are described herein. In addition to recombinant production, the polypeptides may be produced by direct peptide synthesis using solid-phase techniques (see, e.g., Stewart et al. (1969) Solid-Phase Peptide Synthesis, WH Freeman Co, San Francisco; Merrifield J. (1963) J Am Chem Soc 85:2149-2154). Peptide synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer. For example, subsequences may be chemically synthesized separately and combined using chemical methods to provide full-length polypeptides or fragments thereof. Alternatively, such sequences may be ordered from any number of companies which specialize in production of polypeptides. Most commonly, polypeptides of the invention may be produced by expressing coding nucleic acids and recovering polypeptides, e.g., as described below.

Methods for producing the polypeptides of the invention are also included. One such method comprises introducing into a population of cells any nucleic acid of the invention, which is operatively linked to a regulatory sequence effective to produce the encoded polypeptide, culturing the cells in a culture medium to express the polypeptide, and isolating the polypeptide from the cells or from the culture medium. An amount of nucleic acid sufficient to facilitate uptake by the cells (transfection) and/or expression of the polypeptide is utilized. The nucleic acid is introduced into such cells by any delivery method as is known in the art, including, e.g., injection, gene gun, passive uptake, etc. As one skilled in the art will recognize, the nucleic acid may be part of a vector, such as a recombinant expression vector, including a DNA plasmid vector, or any vector as known in the art. The nucleic acid or vector comprising a nucleic acid of the invention may be prepared and formulated by standard recombinant DNA technologies and isolation methods as known in the art. Such a nucleic acid or expression vector may be introduced into a population of cells of a mammal in vivo, or selected cells of the mammal (e.g., tumor cells) may be removed from the mammal and the nucleic acid expression vector introduced ex vivo into the population of such cells in an amount sufficient such that uptake and expression of the encoded polypeptide results. Or, a nucleic acid or vector comprising a nucleic acid of the invention is produced using cultured cells in vitro. In one aspect, the method of producing a polypeptide of the invention comprises introducing into a population of cells a recombinant expression vector comprising any nucleic acid of the invention described herein in an amount and formula such that uptake of the vector and expression of the encoded polypeptide will result; administering the expression vector into a mammal by any introduction/delivery format described herein; and isolating the polypeptide from the mammal or from a byproduct of the mammal.

The invention provides isolated or recombinant nucleic acids (also referred to herein as polynucleotides), collectively referred to as "nucleic acids (or polynucleotides) of the invention", which encode polypeptides of the invention. The polynucleotides of the invention are useful in a variety of applications. As discussed above, the polynucleotides are useful in producing polypeptides of the invention. In addition, polynucleotides of the invention can be incorporated into expression vectors useful for gene therapy, DNA vaccination, and immunotherapy, as described elsewhere in this application.

Any of the polynucleotides of the invention (which includes those described above) may encode a fusion protein comprising at least one additional amino acid sequence, such as, for example, a secretion/localization sequence, a sequence useful for solubilization or immobilization (e.g., for cell surface display) of the polypeptide, a sequence useful for detection and/or purification of the polypeptide (e.g., a polypeptide purification subsequence, such as an epitope tag, a polyhistidine sequence, and the like). In another aspect, the invention provides cells comprising one or more of the polynucleotides of the invention. Such cells may express one or more polypeptides encoded by the polynucleotides of the invention.

The invention also provides vectors comprising any of the polynucleotides of the invention. Such vectors may comprise a plasmid, a cosmid, a phage, a virus, or a fragment of a virus. Such vectors may comprise an expression vector, and, if desired, the nucleic acid is operably linked to a promoter, including those discussed herein and below. Furthermore, in another aspect, the invention provides compositions comprising an excipient or carrier and at least one of any of the polynucleotides of the invention, or vectors, cells, or host comprising such nucleic acids. Such composition may be pharmaceutical compositions, and the excipient or carrier may be a pharmaceutically acceptable excipient or carrier.

The invention also includes compositions comprising two or more nucleic acids of the invention, or fragments thereof (e.g., as substrates for recombination). The composition can comprise a library of recombinant nucleic acids, where the library contains at least 2, at least 3, at least 5, at least 10, at least 20, at least 50, or at least 100 or more nucleic acids described above. The nucleic acids are optionally cloned into expression vectors, providing expression libraries.

The polynucleotides of the invention and fragments thereof, as well as vectors comprising such polynucleotides, may be employed for therapeutic or prophylactic uses in combination with a suitable carrier, such as a pharmaceutical carrier. Such compositions comprise a therapeutically and/or prophylactically effective amount of the compound, and a pharmaceutically acceptable carrier or excipient. Such a carrier or excipient includes, but is not limited to, saline, buffered saline, dextrose, water, glycerol, ethanol, and combinations thereof. The formulation should suit the mode of administration. Methods of administering nucleic acids, polypeptides, and proteins are well known in the art.

General texts that describe molecular biological techniques useful herein, including the use of vectors, promoters and many other relevant topics, include Berger, supra; Sambrook (1989), supra, and Ausubel, supra. Examples of techniques sufficient to direct persons of skill through in vitro amplification methods, including the polymerase chain reaction (PCR) the ligase chain reaction (LCR), Q beta-replicase amplification and other RNA polymerase mediated techniques (e.g., NASBA), e.g., for the production of the homologous nucleic acids of the invention are found in Berger, Sambrook, and Ausubel, all supra, as well as Mullis et al. (1987) U.S. Pat. No. 4,683,202; PCR Protocols: A Guide to Methods and Applications (Innis et al., eds.) Academic Press Inc. San Diego, Calif. (1990) ("Innis"); Arnheim & Levinson (Oct. 1, 1990) C&EN 36-47; The Journal Of NIH Research (1991) 3:81-94; (Kwoh et al. (1989) Proc Natl Acad Sci USA 86:1173-1177; Guatelli et al. (1990) Proc Natl Acad Sci USA 87:1874-1878; Lomeli et al. (1989) J Clin Chem 35:1826-1831; Landegren et al. (1988) Science 241:1077-1080; Van Brunt (1990) Biotechnology 8:291-294; Wu and Wallace (1989) Gene 4:560-569; Barringer et al. (1990) Gene 89:117-122, and Sooknanan and Malek (1995) Biotechnology 13:563-564. Improved methods of cloning in vitro amplified nucleic acids are described in Wallace et al., U.S. Pat. No. 5,426,039. Improved methods of amplifying large nucleic acids by PCR are summarized in Cheng et al. (1994) Nature 369:684-685 and the references therein, in which PCR amplicons of up to 40 kilobases (kb) are generated. One of skill will appreciate that essentially any RNA can be converted into a double stranded DNA suitable for restriction digestion, PCR expansion and sequencing using reverse transcriptase and a polymerase. See Ausubel, Sambrook and Berger, all supra.

In mammalian host cells, a number of expression systems, such as viral-based systems, may be utilized. In cases where an adenovirus is used as an expression vector, a coding sequence is optionally ligated into an adenovirus transcription/translation complex consisting of the late promoter and tripartite leader sequence. Insertion in a nonessential E1 or E3 region of the viral genome results in a viable virus capable of expressing a polypeptide of the invention in infected host cells (Logan and Shenk (1984) Proc Natl Acad Sci USA 81:3655-3659). In addition, transcription enhancers, such as the rous sarcoma virus (RSV) enhancer, are used to increase expression in mammalian host cells. Host cells, media, expression systems, and methods of production include those known for cloning and expression of various mammalian proteins. The efficiency of expression can be enhanced by the inclusion of enhancers appropriate to the cell system in use (see, e.g., Scharf D. et al. (1994) Results Probl Cell Differ 20:125-62; and Bittner et al. (1987) Methods in Enzymol 153:516-544).

Specific initiation signals can aid in efficient translation of a polynucleotide coding sequence of the invention and/or fragments thereof. These signals can include, e.g., the ATG initiation codon and adjacent sequences. In cases where a coding sequence, its initiation codon and upstream sequences are inserted into the appropriate expression vector, no additional translational control signals may be needed. However, in cases where only coding sequence (e.g., a mature protein coding sequence), or a portion thereof, is inserted, exogenous nucleic acid transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic.

Introduction of the construct into the host cell can be effected by calcium phosphate transfection, DEAE-Dextran mediated transfection, electroporation, gene or vaccine gun, injection, or other common techniques (see, e.g., Davis, L., Dibner, M., and Battey, I. (1986) Basic Methods in Molecular Biology) for in vivo, ex vivo or in vitro methods.

As noted, many references are available for the culture and production of many cells, including cells of bacterial, plant, animal (especially mammalian) and archebacterial origin. See, e.g., Sambrook, Ausubel, and Berger (all supra), as well as Freshney (1994) Culture of Animal Cells, a Manual of Basic Technique, third edition, Wiley-Liss, New York and the references cited therein; Doyle and Griffiths (1997) Mammalian Cell Culture: Essential Techniques John Wiley and Sons, New York; Humason (1979) Animal Tissue Techniques, fourth edition W.H. Freeman and Company; and Ricciardelli et al. (1989) In vitro Cell Dev Biol 25:1016-1024. For plant cell culture and regeneration see, e.g., Payne et al. (1992) Plant Cell and Tissue Culture in Liquid Systems John Wiley & Sons, Inc. New York, N.Y.; Gamborg and Phillips (eds.) (1995) Plant Cell, Tissue and Organ Culture; Fundamental Methods Springer Lab Manual, Springer-Verlag (Berlin Heidelberg New York) and Plant Molecular Biology (1993) R. R. D. Croy (ed.) Bios Scientific Publishers, Oxford, U.K. ISBN 0 12 198370 6. Cell culture media in general are set forth in Atlas and Parks (eds.) The Handbook of Microbiological Media (1993) CRC Press, Boca Raton, Fla. Additional information for cell culture is found in available commercial literature such as the Life Science Research Cell Culture Catalogue from Sigma-Aldrich, Inc (St Louis, Mo.) ("Sigma-LSRCCC") and, e.g., the Plant Culture Catalogue and supplement also from Sigma-Aldrich, Inc (St Louis, Mo.) ("Sigma-PCCS").

Polypeptides of the invention can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems noted herein), hydroxylapatite chromatography, and lectin chromatography. Protein refolding steps can be used, as desired, in completing configuration of the mature protein or fragments thereof. Finally, high performance liquid chromatography (HPLC) can be employed in the final purification steps. In addition to the references noted, supra, a variety of purification methods are well known in the art, including, e.g., those set forth in Sandana (1997) Bioseparation of Proteins, Academic Press, Inc.; Bollag et al. (1996) Protein Methods, 2.sup.nd Edition Wiley-Liss, New York; Walker (1996) The Protein Protocols Handbook Humana Press, New Jersey; Harris and Angal (1990) Protein Purification Applications: A Practical Approach IRL Press at Oxford, Oxford, England; Harris and Angal Protein Purification Methods: A Practical Approach IRL Press at Oxford, Oxford, England; Scopes (1993) Protein Purification: Principles and Practice 3.sup.rd Edition Springer Verlag, New York; Janson and Ryden (1998) Protein Purification: Principles, High Resolution Methods and Applications, Second Edition Wiley-VCH, New York; and Walker (1998) Protein Protocols on CD-ROM Humana Press, New Jersey.

A number of viral vectors suitable for organismal in vivo transduction and expression are known. Such vectors include retroviral vectors (see, e.g., Miller, Curr Top Microbiol Immunol (1992) 158:1-24; Salmons and Gunzburg (1993) Human Gene Therapy 4:129-141; Miller et al. (1994) Methods in Enzymology 217:581-599) and adeno-associated vectors (reviewed in Carter (1992) Curr Opinion Biotech 3:533-539; Muzcyzka (1992) Curr Top Microbiol Immunol. 158: 97-129). Other viral vectors that are used include adenoviral vectors, herpes viral vectors and Sindbis viral vectors, as generally described in, e.g., Jolly (1994) Cancer Gene Therapy 1:51-64; Latchman (1994) Molec Biotechnol 2:179-195; and Johanning et al. (1995) Nucl Acids Res 23:1495-1501.

In one aspect, a pox virus vector can be used. The pox viral vector is transfected with a polynucleotide sequence encoding a polypeptide of the invention and is useful in prophylactic, therapeutic and diagnostic applications where enhancement of an immune response, such as e.g., increased or improved T cell proliferation is desired. See viral vectors discussed in, e.g., Berencsi et al., J Infect Dis (2001) 183 (8):1171-9; Rosenwirth et al., Vaccine 2001 Feb. 8; 19(13-14):1661-70; Kittlesen et al., J Immunol (2000) 164 (8):4204-11; Brown et al. Gene Ther 2000 7 (19):1680-9; Kanesathasan et al., Vaccine (2000) 19 (4-5):483-91; Sten (2000) Drug 60 (2):249-71. Compositions comprising such vectors and an acceptable excipient are also a feature of the invention.

Gene therapy and genetic vaccines provide methods for combating chronic infectious diseases (e.g., HIV infection, viral hepatitis), as well as non-infectious diseases including cancer and some forms of congenital defects such as enzyme deficiencies, and such methods can be employed with polynucleotides of the invention, including, e.g., vectors and cells comprising such polynucleotides. Several approaches for introducing nucleic acids and vectors into cells in vivo, ex vivo and in vitro have been used and can be employed with polynucleotides of the invention, and vectors comprising such polynucleotides. These approaches include liposome based gene delivery (Debs and Zhu (1993) WO 93/24640 and U.S. Pat. No. 5,641,662; Mannino and Gould-Fogerite (1988) BioTechniques 6 (7):682-691; Rose, U.S. Pat. No. 5,279,833; Brigham (1991) WO 91/06309; and Feigner et al. (1987) Proc Natl Acad Sci USA 84:7413-7414; Brigham et al. (1989) Am J Med Sci 298:278-281; Nabel et al. (1990) Science 249: 1285-1288; Hazinski et al. (1991) Am J Resp Cell Molec Biol 4:206-209; and Wang and Huang (1987) Proc Natl Acad Sci USA 84:7851-7855); adenoviral vector mediated gene delivery, e.g., to treat cancer (see, e.g., Chen et al. (1994) Proc Natl Acad Sci USA 91:3054-3057; Tong et al. (1996) Gynecol Oncol 61:175-179; Clayman et al. (1995) Cancer Res. 5:1-6; O'Malley et al. (1995) Cancer Res 55:1080-1085; Hwang et al. (1995) Am J Respir Cell Mol Biol 13:7-16; Haddada et al. (1995) Curr Top Microbiol Immunol. 1995 (Pt. 3):297-306; Addison et al. (1995) Proc Natl Acad Sci USA 92:8522-8526; Colak et al. (1995) Brain Res 691:76-82; Crystal (1995) Science 270:404-410; Elshami et al. (1996) Human Gene Ther 7:141-148; Vincent et al. (1996) J Neurosurg 85:648-654), and many others. Replication-defective retroviral vectors harboring therapeutic polynucleotide sequence as part of the retroviral genome have also been used, particularly with regard to simple MuLV vectors. See, e.g., Miller et al. (1990) Mol Cell Biol 10:4239 (1990); Kolberg (1992) J NIH Res 4:43, and Cornetta et al. (1991) Hum Gene Ther 2:215). Nucleic acid transport coupled to ligand-specific, cation-based transport systems (Wu and Wu (1988) J Biol Chem, 263:14621-14624) has also been used. Naked DNA expression vectors have also been described (Nabel et al. (1990), supra); Wolff et al. (1990) Science, 247:1465-1468). In general, these approaches can be adapted to the invention by incorporating nucleic acids encoding the polypeptides of the invention into the appropriate vectors.

General texts which describe gene therapy protocols, which can be adapted to the present invention by introducing the nucleic acids of the invention into patients, include, e.g., Robbins (1996) Gene Therapy Protocols, Humana Press, New Jersey, and Joyner (1993) Gene Targeting: A Practical Approach, IRL Press, Oxford, England.

Antiviral Treatments

The polynucleotides and polypeptides of the invention may be used therapeutically or prophylactically to treat or prevent virus infection. Exemplary viruses include, but are not limited to, viruses of the Flaviviridae family, such as, for example, Hepatitis C Virus, Yellow Fever Virus, West Nile Virus, Japanese Encephalitis Virus, Dengue Virus, and Bovine Viral Diarrhea Virus; viruses of the Hepadnaviridae family, such as, for example, Hepatitis B Virus; viruses of the Picornaviridae family, such as, for example, Encephalomyocarditis Virus, Human Rhinovirus, and Hepatitis A Virus; viruses of the Retroviridae family, such as, for example, Human Immunodeficiency Virus, Simian Immunodeficiency Virus, Human T-Lymphotropic Virus, and Rous Sarcoma Virus; viruses of the Coronaviridae family, such as, for example, SARS coronavirus; viruses of the Rhabdoviridae family, such as, for example, Rabies Virus and Vesicular Stomatitis Virus, viruses of the Paramyxoviridae family, such as, for example, Respiratory Syncytial Virus and Parainfluenza Virus, viruses of the Papillomaviridae family, such as, for example, Human Papillomavirus, and viruses of the Herpesviridae family, such as, for example, Herpes Simplex Virus.

It is another object of the invention to provide conjugates, such conjugates comprising one or more non-polypeptide moiety linked to a polypeptide of the invention, which conjugate exhibits an antiviral property, and which optionally exhibits other desirable properties, such as increased serum half-life and/or functional in vivo half-life, and/or decreased antigenicity, compared to the non-conjugated polypeptide. Some such conjugates may exhibit enhanced efficacy in clearing a virus from cells infected with the virus, compared to a reference oligoadenylate synthetase. Some such conjugates may further have reduced toxicity compared to a reference oligoadenylate synthetase.

It is another object of the invention to provide a method of inhibiting viral replication in virus-infected cells, the method comprising administering to the virus-infected cells a polypeptide or conjugate of the invention in an amount effective to inhibit viral replication in said cells. The invention also provides a method of reducing the number of copies of a virus in virus-infected cells, comprising administering to the virus-infected cells a polypeptide or conjugate of the invention in an amount effective to reduce the number of copies of the virus in said cells. The cells may be in culture or otherwise isolated from a mammal (i.e., in vitro or ex vivo), or may be in vivo, e.g., in a subject, in a mammal, in a primate, or in man.

Anticancer and Inflammation Treatments

It has been demonstrated that the polypeptides of the invention can cause certain cell types and cell lines to undergo apoptosis or to affect growth retardation of said cell lines or cell types. Such cell lines or cell types include in an exemplary embodiment those derived from the prostate and breast.

The invention provides a method of inhibiting proliferation of a cell population, comprising contacting the cell population with a polypeptide of the invention in an amount effective to decrease proliferation of the cell population. The cell population may be in culture or otherwise isolated from a mammal (i.e., in vitro or ex vivo), or may be in vivo, e.g., in a subject, in a mammal, a primate, or man.

The invention provides for treating cancers and neoplastic diseases using the polypeptides and polynucleotides of the invention. Exemplary cancers and neoplastic diseases include but are not limited to: adrenocortical carcinoma, AIDS related cancers, such as for example, Kaposi's sarcoma, AIDS-related lymphoma, anal cancer, astrocytoma, basal cell carcinoma, bile duct cancers, such as for example those of an extrahepatic nature, bladder cancer, bone cancers, such as for example osteosarcomas and malignant fibrous histiocytomas, brain stem glioma, brain tumors, such as for example gliomas, astrocytomas, malignant gliomas, ependymomas, medulloblastomas, and neuroblastomas, supratentorial primitive neuroectodermal tumor, visual pathway and hypothalamic glioma, breast cancer, bronchial adenoma, Burkitt's lymphoma, carcinoid tumors, central nervous system lymphoma, cervical cancer, leukemias, such as for example, hairy cell leukemia, acute lymphoblastic leukemia, acute myeloid leukemia, chronic lymphocytic leukemia and chronic myelogenous leukemia, chronic myeloproliferative disorders, colorectal cancer, cutaneous T-cell lymphoma, endometrial cancer, esophageal cancer, Ewing's family of tumors, extracranial germ cell tumor, extragonadal germ cell tumor, eye cancers, such as for example, intraocular melanoma and retinoblastoma, gallbladder cancer, stomach cancer, gestational trophoblastic tumor, head and neck cancer, hepatocellular carcinoma, Hodgkin's lymphoma, Non-Hodgkin's lymphoma, primary CNS lymphoma, nasopharyngeal cancer, islet cell carcinoma, kidney (renal cell) cancer, laryngeal cancer, lip and oral cancer, liver cancer, lung cancer, such as for example non-small cell and small cell lung cancers, Waldenstrom's macroglobulinemia, Merkel cell carcinoma, mesothelioma, metastatic squamous neck cancer, multiple endocrine neoplasia, multiple myeloma, plasma cell neoplasm, mycosis fungoides, myelodysplastic syndromes, myeloproliferative diseases, nasal cavity and paranasal sinus cancer, ovarian cancer, such as germ cell and epithelial, low-malignant potential ovarian tumor, pancreatic cancer, parathyroid cancer, penile cancer, pheochromocytoma, pituitary tumor, pleuropulmonary blastoma, prostate cancer, rhabdomyosarcoma, salivary gland cancer, sarcomas, Sezary syndrome, skin cancer, such as for example melanoma and squamous cell carcinoma, testicular cancer, thymoma, thymic carcinoma, thyroid cancer, transitional cell cancer, trophoblastic tumor, urethral cancer, uterine cancer, vaginal cancer, vulvar cancer, and Wilms' tumor.

The invention further provides for treating autoimmune diseases and inflammation using the polypeptides and polynucleotides of the invention, said autoimmune and inflammatory diseases include but are not limited to: asthma, Crohn's disease, Guillain-Barre syndrome, multiple sclerosis, myasthenia gravis, optic neuritis, psoriasis, rheumatoid arthritis, Grave's disease, Hashimoto's (thyroiditis) disease, Ord's thyroiditis, diabetes, diabetes mellitus, Reiter's syndrome, autoimmune hepatitis, primary biliary cirrhosis, liver cirrhosis, liver fibrosis, antiphospholipid antibody syndrome, opsoclonus myoclonus syndrome, temporal arteritis, acute disseminated encephalomyelitis, Goodpasture's syndrome, Wegener's granulomatosis, coeliac disease, pemphigus, polyarthritis, warm autoimmune hemolytic anemia, Takayasu's arteritis, coronary artery disease, endometriosis, interstitial cystitis, neuromyotonia, scleroderma, vitiligo, vulvodynia, Chagas' disease, sarcoidosis, chronic fatigue syndrome, acute respiratory distress syndrome, tendonitis, bursitis, polymyalgia rheumatica, inflammatory bowel disease, chronic obstructive pulmonary disease, allergic rhinitis, cardiovascular disease, chronic cholecystitis, bronchiectasis, pneumoconiosis, such as for example, silicosis, osteoarthritis, atherosclerosis, dysautonomia, ankylosing spondylitis, acute anterior uveitis, systemic lupus erythematosus, insulin-dependent diabetes mellitus, pemphigus vulgaris, experimental allergic encephalomyelitis, experimental autoimmune uveorenitis, mixed connective tissue disease, Sjørgen's syndrome, autoimmune hemolytic anemia, autoimmune thrombocytopenic purpura, acute rheumatic fever, mixed essential cryoglobulinemia, juvenile rheumatoid arthritis, degenerative joint disease, ankylosing spondylitis, psoriatic arthritis, neuralgia, synoviitis, glomerulonephritis, vasculitis, inflammations that occur as sequellae to influenza, the common cold and other viral infections, gout, contact dermatitis, low back and neck pain, dysmenorrhea, headache, toothache, sprains, strains, myositis, burns, injuries, and pain and inflammation that follow surgical and dental procedures in a subject.

Cell Growth and Tissue Regeneration Treatments

The polypeptides of the invention have been shown to stimulate a mitogenic, cell growth-promoting program in specific cell types and cell lines, such as for example, Huh7 hepatoma cells and MRC5 fetal lung fibroblast cells. This mitogenic program is identified using expression microarray analysis and cell viability assays of cells and cell lines treated with the polypeptides of the invention. The invention provides for uses of the polypeptides of the invention to stimulate cell growth and tissue regeneration in vitro, in vivo, and ex vivo using tissues and cells derived from subjects or mammals.

Derivatives of the Polypeptides of the Invention

The invention provides for polypeptides that differ from any of the polypeptides of FIGS. 1-5 by 1 to 34 amino acids, such differences may include substitutions, insertions, deletions, the incorporation of modified amino acids or amino acid derivatives, and the addition or deletion of amino acids from the C-terminus or N-terminus of the polypeptides. One or more amino acid substitutions may be made to the polypeptides of the invention according to, for example, a substitution group (such as, a conservative substitution group), such as one set forth below. Alternatively, or in addition, one or more amino acid substitutions may made in the polypeptides which introduces or removes an amino acid residue comprising an attachment group for a non-polypeptide moiety. Examples include introduction of one or more N-glycosylation site(s), introduction of one or more cysteine residue(s) or lysine residue(s), removal of one or more N-glycosylation site(s), and/or or removal of one or more lysine(s) or histidine(s). Some such polypeptides exhibit an oligoadenylate synthetase activity. Conservative substitutions groups include: Group 1, Alanine (A) Glycine (G) Serine (S) Threonine (T), Group 2, Aspartic acid (D) Glutamic acid (E), Group 3, Asparagine (N) Glutamine (Q), Group 4, Arginine (R) Lysine (K) Histidine (H), Group 5, Isoleucine (I) Leucine (L) Methionine (M) Valine (V), and Group 6, Phenylalanine (F) Tyrosine (Y) Tryptophan (W). Other substitution groups of amino acids can be envisioned. For example, amino acids can be grouped by similar function or chemical structure or composition (e.g., acidic, basic, aliphatic, aromatic, sulfur-containing). For example, an Aliphatic grouping may comprise: Glycine (G), Alanine (A), Valine (V), Leucine (L), Isoleucine (I). Other groups containing amino acids that are considered conservative substitutions for one another include: Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). See also Creighton (1984) Proteins, W.H. Freeman and Company, for additional groupings of amino acids. Listing of a polypeptide sequence herein, in conjunction with the above substitution groups, provides an express listing of all conservatively substituted polypeptide sequences.

In one aspect, the invention provides isolated or recombinant polypeptides each comprising a sequence having at least 90% sequence identity (e.g., at least about 91%, at least about 92%, at least about 93%, at least about 94%, at least about 95%, at least about 96%, at least about 97%, at least about 98%, or at least about 99% amino acid sequence identity) to any one of the polypeptides of FIG. 5. In some instances the polypeptide exhibits oligoadenylate synthetase activity.

The degree to which a sequence (polypeptide or nucleic acid) is similar to another provides an indication of similar structural and functional properties for the two sequences. Accordingly, in the context of the present invention, sequences which have a similar sequence to any given exemplar sequence are a feature of the present invention. In particular, sequences that have percent sequence identities as defined below are a feature of the invention. A variety of methods of determining sequence relationships can be used, including manual alignment and computer assisted sequence alignment and analysis. A variety of computer programs for performing sequence alignments are available, or an alignment can be prepared manually by one of skill.

As noted above, the sequences of the polypeptides and nucleic acids employed in the subject invention need not be identical, but can be substantially identical to the corresponding sequence of a polypeptide of the invention or nucleic acid of the invention. For example, polypeptides of the invention can be subject to various changes, such as one or more amino acid insertions, deletions, and/or substitutions, either conservative or non-conservative, including where, e.g., such changes might provide for certain advantages in their use, such as, in their therapeutic or prophylactic use or administration or diagnostic application. The nucleic acids of the invention can also be subject to various changes, such as one or more substitutions of one or more nucleic acids in one or more codons such that a particular codon encodes the same or a different amino acid, resulting in either a silent variation (as defined herein) or non-silent variation, or one or more deletions of one or more nucleic acids (or codons) in the sequence. The nucleic acids can also be modified to include one or more codons that provide for optimum expression in an expression system (e.g., bacterial or mammalian), while, if desired, said one or more codons still encode the same amino acid(s). Such nucleic acid changes might provide for certain advantages in their therapeutic or prophylactic use or administration, or diagnostic application. The nucleic acids and polypeptides can be modified in a number of ways so long as they comprise a sequence substantially identical (as defined below) to a sequence in a respective nucleic acid or polypeptide of the invention.

The term "identical" or "identity," in the context of two or more nucleic acid or polypeptide sequences, refers to two or more sequences that are the same or have a specified percentage of amino acid residues or nucleotides that are the same, when compared and aligned for maximum similarity, as determined using a sequence comparison algorithm or by visual inspection.

The "percent sequence identity" ("% identity") of a subject sequence to a reference (i.e. query) sequence means that the subject sequence is identical (i.e., on an amino acid-by-amino acid basis for a polypeptide sequence, or a nucleotide-by-nucleotide basis for a polynucleotide sequence) by a specified percentage to the query sequence over a comparison length.

Site Directed Mutagenesis to Create the Polypeptides of the Invention

The polypeptides of the present invention can be engineered using any standard method of site-directed mutagenesis. The nucleic acid sequences corresponding to the polypeptides of the invention are synthetized using specific oligonucleotide primers and a high fidelity DNA polymerase. The target sequence is contained on a double stranded plasmid isolated from a methylation-competent *E. coli* strain. Complimentary oligonucleotides containing the desired mutation are synthesized and purified using polyacrylamide gel electrophoresis. A thermal cycler is used to control the temperature for alternating cycles of denaturation of the double stranded plasmid template (94° C. for 30 seconds), annealing of the oligonucleotide primers (55° C. for 1 minute), and extension of the primers with a high fidelity polymerase (68° C. for 1 minute/kb of plasmid length). After approximately 15 cycles, the mixture of newly synthetized and input DNA are treated with a restriction enzyme specific for methylated residues (Dpn I) to digest the parental plasmid. The resulting DNA is introduced into chemically or electrically competent bacterial strains for screening and isolation of plasmids containing the desired mutation. Plasmid DNA is isolated from the transformants and screened via fluorescent dye-terminator sequencing to confirm the mutant sequence.

Bulk Drug Product Expression, Fermentation, and Purification

An *E. coli* strain containing a lysogen of λDE3, and therefore carrying a chromosomal copy of the T7 RNA polymerase gene under the control of the lacUV5 promoter, is transformed with a bacterial expression vector containing an IPTG-inducible promoter encoding a nucleic acid sequence corresponding to one or more of the polypeptides of the present invention. Cultures are grown in luria broth medium supplemented with 34 µg/mL chloroamphenicol and 15 µg/mL kanamycin at 37° C. When the OD600 reaches >0.4, the temperature is reduced to 18° C. and the cells are induced with 0.5 mM IPTG for 17 hours. The bacterial cells are then resuspended in buffer containing 50 mM $NaH_2PO_4$, pH 8, 300 mM NaCl, 20 mM imidazole, 10% glycerol, 0.1% NP40, 2 mM DTT and protease inhibitors (VWR), lysed in a Gaulin homogenizer, and centrifuged to remove cell debris before protein purification.

In one embodiment, purification of the polypeptides of the present invention can be achieved using a polyhistidine tag at the amino-terminus. A nickel column is used in affinity purifications of polyhistidine tags, with, for example, a 5 mL column being utilized for lysate generated by 4 L of *E. coli*. The lysate is loaded onto the column and then washed with Buffer A (50 mM $NaH_2PO_4$, 300 mM NaCl, 30% glycerol, 20 mM imidazole, 2 mM DTT at pH 7.5). A step elution to 7% Buffer B (50 mM $NaH_2PO_4$, 300 mM NaCl, 30% glycerol, 2 M imidazole, 2 mM DTT at pH 6.8), for 3.2 column volumes is then carried out. A gradient to 100% Buffer B over 3 column volumes is then carried out. The polypeptide of the present invention can then be gel-filtered into Buffer C (50 mM $NaH_2PO_4$, 150 mM NaCl, 40% glycerol, 1 mM EDTA, 2 mM DTT at pH 6.8) and loaded onto a cation exchange column for further purification. After the protein is loaded, the column is washed with Buffer C followed by a step elution to 75% of Buffer D (50 mM $NaH_2PO_4$, 1 M NaCl, 40% glycerol, 1 mM EDTA, 2 mM DTT at pH 6.8), then a 5 column volume gradient to 100% Buffer D. The protein is then gel filtered into Buffer E (50 mM $NaH_2PO4$, 300 mM NaCl, 40% glycerol, 1 mM EDTA, 2 mM DTT at pH 6.8) and stored at −20° C.

Different embodiments of the polypeptides of the invention, including but not limited to: those lacking a polyhistidine tag, those possessing a polyarginine tag, those with reduced cysteine content, those with amino acid sequence variations designed to make the drug candidate more thermally stable, those with modifications to enhance or reduce a particular activity of the drug candidate, may require alternative purification strategies. Embodiments of the polypeptide drug candidate lacking a polyhistidine tag, for example, may be directly applied to a cation exchange column. Additional steps, for example the use of hydrophobic interaction chromatography, may be utilized by taking the protein in Buffer F (50 mM $NaH_2PO_4$, 300 mM NaCl, 1 M $(NH_4)_2SO_4$, 30% glycerol, 1 mM EDTA, 2 mM DTT at pH 6.8) and running a 10 column volume gradient to 100% Buffer E. Other affinity columns or sizing columns may be used to purify different embodiments of the polypeptide drug candidates.

Alternative techniques may also be used for exchange of buffers, concentration of the drug candidates and purification of the drug candidates. These could include, but are not limited to, ultrafiltration, tangential flow filtration and diafiltration for the concentration of the drug candidate and for exchange of buffers. Techniques such a precipitation of the drug candidates by $(NH_4)_2SO_4$ or some other chemical agent may also be used. Denaturing the drug candidate in urea or some other denaturant and refolding it may also be used.

The polypeptides of the present invention are stabilized by excipients containing salts; solutions stable at 300 mM NaCl can begin to precipitate at 150 mM NaCl. For this reason excipient mixtures will favor these stabilizing salt concentrations, which could include but are not limited to sodium phosphate, sodium chloride, calcium chloride, and magnesium chloride.

The addition of amino acid-based excipients such as arginine have proven to be stabilizing to the polypeptides of the present invention. A 10% solution of sucrose allows the polypeptides of the invention to be stable at 1 mg/mL, the addition of 2% w/v arginine allows some embodiments of the polypeptides to be stable at 3 mg/mL. For this reason, other amino acid based compounds, including but not limited to histidine, glutamine, glycine and human albumin, may be used as excipients.

The addition of excipients such as glycerol is stabilizing to polypeptides of the present invention. For example, in one embodiment, a polypeptide has a maximum concentration with 10% glycerol (v/v) of 1 mg/mL; while at 40% glycerol, the drug candidates are stable up to 12 mg/mL. Excipient mixtures containing compounds with similar chemical properties are envisioned that include but are not limited to polyols such as mannitol, xylitol and sorbitol. Disaccharides such as sucrose have been found to be stabilizing at 10% w/v; other disaccharides including but not limited to maltose and trehalose can also be used. Monosaccharides can also be used in the present invention. Polysorbates, polyethyleneglycols and similar compounds can also be used to practice the present invention.

As one skilled in the art will recognize, the use of antioxidants and preservatives may also be used to ensure stability of the polypeptides during storage. Antioxidants, including but not limited to sodium citrate, may be stabilizing for long term storage of the polypeptides of the invention. Preservatives, including but not limited to, benzyl alcohol may also be stabilizing to the polypeptides during storage and may be used in final excipient mixtures.

Measurement of Oligoadenylate Synthetase Activity of Polypeptides

The oligoadenylate synthetase activities of the polypeptides of the invention are measured according to previously published methods (Justesen, J., et al. Nuc Acids Res. 8:3073-3085, 1980). Briefly, protein is activated with 200 µg/ml polyinosinic:polycytidylic acid in buffer containing 20 mM Tris-HCl, pH 7.8, 50 mM Mg(OAc)$_2$, 1 mM DTT, 0.2 mM EDTA, 2.5 mM ATP, α[$^{32}$P]ATP, 0.5 mg/ml BSA, and 10% glycerol. The reaction proceeds at 37° C. for 30 minutes to 24 hours and is terminated by heating to 90° C. for 3 minutes. 2-4 µl of the reaction mixture is spotted onto a PEI-cellulose thin layer plate. After drying, the plate is developed with 0.4 M Tris-HCl, 30 mM MgCl$_2$, pH 8.7. The plate is dried and visualized by phosphorimager analysis. Alternatively, the reaction mixture can be further incubated with 0.05 U/µl calf intestinal phosphatase to remove the terminal phosphate. Thin layer chromatographic separation is achieved using a 0.76 M KH$_2$PO$_4$, pH 3.6 developing buffer system. The plate is then dried and visualized by phosphorimager analysis.

Measurement of Antiviral Activity of Polypeptides

The ability of the polypeptides of the present invention to protect cultured cells from cytotoxic viruses is demonstrated using a murine encephalomyocarditis virus (EMCV, ATCC strain VR-129B) infection model. Other in vitro virus infection models include but are not limited to flaviviruses such as bovine diarrheal virus, West Nile Virus, and GBV-C virus, other RNA viruses such as respiratory syncytial virus, and the HCV replicon systems (e.g. Blight, K. J., et al. 2002. J. Virology, 76:13001-13014). Any appropriate cultured cell competent for viral replication can be utilized in the antiviral assays.

Human Huh7 hepatoma cells are seeded at a density of 1×10$^4$ cells/well in 96 well culture plates and incubated overnight in complete medium (DMEM containing 10% fetal bovine serum). The following morning, the media is replaced with complete medium containing 0-10 µM protein or equivalent amounts of protein dilution buffer. When desired, alpha-interferon is added at a concentration of 100 IU/ml. Cells are pretreated for 2-8 hours preceding viral infection. After pretreatment, an equal volume of medium containing dilutions of EMC virus in complete medium is added to the wells. In the experiments described herein, a range of 50-500 plaque forming units (pfu) is added per well.

Viral infection is allowed to proceed overnight (approximately 18 hours), and the proportion of viable cells is calculated using any available cell viability or cytotoxicity reagents. The results described herein are obtained using a cell viability assay that measures conversion of a tetrazolium compound [3-(4,5-dimethyl-2-yl)-5-(3-carboxymethoxyphenyl)-2-(4-sulfophenyl)-2H-tetrazolium, inner salt; MTS] to a colored formazan compound in viable cells. The conversion of MTS to formazan is detected in a 96-well plate reader at an absorbance of 492 nm. The resulting optical densities either are plotted directly to estimate cell viability or are normalized by control-treated samples to calculate a percentage of viable cells after treatment.

Polypeptide Pegylation; Sulfhydryl

Conjugation of polyethylene glycol (PEG) to the polypeptides of the invention was achieved by mixing diothiothreitol (DTT)-free purified polypeptide with activated mPEG-MAL (Nektar Therapeutics) at a 0.5-10:1 molar ratio. The reaction proceeded at room temperature for 5 min-2 hours and was quenched by the addition of 2 mM DTT. Conjugation occurred at multiple cysteine sites using linear 20 kDa and branched 40 kDa PEGs (FIGS. 6A and 6B). Non-pegylated forms and forms containing one or more PEG can be separated from each other using a variety of chromatographic methodologies as known to those skilled in the art. In exemplary embodiments of the present invention, ion exchange columns, hydrophobic interactions columns, gel filtration and size exclusion chromatography, each alone or in combination with one another, can be utilized for isolation of the different PEG forms.

Polypeptide Pegylation; N-Terminal

Polypeptides of the invention can be pegylated at the N-terminal amine. To polypeptides in 50 mM NaH$_2$PO$_4$, 300 mM NaCl, 30% glycerol, 1 mM EDTA, 2 mM DTT at pH 5 containing 20 mM sodium cyanobororohydride and stirring in an ice bath are added a 5-fold excess of mPEG butyrALD-40K. The reaction is allowed to proceed for up to ten hours and then quenched by the addition of a 50-fold excess of glycine. Reaction products are analyzed by SDS-PAGE.

The following examples are offered by way of illustration, and not by way of limitation.

EXAMPLES

Example 1

Amino Acid Modifications in Non-Human Primate OAS1 Proteins

OAS1 genes from non-human primates were sequenced and compared with mutations found in the human OAS1 gene. Such mutations provide additional insight into evolution of the OAS1 gene and protein. Evolutionarily conserved amino acids suggest sites important, or critical, for OAS1 function or enzymatic activity. Conversely, OAS1 amino acid sites that have recently mutated, for example in humans only, or show a plurality of amino acid substitutions across primates, indicate sites less critical to function or enzymatic activity. The abundance of mutated sites within a particular motif of the OAS1 protein are correlated with the tolerance of that functional domain to modification. Such sites and motifs are optimized to improve protein function or specific activity. Similarly, mutations in genes and proteins with immune or viral defense functions like OAS1 are hypothesized to result from historical challenge by viral infection. Mutations in primate OAS1 proteins are hypothesized to improve antiviral efficacy on this basis and are opportunities for optimization of a human therapeutic OAS1 protein.

In an exemplary embodiment, the ancestral primate amino acid for a specific site within OAS1 may be restored to a human therapeutic form of the OAS1 protein to optimize protein specific activity or anti-viral efficacy. In other embodiments, alternative amino acids identified in non-human primate OAS1s, but not necessarily ancestrally conserved, are substituted into a human therapeutic form of OAS1 in order to improve protein specific activity or antiviral efficacy. DNA and mRNA sequences that code for both the native primate proteins as well as primate-human hybrid forms are novel and have utility. Several examples of their utility are: as agents to detect their respective DNA or mRNA counterparts; in expression vectors used in the manufacture of therapeutic proteins; and in the detection of novel compounds that bind the respective mRNA.

FIG. 1 provides a therapeutic form of OAS1 (SEQ ID NO:1). Modifications to this form in order to provide additional therapeutic forms is performed using at least one amino acid modification as provided in FIG. 2. As described in FIG. 2, a useful modification is the removal of the initial methionine from SEQ ID NO:1 and other forms of OAS1. Additional modifications are made as indicated in FIG. 3. The foregoing modifications described in FIGS. 2 and 3 are also applied to other therapeutic OAS1 isoforms provided in FIG. 5. FIG. 3 also provides specific modifications of OAS1 proteins that are carboxyl-terminus homologous to Genbank accession NP_002525.1 (for example, SEQ ID NO:3), specific modifications of OAS1 proteins that are carboxyl-terminus homologous to Genbank accession NP_0058132.1 (for example, SEQ ID NO:2) and specific modifications of OAS1 proteins that are carboxyl-terminus homologous to Genbank accession NP_001027581.1 (for example, SEQ ID NO:4). Listed in FIG. 4 are exemplary mutations identified in non-human primates including gorilla, chimpanzee, orangutan, and macaque. FIG. 5 lists additional human and non-human primate OAS1 isoforms that are useful for the diagnostic and therapeutic purposes of the present invention as well as particular primate mutations described by the present invention.

Example 2

Preparation and Sequencing of cDNA

Total cellular RNA is purified from cultured lymphoblasts or fibroblasts from the patients having the hepatitis C resistance phenotype. The purification procedure is performed as described by Chomczynski, et al., Anal. Biochem., 162:156-159 (1987). The cells are homogenized in 10 milliliters (ml) of a denaturing solution containing 4.0M guanidine thiocyanate, 0.1M Tris-HCl at pH 7.5, and 0.1M beta-mercaptoethanol to form a cell lysate. Sodium lauryl sarcosinate is then admixed to a final concentration of 0.5% to the cell lysate after which the admixture was centrifuged at 5000×g for 10 minutes at room temperature. The resultant supernatant containing the total RNA is layered onto a cushion of 5.7M cesium chloride and 0.01M EDTA at pH 7.5 and is pelleted by centrifugation. The resultant RNA pellet is dissolved in a solution of 10 mM Tris-HCl at pH 7.6 and 1 mM EDTA (TE) containing 0.1% sodium docecyl sulfate (SDS). After phenolchloroform extraction and ethanol precipitation, the purified total cellular RNA concentration is estimated by measuring the optical density at 260 nm.

Total RNA prepared above is used as a template for cDNA synthesis using reverse transcriptase for first strand synthesis and PCR with oligonucleotide primers designed so as to amplify the cDNA in two overlapping fragments designated the 5' and the 3' fragment. The oligonucleotides used in practicing this invention are synthesized on an Applied Biosystems 381A DNA Synthesizer following the manufacturer's instructions. PCR is conducted using methods known in the art. PCR amplification methods are described in detail in U.S. Pat. Nos. 4,683,192, 4,683,202, 4,800,159, and 4,965,188, and at least in several texts including PCR Technology: Principles and Applications for DNA Amplification, H. Erlich, ed., Stockton Press, New York (1989); and PCR Protocols: A Guide to Methods and Applications, Innis, et al., eds., Academic Press, San Diego, Calif. (1990) and primers based on the nucleotide sequences encoding the amino acid modified regions as disclosed herein.

The sequences determined directly from the PCR-amplified DNAs from the patients with and without HCV infection, are analyzed. The presence of a mutation upstream from the coding region of the OAS gene can be detected in patients who are seronegative for HCV despite repeated exposures to the virus.

The foregoing specification, including the specific embodiments and examples, is intended to be illustrative of the present invention and is not to be taken as limiting. Numerous other variations and modifications can be effected without departing from the true spirit and scope of the invention. All patents, patent publications, and non-patent publications cited are incorporated by reference herein.

What is claimed is:

1. An oligoadenylate synthetase 1 protein consisting of a polypeptide that has the amino acid sequence of SEQ ID NO:1 except (a) the amino acid at position 1 is deleted, (b) the amino acid at position 162 is Gly, and (c) there is an amino acid substitution at position 104.

2. The protein of claim 1 wherein the amino acid at position 104 is Lys.

3. A therapeutic composition for treating infection by a virus in a mammal wherein said composition comprises a pharmaceutically acceptable carrier and an oligoadenylate synthetase 1 protein consisting of a polypeptide that has the amino acid sequence of SEQ ID NO:1 except (a) the amino acid at position 1 is deleted, (b) the amino acid at position 162 is Gly, and (c) there is an amino acid substitution at position 104.

4. An oligoadenylate synthetase 1 protein consisting of a polypeptide that has the amino acid sequence of SEQ ID NO:1 except (a) the amino acid at position 1 is deleted, (b) the amino acid at position 162 is Gly, (c) there is an amino acid substitution at position 104, and (d) there is an amino acid substitution at a position selected from the group consisting of position 31, 115, 127, 295 and 315.

5. The composition of claim 3 wherein the amino acid at position 104 is Lys.

6. The therapeutic composition of claim 3 wherein the virus is a flavivirus.

7. The therapeutic composition of claim 3 wherein the virus is hepatitis C virus.

8. A kit comprising the therapeutic composition of claim 3.

9. The kit of claim 8 further comprising instructions in a form prescribed by a governmental agency that regulates the manufacture, use or sale of pharmaceuticals or biological products.

10. A therapeutic composition for treating infection by a virus in a mammal wherein said composition comprises a pharmaceutically acceptable carrier and an oligoadenylate synthetase 1 protein consisting of a polypeptide that has the amino acid sequence of SEQ ID NO:1 except (a) the amino acid at position 1 is deleted, (b) the amino acid at position 162 is Gly, (c) there is an amino acid substitution at position 104, and (d) there is an amino acid substitution at a position selected from the group consisting of position 31, 115, 127, 295 and 315.

* * * * *

SEQUENCE LISTING

```
<160> NUMBER OF SEQ ID NOS: 16

<210> SEQ ID NO 1
<211> LENGTH: 346
<212> TYPE: PRT
<213> ORGANISM: Homo sapiens

<400> SEQUENCE: 1

Met Met Asp Leu Arg Asn Thr Pro Ala Lys Ser Leu Asp Lys Phe Ile
 1               5                  10                  15

Glu Asp Tyr Leu Leu Pro Asp Thr Cys Phe Arg Met Gln Ile Asn His
                20                  25                  30

Ala Ile Asp Ile Ile Cys Gly Phe Leu Lys Glu Arg Cys Phe Arg Gly
            35                  40                  45

Ser Ser Tyr Pro Val Cys Val Ser Lys Val Val Lys Gly Gly Ser Ser
        50                  55                  60

Gly Lys Gly Thr Thr Leu Arg Gly Arg Ser Asp Ala Asp Leu Val Val
 65                  70                  75                  80

Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Ala Cys Gln Arg Glu
                100                 105                 110

Arg Ala Phe Ser Val Lys Phe Glu Val Gln Ala Pro Arg Trp Gly Asn
            115                 120                 125
```

```
Pro Arg Ala Leu Ser Phe Val Leu Ser Ser Leu Gln Leu Gly Glu Gly
        130                 135                 140

Val Glu Phe Asp Val Leu Pro Ala Phe Asp Ala Leu Gly Gln Leu Thr
145                 150                 155                 160

Gly Ser Tyr Lys Pro Asn Pro Gln Ile Tyr Val Lys Leu Ile Glu Glu
                165                 170                 175

Cys Thr Asp Leu Gln Lys Glu Gly Glu Phe Ser Thr Cys Phe Thr Glu
                180                 185                 190

Leu Gln Arg Asp Phe Leu Lys Gln Arg Pro Thr Lys Leu Lys Ser Leu
            195                 200                 205

Ile Arg Leu Val Lys His Trp Tyr Gln Asn Cys Lys Lys Leu Gly
        210                 215                 220

Lys Leu Pro Pro Gln Tyr Ala Leu Glu Leu Leu Thr Val Tyr Ala Trp
225                 230                 235                 240

Glu Arg Gly Ser Met Lys Thr His Phe Asn Thr Ala Gln Gly Phe Arg
                245                 250                 255

Thr Val Leu Glu Leu Val Ile Asn Tyr Gln Gln Leu Cys Ile Tyr Trp
                260                 265                 270

Thr Lys Tyr Tyr Asp Phe Lys Asn Pro Ile Ile Glu Lys Tyr Leu Arg
            275                 280                 285

Arg Gln Leu Thr Lys Pro Arg Pro Val Ile Leu Asp Pro Ala Asp Pro
        290                 295                 300

Thr Gly Asn Leu Gly Gly Asp Pro Lys Gly Trp Arg Gln Leu Ala
305                 310                 315                 320

Gln Glu Ala Glu Ala Trp Leu Asn Tyr Pro Cys Phe Lys Asn Trp Asp
                325                 330                 335

Gly Ser Pro Val Ser Ser Trp Ile Leu Leu
                340                 345

<210> SEQ ID NO 2
<211> LENGTH: 400
<212> TYPE: PRT
<213> ORGANISM: Homo sapiens

<400> SEQUENCE: 2

Met Met Asp Leu Arg Asn Thr Pro Ala Lys Ser Leu Asp Lys Phe Ile
1               5                   10                  15

Glu Asp Tyr Leu Leu Pro Asp Thr Cys Phe Arg Met Gln Ile Asn His
                20                  25                  30

Ala Ile Asp Ile Ile Cys Gly Phe Leu Lys Glu Arg Cys Phe Arg Gly
            35                  40                  45

Ser Ser Tyr Pro Val Cys Val Ser Lys Val Val Lys Gly Gly Ser Ser
50                  55                  60

Gly Lys Gly Thr Thr Leu Arg Gly Arg Ser Asp Ala Asp Leu Val Val
65                  70                  75                  80

Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Ala Cys Gln Arg Glu
                100                 105                 110

Arg Ala Phe Ser Val Lys Phe Glu Val Gln Ala Pro Arg Trp Gly Asn
            115                 120                 125

Pro Arg Ala Leu Ser Phe Val Leu Ser Ser Leu Gln Leu Gly Glu Gly
        130                 135                 140

Val Glu Phe Asp Val Leu Pro Ala Phe Asp Ala Leu Gly Gln Leu Thr
145                 150                 155                 160
```

```
Gly Gly Tyr Lys Pro Asn Pro Gln Ile Tyr Val Lys Leu Ile Glu Glu
                165                 170                 175
Cys Thr Asp Leu Gln Lys Glu Gly Glu Phe Ser Thr Cys Phe Thr Glu
            180                 185                 190
Leu Gln Arg Asp Phe Leu Lys Gln Arg Pro Thr Lys Leu Lys Ser Leu
        195                 200                 205
Ile Arg Leu Val Lys His Trp Tyr Gln Asn Cys Lys Lys Leu Gly
    210                 215                 220
Lys Leu Pro Pro Gln Tyr Ala Leu Glu Leu Leu Thr Val Tyr Ala Trp
225                 230                 235                 240
Glu Arg Gly Ser Met Lys Thr His Phe Asn Thr Ala Gln Gly Phe Arg
                245                 250                 255
Thr Val Leu Glu Leu Val Ile Asn Tyr Gln Gln Leu Cys Ile Tyr Trp
            260                 265                 270
Thr Lys Tyr Tyr Asp Phe Lys Asn Pro Ile Ile Glu Lys Tyr Leu Arg
        275                 280                 285
Arg Gln Leu Thr Lys Pro Arg Pro Val Ile Leu Asp Pro Ala Asp Pro
    290                 295                 300
Thr Gly Asn Leu Gly Gly Gly Asp Pro Lys Gly Trp Arg Gln Leu Ala
305                 310                 315                 320
Gln Glu Ala Glu Ala Trp Leu Asn Tyr Pro Cys Phe Lys Asn Trp Asp
                325                 330                 335
Gly Ser Pro Val Ser Ser Trp Ile Leu Leu Ala Glu Ser Asn Ser Ala
            340                 345                 350
Asp Asp Glu Thr Asp Asp Pro Arg Arg Tyr Gln Lys Tyr Gly Tyr Ile
        355                 360                 365
Gly Thr His Glu Tyr Pro His Phe Ser His Arg Pro Ser Thr Leu Gln
    370                 375                 380
Ala Ala Ser Thr Pro Gln Ala Glu Glu Asp Trp Thr Cys Thr Ile Leu
385                 390                 395                 400

<210> SEQ ID NO 3
<211> LENGTH: 364
<212> TYPE: PRT
<213> ORGANISM: Homo sapiens

<400> SEQUENCE: 3

Met Met Asp Leu Arg Asn Thr Pro Ala Lys Ser Leu Asp Lys Phe Ile
1               5                   10                  15
Glu Asp Tyr Leu Leu Pro Asp Thr Cys Phe Arg Met Gln Ile Asn His
            20                  25                  30
Ala Ile Asp Ile Ile Cys Gly Phe Leu Lys Glu Arg Cys Phe Arg Gly
        35                  40                  45
Ser Ser Tyr Pro Val Cys Val Ser Lys Val Val Lys Gly Gly Ser Ser
    50                  55                  60
Gly Lys Gly Thr Thr Leu Arg Gly Arg Ser Asp Ala Asp Leu Val Val
65                  70                  75                  80
Phe Leu Ser Pro Leu Thr Thr Phe Gln Asp Gln Leu Asn Arg Arg Gly
                85                  90                  95
Glu Phe Ile Gln Glu Ile Arg Arg Gln Leu Glu Ala Cys Gln Arg Glu
            100                 105                 110
Arg Ala Phe Ser Val Lys Phe Glu Val Gln Ala Pro Arg Trp Gly Asn
        115                 120                 125
Pro Arg Ala Leu Ser Phe Val Leu Ser Ser Leu Gln Leu Gly Glu Gly
```

```
                    130                 135                 140
Val Glu Phe Asp Val Leu Pro Ala Phe Asp Ala Leu Gly Gln Leu Thr
145                 150                 155                 160

Gly Gly Tyr Lys Pro Asn Pro Gln Ile Tyr Val Lys Leu Ile Glu Glu
                165                 170                 175

Cys Thr Asp Leu Gln Lys Glu Gly Glu Phe Ser Thr Cys Phe Thr Glu
                180                 185                 190

Leu Gln Arg Asp Phe Leu Lys Gln Arg Pro Thr Lys Leu Lys Ser Leu
                195                 200                 205

Ile Arg Leu Val Lys His Trp Tyr Gln Asn Cys Lys Lys Lys Leu Gly
                210                 215                 220

Lys Leu Pro Pro Gln Tyr Ala Leu Glu Leu Leu Thr Val Tyr Ala Trp
225                 230                 235                 240

Glu Arg Gly Ser Met Lys Thr His Phe Asn Thr Ala Gln Gly Phe Arg
                245                 250                 255

Thr Val Leu Glu Leu Val Ile Asn Tyr Gln Gln Leu Cys Ile Tyr Trp
                260                 265                 270

Thr Lys Tyr Tyr Asp Phe Lys Asn Pro Ile Ile Glu Lys Tyr Leu Arg
                275                 280                 285

Arg Gln Leu Thr Lys Pro Arg Pro Val Ile Leu Asp Pro Ala Asp Pro
                290                 295                 300

Thr Gly Asn Leu Gly Gly Gly Asp Pro Lys Gly Trp Arg Gln Leu Ala
305                 310                 315                 320

Gln Glu Ala Glu Ala Trp Leu Asn Tyr Pro Cys Phe Lys Asn Trp Asp
                325                 330                 335

Gly Ser Pro Val Ser Ser Trp Ile Leu Leu Val Arg Pro Pro Ala Ser
                340                 345                 350

Ser Leu Pro Phe Ile Pro Ala Pro Leu His Glu Ala
                355                 360

<210> SEQ ID NO 4
<211> LENGTH: 414
<212> TYPE: PRT
<213> ORGANISM: Homo sapiens

<400> SEQUENCE: 4

Met Met Asp Leu Arg Asn Thr Pro Ala Lys Ser Leu Asp Lys Phe Ile
1               5                   10                  15

Glu Asp Tyr Leu Leu Pro Asp Thr Cys Phe Arg Met Gln Ile Asn His
                20                  25                  30

Ala Ile Asp Ile Ile Cys Gly Phe Leu Lys Glu Arg Cys Phe Arg Gly
                35                  40                  45

Ser Ser Tyr Pro Val Cys Val Ser Lys Val Val Lys Gly Gly Ser Ser
                50                  55                  60

Gly Lys Gly Thr Thr Leu Arg Gly Arg Ser Asp Ala Asp Leu Val Val
65                  70                  75                  80

Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Ala Cys Gln Arg Glu
                100                 105                 110

Arg Ala Phe Ser Val Lys Phe Glu Val Gln Ala Pro Arg Trp Gly Asn
                115                 120                 125

Pro Arg Ala Leu Ser Phe Val Leu Ser Ser Leu Gln Leu Gly Glu Gly
                130                 135                 140
```

```
Val Glu Phe Asp Val Leu Pro Ala Phe Asp Ala Leu Gly Gln Leu Thr
145                 150                 155                 160

Gly Gly Tyr Lys Pro Asn Pro Gln Ile Tyr Val Lys Leu Ile Glu Glu
            165                 170                 175

Cys Thr Asp Leu Gln Lys Glu Gly Glu Phe Ser Thr Cys Phe Thr Glu
                180                 185                 190

Leu Gln Arg Asp Phe Leu Lys Gln Arg Pro Thr Lys Leu Lys Ser Leu
            195                 200                 205

Ile Arg Leu Val Lys His Trp Tyr Gln Asn Cys Lys Lys Leu Gly
210                 215                 220

Lys Leu Pro Pro Gln Tyr Ala Leu Glu Leu Leu Thr Val Tyr Ala Trp
225                 230                 235                 240

Glu Arg Gly Ser Met Lys Thr His Phe Asn Thr Ala Gln Gly Phe Arg
                245                 250                 255

Thr Val Leu Glu Leu Val Ile Asn Tyr Gln Gln Leu Cys Ile Tyr Trp
                260                 265                 270

Thr Lys Tyr Tyr Asp Phe Lys Asn Pro Ile Ile Glu Lys Tyr Leu Arg
            275                 280                 285

Arg Gln Leu Thr Lys Pro Arg Pro Val Ile Leu Asp Pro Ala Asp Pro
290                 295                 300

Thr Gly Asn Leu Gly Gly Gly Asp Pro Lys Gly Trp Arg Gln Leu Ala
305                 310                 315                 320

Gln Glu Ala Glu Ala Trp Leu Asn Tyr Pro Cys Phe Lys Asn Trp Asp
                325                 330                 335

Gly Ser Pro Val Ser Ser Trp Ile Leu Leu Thr Gln His Thr Pro Gly
                340                 345                 350

Ser Ile His Pro Thr Gly Arg Arg Gly Leu Asp Leu His His Pro Leu
                355                 360                 365

Asn Ala Ser Ala Ser Trp Gly Lys Gly Leu Gln Cys Tyr Leu Asp Gln
370                 375                 380

Phe Leu His Phe Gln Val Gly Leu Leu Ile Gln Arg Gly Gln Ser Ser
385                 390                 395                 400

Ser Val Ser Trp Cys Ile Ile Gln Asp Arg Thr Gln Val Ser
                405                 410

<210> SEQ ID NO 5
<211> LENGTH: 353
<212> TYPE: PRT
<213> ORGANISM: Gorilla gorilla

<400> SEQUENCE: 5

Met Met Asp Leu Arg Asn Thr Pro Ala Lys Ser Leu Asp Lys Phe Ile
1               5                   10                  15

Glu Asp Tyr Leu Leu Pro Asp Thr Cys Phe Arg Met Gln Ile Asn His
                20                  25                  30

Ala Ile Asp Ile Ile Cys Gly Phe Leu Lys Glu Arg Cys Phe Arg Gly
            35                  40                  45

Ser Ser Tyr Pro Val Cys Val Ser Lys Val Val Lys Gly Gly Ser Ser
        50                  55                  60

Gly Lys Gly Thr Ala Leu Arg Gly Arg Ser Asp Ala Asp Leu Val Val
65                  70                  75                  80

Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Ala Cys Gln Arg Glu
                100                 105                 110
```

```
Arg Ala Phe Ser Val Lys Phe Glu Val Gln Ala Pro Arg Trp Gly Asn
            115                 120                 125

Pro Cys Ala Leu Ser Phe Val Leu Ser Ser Leu Gln Leu Gly Glu Gly
130                 135                 140

Val Glu Phe Asp Val Leu Pro Ala Phe Asp Ala Leu Gly Gln Leu Thr
145                 150                 155                 160

Gly Gly Tyr Lys Pro Asn Pro Gln Ile Tyr Val Lys Leu Ile Lys Glu
                165                 170                 175

Cys Thr Tyr Leu Gln Lys Glu Gly Glu Phe Ser Thr Cys Phe Thr Glu
            180                 185                 190

Leu Gln Arg Asp Phe Leu Lys Gln Arg Pro Thr Lys Leu Lys Ser Leu
        195                 200                 205

Ile Arg Leu Val Lys His Trp Tyr Gln Asn Cys Lys Lys Lys Leu Gly
    210                 215                 220

Lys Leu Pro Pro Gln Tyr Ala Leu Glu Leu Leu Thr Val Tyr Ala Trp
225                 230                 235                 240

Glu Gln Gly Ser Met Lys Thr His Phe Asn Thr Ala Gln Gly Phe Arg
                245                 250                 255

Thr Val Leu Glu Leu Val Ile Asn Tyr Gln Gln Leu Cys Ile Tyr Trp
            260                 265                 270

Thr Lys Tyr Tyr Asp Phe Lys Asn Pro Ile Ile Glu Lys Tyr Leu Arg
        275                 280                 285

Arg Gln Leu Arg Lys Pro Arg Pro Val Ile Leu Asp Pro Ala Asp Pro
    290                 295                 300

Thr Gly Asn Leu Gly Gly Gly Asp Pro Lys Gly Trp Arg Gln Leu Ala
305                 310                 315                 320

Gln Glu Ala Glu Ala Trp Leu Asn Tyr Pro Cys Phe Lys Asn Trp Asp
                325                 330                 335

Gly Ser Pro Val Ser Ser Trp Ile Leu Leu Ala Glu Ser Asp Ser Gly
            340                 345                 350

Arg

<210> SEQ ID NO 6
<211> LENGTH: 364
<212> TYPE: PRT
<213> ORGANISM: Gorilla gorilla

<400> SEQUENCE: 6

Met Met Asp Leu Arg Asn Thr Pro Ala Lys Ser Leu Asp Lys Phe Ile
1               5                   10                  15

Glu Asp Tyr Leu Leu Pro Asp Thr Cys Phe Arg Met Gln Ile Asn His
            20                  25                  30

Ala Ile Asp Ile Ile Cys Gly Phe Leu Lys Glu Arg Cys Phe Arg Gly
        35                  40                  45

Ser Ser Tyr Pro Val Cys Val Ser Lys Val Val Lys Gly Gly Ser Ser
    50                  55                  60

Gly Lys Gly Thr Ala Leu Arg Gly Arg Ser Asp Ala Asp Leu Val Val
65                  70                  75                  80

Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Ala Cys Gln Arg Glu
            100                 105                 110

Arg Ala Phe Ser Val Lys Phe Glu Val Gln Ala Pro Arg Trp Gly Asn
        115                 120                 125
```

```
Pro Cys Ala Leu Ser Phe Val Leu Ser Ser Leu Gln Leu Gly Glu Gly
        130                 135                 140

Val Glu Phe Asp Val Leu Pro Ala Phe Asp Ala Leu Gly Gln Leu Thr
145                 150                 155                 160

Gly Gly Tyr Lys Pro Asn Pro Gln Ile Tyr Val Lys Leu Ile Lys Glu
                165                 170                 175

Cys Thr Tyr Leu Gln Lys Glu Gly Glu Phe Ser Thr Cys Phe Thr Glu
                180                 185                 190

Leu Gln Arg Asp Phe Leu Lys Gln Arg Pro Thr Lys Leu Lys Ser Leu
            195                 200                 205

Ile Arg Leu Val Lys His Trp Tyr Gln Asn Cys Lys Lys Leu Gly
        210                 215                 220

Lys Leu Pro Pro Gln Tyr Ala Leu Glu Leu Leu Thr Val Tyr Ala Trp
225                 230                 235                 240

Glu Gln Gly Ser Met Lys Thr His Phe Asn Thr Ala Gln Gly Phe Arg
                245                 250                 255

Thr Val Leu Glu Leu Val Ile Asn Tyr Gln Gln Leu Cys Ile Tyr Trp
                260                 265                 270

Thr Lys Tyr Tyr Asp Phe Lys Asn Pro Ile Ile Glu Lys Tyr Leu Arg
            275                 280                 285

Arg Gln Leu Arg Lys Pro Arg Pro Val Ile Leu Asp Pro Ala Asp Pro
        290                 295                 300

Thr Gly Asn Leu Gly Gly Asp Pro Lys Gly Trp Arg Gln Leu Ala
305                 310                 315                 320

Gln Glu Ala Glu Ala Trp Leu Asn Tyr Pro Cys Phe Lys Asn Trp Asp
                325                 330                 335

Gly Ser Pro Val Ser Ser Trp Ile Leu Leu Val Arg Pro Pro Ala Ser
                340                 345                 350

Ser Leu Pro Phe Ile Pro Ala Pro Leu His Lys Ala
            355                 360

<210> SEQ ID NO 7
<211> LENGTH: 414
<212> TYPE: PRT
<213> ORGANISM: Gorilla gorilla

<400> SEQUENCE: 7

Met Met Asp Leu Arg Asn Thr Pro Ala Lys Ser Leu Asp Lys Phe Ile
1               5                   10                  15

Glu Asp Tyr Leu Leu Pro Asp Thr Cys Phe Arg Met Gln Ile Asn His
                20                  25                  30

Ala Ile Asp Ile Ile Cys Gly Phe Leu Lys Glu Arg Cys Phe Arg Gly
            35                  40                  45

Ser Ser Tyr Pro Val Cys Val Ser Lys Val Val Lys Gly Gly Ser Ser
        50                  55                  60

Gly Lys Gly Thr Ala Leu Arg Gly Arg Ser Asp Ala Asp Leu Val Val
65                  70                  75                  80

Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Ala Cys Gln Arg Glu
                100                 105                 110

Arg Ala Phe Ser Val Lys Phe Glu Val Gln Ala Pro Arg Trp Gly Asn
            115                 120                 125

Pro Cys Ala Leu Ser Phe Val Leu Ser Ser Leu Gln Leu Gly Glu Gly
```

```
        130                 135                 140
Val Glu Phe Asp Val Leu Pro Ala Phe Asp Ala Leu Gly Gln Leu Thr
145                 150                 155                 160

Gly Gly Tyr Lys Pro Asn Pro Gln Ile Tyr Val Lys Leu Ile Lys Glu
                165                 170                 175

Cys Thr Tyr Leu Gln Lys Glu Gly Glu Phe Ser Thr Cys Phe Thr Glu
            180                 185                 190

Leu Gln Arg Asp Phe Leu Lys Gln Arg Pro Thr Lys Leu Lys Ser Leu
        195                 200                 205

Ile Arg Leu Val Lys His Trp Tyr Gln Asn Cys Lys Lys Lys Leu Gly
    210                 215                 220

Lys Leu Pro Pro Gln Tyr Ala Leu Glu Leu Leu Thr Val Tyr Ala Trp
225                 230                 235                 240

Glu Gln Gly Ser Met Lys Thr His Phe Asn Thr Ala Gln Gly Phe Arg
                245                 250                 255

Thr Val Leu Glu Leu Val Ile Asn Tyr Gln Gln Leu Cys Ile Tyr Trp
            260                 265                 270

Thr Lys Tyr Tyr Asp Phe Lys Asn Pro Ile Ile Glu Lys Tyr Leu Arg
        275                 280                 285

Arg Gln Leu Lys Lys Pro Arg Pro Val Ile Leu Asp Pro Ala Asp Pro
    290                 295                 300

Thr Gly Asn Leu Gly Gly Gly Asp Pro Lys Gly Trp Arg Gln Leu Ala
305                 310                 315                 320

Gln Glu Ala Glu Ala Trp Leu Asn Tyr Pro Cys Phe Lys Asn Trp Asp
                325                 330                 335

Gly Ser Pro Val Ser Ser Trp Ile Leu Leu Thr Gln His Thr Pro Gly
            340                 345                 350

Ser Ile His Pro Thr Gly Arg Arg Gly Leu Asp Leu His His Pro Leu
        355                 360                 365

Asn Ala Ser Ala Ser Trp Gly Lys Gly Leu Gln Cys Tyr Leu Asp Gln
    370                 375                 380

Phe Leu His Phe Gln Val Gly Leu Leu Ile Gln Arg Gly Gln Ser Ser
385                 390                 395                 400

Ser Val Ser Trp Cys Ile Ile Gln Asp Arg Thr Gln Val Ser
                405                 410

<210> SEQ ID NO 8
<211> LENGTH: 401
<212> TYPE: PRT
<213> ORGANISM: Pan paniscus
<220> FEATURE:
<221> NAME/KEY: VARIANT
<222> LOCATION: 336
<223> OTHER INFORMATION: Xaa is Trp or Cys

<400> SEQUENCE: 8

Met Met Asp Leu Arg Asn Thr Pro Ala Lys Ser Leu Asp Lys Phe Ile
1               5                   10                  15

Glu Asp Tyr Leu Leu Pro Asp Thr Cys Phe Arg Thr Gln Ile Asn His
                20                  25                  30

Ala Ile Asp Ile Ile Cys Gly Phe Leu Lys Glu Arg Cys Phe Arg Gly
            35                  40                  45

Ser Ser Tyr Pro Val Cys Val Ser Lys Val Val Lys Gly Gly Ser Ser
        50                  55                  60

Gly Lys Gly Thr Thr Leu Arg Gly Arg Ser Asp Ala Asp Leu Val Val
65                  70                  75                  80
```

```
Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Val Cys Gln Arg Glu
            100                 105                 110

Glu Arg Ala Phe Ser Val Lys Phe Glu Val Gln Ala Pro Arg Trp Asp
        115                 120                 125

Asn Pro Arg Ala Leu Ser Phe Val Leu Ser Leu Gln Leu Gly Glu
    130                 135                 140

Gly Val Glu Phe Asp Val Leu Pro Ala Phe Asp Ala Leu Gly Gln Leu
145                 150                 155                 160

Ile Gly Gly Tyr Lys Pro Asp Pro Gln Ile Tyr Val Lys Leu Ile Glu
                165                 170                 175

Glu Cys Thr Tyr Leu Gln Lys Glu Gly Glu Phe Ser Thr Cys Phe Thr
            180                 185                 190

Glu Leu Gln Arg Asp Phe Leu Lys Glu Arg Pro Thr Lys Leu Lys Ser
        195                 200                 205

Leu Ile Arg Leu Val Lys His Trp Tyr Gln Asn Cys Lys Lys Lys Leu
    210                 215                 220

Gly Lys Leu Pro Pro Gln Tyr Ala Leu Glu Leu Leu Thr Val Tyr Ala
225                 230                 235                 240

Trp Glu Arg Gly Ser Met Lys Thr His Phe Asn Thr Ala Gln Gly Phe
                245                 250                 255

Arg Thr Val Leu Glu Leu Val Ile Asn Tyr Gln Gln Leu Cys Ile Tyr
            260                 265                 270

Trp Thr Lys Tyr Tyr Asp Phe Lys Asn Pro Ile Ile Glu Lys Tyr Leu
        275                 280                 285

Ser Arg Gln Leu Glu Lys Pro Arg Pro Val Ile Leu Asp Pro Ala Asp
    290                 295                 300

Pro Thr Gly Asn Leu Gly Gly Asp Pro Lys Gly Trp Arg Gln Leu
305                 310                 315                 320

Ala Gln Glu Ala Glu Ala Trp Leu Asn Tyr Pro Cys Phe Lys Asn Xaa
                325                 330                 335

Asp Gly Ser Pro Val Ser Ser Trp Ile Leu Leu Ala Glu Ser Asp Ser
            340                 345                 350

Ala Asp Asp Glu Thr Asp Asp Pro Arg Arg Tyr Gln Lys Tyr Gly Tyr
        355                 360                 365

Ile Gly Thr His Glu Tyr Pro His Phe Ser His Arg Pro Ser Thr Leu
    370                 375                 380

Gln Ala Ala Ser Ala Pro Gln Ala Glu Glu Asp Trp Thr Cys Thr Ile
385                 390                 395                 400

Leu

<210> SEQ ID NO 9
<211> LENGTH: 365
<212> TYPE: PRT
<213> ORGANISM: Pan paniscus
<220> FEATURE:
<221> NAME/KEY: VARIANT
<222> LOCATION: 336
<223> OTHER INFORMATION: Xaa is Trp or Cys

<400> SEQUENCE: 9

Met Met Asp Leu Arg Asn Thr Pro Ala Lys Ser Leu Asp Lys Phe Ile
1               5                   10                  15

Glu Asp Tyr Leu Leu Pro Asp Thr Cys Phe Arg Thr Gln Ile Asn His
```

```
            20                  25                  30
Ala Ile Asp Ile Ile Cys Gly Phe Leu Lys Glu Arg Cys Phe Arg Gly
        35                  40                  45

Ser Ser Tyr Pro Val Cys Val Ser Lys Val Val Lys Gly Gly Ser Ser
    50                  55                  60

Gly Lys Gly Thr Thr Leu Arg Gly Arg Ser Asp Ala Asp Leu Val Val
65                  70                  75                  80

Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Val Cys Gln Arg Glu
            100                 105                 110

Glu Arg Ala Phe Ser Val Lys Phe Glu Val Gln Ala Pro Arg Trp Asp
        115                 120                 125

Asn Pro Arg Ala Leu Ser Phe Val Leu Ser Ser Leu Gln Leu Gly Glu
    130                 135                 140

Gly Val Glu Phe Asp Val Leu Pro Ala Phe Asp Ala Leu Gly Gln Leu
145                 150                 155                 160

Ile Gly Gly Tyr Lys Pro Asp Pro Gln Ile Tyr Val Lys Leu Ile Glu
                165                 170                 175

Glu Cys Thr Tyr Leu Gln Lys Glu Gly Glu Phe Ser Thr Cys Phe Thr
            180                 185                 190

Glu Leu Gln Arg Asp Phe Leu Lys Glu Arg Pro Thr Lys Leu Lys Ser
        195                 200                 205

Leu Ile Arg Leu Val Lys His Trp Tyr Gln Asn Cys Lys Lys Lys Leu
    210                 215                 220

Gly Lys Leu Pro Pro Gln Tyr Ala Leu Glu Leu Leu Thr Val Tyr Ala
225                 230                 235                 240

Trp Glu Arg Gly Ser Met Lys Thr His Phe Asn Thr Ala Gln Gly Phe
                245                 250                 255

Arg Thr Val Leu Glu Leu Val Ile Asn Tyr Gln Gln Leu Cys Ile Tyr
            260                 265                 270

Trp Thr Lys Tyr Tyr Asp Phe Lys Asn Pro Ile Ile Glu Lys Tyr Leu
        275                 280                 285

Ser Arg Gln Leu Glu Lys Pro Arg Pro Val Ile Leu Asp Pro Ala Asp
    290                 295                 300

Pro Thr Gly Asn Leu Gly Gly Gly Asp Pro Lys Gly Trp Arg Gln Leu
305                 310                 315                 320

Ala Gln Glu Ala Glu Ala Trp Leu Asn Tyr Pro Cys Phe Lys Asn Xaa
                325                 330                 335

Asp Gly Ser Pro Val Ser Ser Trp Ile Leu Val Arg Pro Pro Ala
        340                 345                 350

Ser Ser Leu Pro Phe Ile Pro Ala Pro Leu His Glu Ala
    355                 360                 365

<210> SEQ ID NO 10
<211> LENGTH: 415
<212> TYPE: PRT
<213> ORGANISM: Pan paniscus
<220> FEATURE:
<221> NAME/KEY: VARIANT
<222> LOCATION: 336
<223> OTHER INFORMATION: Xaa is Trp or Cys

<400> SEQUENCE: 10

Met Met Asp Leu Arg Asn Thr Pro Ala Lys Ser Leu Asp Lys Phe Ile
1               5                   10                  15
```

```
Glu Asp Tyr Leu Leu Pro Asp Thr Cys Phe Arg Lys Gln Ile Asn His
            20                  25                  30

Ala Ile Asp Ile Ile Cys Gly Phe Leu Lys Glu Arg Cys Phe Arg Gly
        35                  40                  45

Ser Ser Tyr Pro Val Cys Val Ser Lys Val Val Lys Gly Gly Ser Ser
50                  55                  60

Gly Lys Gly Thr Thr Leu Arg Gly Arg Ser Asp Ala Asp Leu Val Val
65                  70                  75                  80

Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Val Cys Gln Arg Glu
            100                 105                 110

Glu Arg Ala Phe Ser Val Lys Phe Glu Val Gln Ala Pro Arg Trp Asp
            115                 120                 125

Asn Pro Arg Ala Leu Ser Phe Val Leu Ser Ser Leu Gln Leu Gly Glu
    130                 135                 140

Gly Val Glu Phe Asp Val Leu Pro Ala Phe Asp Ala Leu Gly Gln Leu
145                 150                 155                 160

Ile Gly Gly Tyr Lys Pro Asp Pro Gln Ile Tyr Val Lys Leu Ile Glu
                165                 170                 175

Glu Cys Thr Tyr Leu Gln Lys Glu Gly Glu Phe Ser Thr Cys Phe Thr
            180                 185                 190

Glu Leu Gln Arg Asp Phe Leu Lys Glu Arg Pro Thr Lys Leu Lys Ser
            195                 200                 205

Leu Ile Arg Leu Val Lys His Trp Tyr Gln Asn Cys Lys Lys Lys Leu
    210                 215                 220

Gly Lys Leu Pro Pro Gln Tyr Ala Leu Glu Leu Leu Thr Val Tyr Ala
225                 230                 235                 240

Trp Glu Arg Gly Ser Met Lys Thr His Phe Asn Thr Ala Gln Gly Phe
                245                 250                 255

Arg Thr Val Leu Glu Leu Val Ile Asn Tyr Gln Gln Leu Cys Ile Tyr
            260                 265                 270

Trp Thr Lys Tyr Tyr Asp Phe Lys Asn Pro Ile Ile Glu Lys Tyr Leu
            275                 280                 285

Ser Arg Gln Leu Glu Lys Pro Arg Pro Val Ile Leu Asp Pro Ala Asp
    290                 295                 300

Pro Thr Gly Asn Leu Gly Gly Asp Pro Lys Gly Trp Arg Gln Leu
305                 310                 315                 320

Ala Gln Glu Ala Glu Ala Trp Leu Asn Tyr Pro Cys Phe Lys Asn Xaa
            325                 330                 335

Asp Gly Ser Pro Val Ser Ser Trp Ile Leu Leu Thr Gln His Thr Pro
            340                 345                 350

Gly Ser Ile Arg Pro Thr Gly Arg Arg Gly Leu Asp Leu His His Pro
            355                 360                 365

Leu Asn Ala Ser Ala Ser Trp Gly Lys Gly Leu Gln Cys Tyr Leu Asp
    370                 375                 380

Gln Phe Leu His Phe Gln Val Gly Leu Leu Ile Gln Arg Gly Gln Ser
385                 390                 395                 400

Ser Ser Val Ser Trp Cys Ile Ile Gln Asp Arg Thr Gln Val Ser
                405                 410                 415

<210> SEQ ID NO 11
<211> LENGTH: 335
```

```
<212> TYPE: PRT
<213> ORGANISM: Pan troglodytes verus

<400> SEQUENCE: 11

Met Met Asp Leu Arg Asn Thr Pro Ala Lys Ser Leu Asp Lys Phe Ile
1               5                   10                  15

Glu Asp Tyr Leu Leu Pro Asp Lys Cys Phe Arg Lys Gln Ile Asn His
            20                  25                  30

Ala Ile Asp Ile Ile Cys Gly Phe Leu Lys Glu Arg Cys Phe Gln Gly
        35                  40                  45

Ser Ser Tyr Pro Val His Val Ser Lys Val Val Lys Gly Gly Ser Ser
    50                  55                  60

Gly Lys Gly Thr Thr Leu Arg Gly Arg Ser Asp Ala Asp Leu Val Val
65                  70                  75                  80

Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Ala Cys Gln Arg Glu
                100                 105                 110

Glu Arg Ala Phe Ser Val Lys Phe Glu Val Gln Ala Pro Arg Trp Asp
            115                 120                 125

Asn Pro Arg Ala Leu Ser Phe Val Leu Ser Ser Leu Gln Leu Gly Glu
        130                 135                 140

Gly Val Glu Phe Asp Val Leu Pro Ala Phe Asp Ala Leu Gly Gln Leu
145                 150                 155                 160

Thr Asp Gly Tyr Lys Pro Asp Pro Gln Ile Tyr Val Lys Leu Ile Glu
                165                 170                 175

Glu Cys Thr Tyr Leu Gln Lys Glu Gly Glu Phe Ser Thr Cys Phe Thr
                180                 185                 190

Glu Leu Gln Arg Asp Phe Leu Lys Gln Arg Pro Thr Lys Leu Lys Ser
            195                 200                 205

Leu Ile Arg Leu Val Lys His Trp Tyr Gln Asn Cys Lys Lys Lys Leu
        210                 215                 220

Gly Lys Leu Pro Pro Gln Tyr Ala Leu Glu Leu Leu Thr Val Tyr Ala
225                 230                 235                 240

Trp Glu Gln Gly Ser Met Glu Thr Asp Phe Asn Thr Ala Gln Glu Phe
                245                 250                 255

Arg Thr Val Leu Glu Leu Val Ile Asn Tyr Gln Gln Leu Cys Ile Tyr
                260                 265                 270

Trp Thr Lys Tyr Tyr Asp Phe Glu Asn Pro Ile Ile Glu Lys Tyr Leu
            275                 280                 285

Arg Arg Gln Leu Thr Lys Pro Arg Pro Val Ile Leu Asp Pro Ala Asp
        290                 295                 300

Pro Thr Gly Asn Leu Gly Gly Gly Asp Pro Lys Gly Trp Arg Gln Leu
305                 310                 315                 320

Ala Gln Glu Ala Glu Ala Trp Leu Asn Tyr Pro Cys Phe Lys Asn
                325                 330                 335

<210> SEQ ID NO 12
<211> LENGTH: 335
<212> TYPE: PRT
<213> ORGANISM: Pan troglodytes
<220> FEATURE:
<221> NAME/KEY: VARIANT
<222> LOCATION: 117
<223> OTHER INFORMATION: Xaa is Ser or Ala

<400> SEQUENCE: 12
```

Met Met Asp Leu Arg Asn Thr Pro Ala Lys Ser Leu Asp Lys Phe Ile
1               5                   10                  15

Glu Asp Tyr Leu Leu Pro Asp Lys Cys Phe Arg Lys Gln Ile Asn His
            20                  25                  30

Ala Ile Asp Ile Ile Cys Gly Phe Leu Lys Glu Arg Cys Phe Gln Gly
        35                  40                  45

Ser Ser Tyr Pro Val His Val Ser Lys Val Val Lys Gly Gly Ser Ser
    50                  55                  60

Gly Lys Gly Thr Thr Leu Arg Gly Arg Ser Asp Ala Asp Leu Val Val
65                  70                  75                  80

Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Ala Cys Gln Arg Glu
            100                 105                 110

Glu Arg Ala Phe Xaa Val Lys Phe Glu Val Gln Ala Pro Arg Trp Asp
            115                 120                 125

Asn Pro Arg Ala Leu Ser Phe Val Leu Ser Ser Leu Gln Leu Gly Glu
        130                 135                 140

Gly Val Glu Phe Asp Val Leu Pro Ala Phe Asp Ala Leu Gly Gln Leu
145                 150                 155                 160

Thr Asp Gly Tyr Lys Pro Asp Pro Gln Ile Tyr Val Lys Leu Ile Glu
                165                 170                 175

Glu Cys Thr Tyr Leu Gln Lys Glu Gly Glu Phe Ser Thr Cys Phe Thr
            180                 185                 190

Glu Leu Gln Arg Asp Phe Leu Lys Gln Arg Pro Thr Lys Leu Lys Ser
            195                 200                 205

Leu Ile Arg Leu Val Lys His Trp Tyr Gln Asn Cys Lys Lys Lys Leu
        210                 215                 220

Gly Lys Leu Pro Pro Gln Tyr Ala Leu Glu Leu Leu Thr Val Tyr Ala
225                 230                 235                 240

Trp Glu Gln Gly Ser Met Glu Thr Asp Phe Asn Thr Ala Gln Glu Phe
                245                 250                 255

Arg Thr Val Leu Glu Leu Val Ile Asn Tyr Gln Gln Leu Cys Ile Tyr
            260                 265                 270

Trp Thr Lys Tyr Tyr Asp Phe Glu Asn Pro Ile Ile Glu Lys Tyr Leu
            275                 280                 285

Arg Arg Gln Leu Thr Lys Pro Arg Pro Val Ile Leu Asp Pro Ala Asp
        290                 295                 300

Pro Thr Gly Asn Leu Gly Gly Gly Asp Pro Lys Gly Trp Arg Gln Leu
305                 310                 315                 320

Ala Gln Glu Ala Glu Ala Trp Leu Asn Tyr Pro Cys Phe Lys Asn
                325                 330                 335

<210> SEQ ID NO 13
<211> LENGTH: 118
<212> TYPE: PRT
<213> ORGANISM: Pongo pygmaeus abelii

<400> SEQUENCE: 13

Met Met Asp Leu Arg Asn Thr Pro Ala Lys Ser Leu Asp Lys Phe Ile
1               5                   10                  15

Glu Asp Tyr Leu Leu Pro Asp Thr His Phe Arg Met Gln Ile Asn His
            20                  25                  30

Ala Ile Asp Thr Ile Cys Gly Phe Leu Lys Glu Arg Cys Phe Arg Gly

```
                    35                  40                  45
Ser Ser Tyr Pro Ala Arg Val Ser Lys Val Lys Gly Gly Ser Ser
     50                  55                  60

Gly Lys Gly Thr Ala Leu Arg Gly Arg Ser Asp Ala Asp Leu Val Val
 65                  70                  75                  80

Phe Leu Ser Pro Leu Thr Thr Phe Gln Asp Gln Leu Asn Arg Arg Gly
                 85                  90                  95

Glu Phe Ile Gln Glu Ile Arg Lys Gln Leu Glu Ala Cys Gln Arg Glu
            100                 105                 110

Ser Ile Phe Arg Glu Val
        115

<210> SEQ ID NO 14
<211> LENGTH: 400
<212> TYPE: PRT
<213> ORGANISM: Pongo pygmaeus abelii
<220> FEATURE:
<221> NAME/KEY: VARIANT
<222> LOCATION: 113
<223> OTHER INFORMATION: Xaa is Ser or Arg
<220> FEATURE:
<221> NAME/KEY: VARIANT
<222> LOCATION: 114
<223> OTHER INFORMATION: Xaa is Ile or Ala
<220> FEATURE:
<221> NAME/KEY: VARIANT
<222> LOCATION: 116
<223> OTHER INFORMATION: Xaa is Arg or Ser
<220> FEATURE:
<221> NAME/KEY: VARIANT
<222> LOCATION: 117
<223> OTHER INFORMATION: Xaa is Glu or Val
<220> FEATURE:
<221> NAME/KEY: VARIANT
<222> LOCATION: 118
<223> OTHER INFORMATION: Xaa is Val or Lys
<220> FEATURE:
<221> NAME/KEY: VARIANT
<222> LOCATION: 119
<223> OTHER INFORMATION: Xaa is Phe or term
<220> FEATURE:
<221> NAME/KEY: VARIANT
<222> LOCATION: 142
<223> OTHER INFORMATION: Xaa is Arg or Gly
<220> FEATURE:
<221> NAME/KEY: VARIANT
<222> LOCATION: 363
<223> OTHER INFORMATION: Xaa is Pro or Gln

<400> SEQUENCE: 14

Met Met Asp Leu Arg Asn Thr Pro Ala Lys Ser Leu Asp Lys Phe Ile
 1               5                  10                  15

Glu Asp Tyr Leu Leu Pro Asp Thr His Phe Arg Met Gln Ile Asn His
                 20                  25                  30

Ala Ile Asp Thr Ile Cys Gly Phe Leu Lys Glu Arg Cys Phe Arg Gly
             35                  40                  45

Ser Ser Tyr Pro Val His Val Ser Lys Val Val Lys Gly Gly Ser Ser
     50                  55                  60

Gly Lys Gly Thr Ala Leu Arg Gly Arg Ser Asp Ala Asp Leu Val Val
 65                  70                  75                  80

Phe Leu Ser Pro Leu Thr Thr Phe Gln Asp Gln Leu Asn Arg Arg Gly
                 85                  90                  95

Glu Phe Ile Gln Glu Ile Arg Lys Gln Leu Glu Ala Cys Gln Arg Glu
            100                 105                 110

Xaa Xaa Phe Xaa Xaa Xaa Xaa Glu Val Gln Ala Pro Arg Trp Asp Asn
```

```
            115                 120                 125
Pro Arg Ala Leu Ser Phe Val Leu Ser Ser Phe Gln Leu Xaa Glu Gly
130                 135                 140

Val Glu Phe Asp Val Leu Pro Ala Phe Asp Ala Leu Gly Gln Leu Thr
145                 150                 155                 160

Gly Gly Tyr Lys Pro Asp Pro Gln Ile Tyr Val Lys Leu Ile Glu Glu
                165                 170                 175

Cys Thr Asp Leu Gln Lys Glu Gly Phe Ser Thr Cys Phe Thr Glu
                180                 185                 190

Leu Gln Arg Asp Phe Leu Lys Gln Arg Pro Thr Lys Leu Lys Ser Leu
            195                 200                 205

Ile Arg Leu Val Lys His Trp Tyr Gln Asn Cys Lys Lys Leu Gly
210                 215                 220

Lys Leu Pro Pro Gln Tyr Ala Leu Glu Leu Leu Thr Val Tyr Ala Trp
225                 230                 235                 240

Glu Arg Gly Ser Met Lys Thr His Phe Asn Thr Ala Gln Gly Phe Arg
                245                 250                 255

Thr Val Leu Glu Leu Val Ile Asn Tyr Gln Gln Leu Cys Ile Tyr Trp
                260                 265                 270

Thr Lys Tyr Tyr Asp Phe Lys Asn Pro Ile Ile Lys Lys Tyr Leu Ser
            275                 280                 285

Arg Gln Leu Arg Lys Pro Arg Pro Val Ile Leu Asp Pro Ala Asp Pro
290                 295                 300

Thr Gly Asn Leu Gly Gly Gly Asp Pro Ile Gly Trp Arg Gln Leu Ala
305                 310                 315                 320

Gln Glu Ala Glu Ala Trp Leu Asn Tyr Pro Cys Phe Lys Asn Trp Asp
                325                 330                 335

Gly Ser Pro Val Ser Ser Trp Ile Leu Leu Ala Glu Ser Asp Ser Glu
                340                 345                 350

Asp Asp Glu Thr Tyr Asp Pro Arg Met Tyr Xaa Lys Tyr Gly Tyr Ile
            355                 360                 365

Arg Thr His Glu Tyr Ser His Phe Ser His Ser Pro Ser Thr Leu Gln
370                 375                 380

Ala Ala Ser Thr Pro Gln Ala Glu Glu Asn Trp Thr Cys Thr Ile Leu
385                 390                 395                 400

<210> SEQ ID NO 15
<211> LENGTH: 364
<212> TYPE: PRT
<213> ORGANISM: Pongo pygmaeus abelii
<220> FEATURE:
<221> NAME/KEY: VARIANT
<222> LOCATION: 113
<223> OTHER INFORMATION: Xaa is Ser or Arg
<220> FEATURE:
<221> NAME/KEY: VARIANT
<222> LOCATION: 114
<223> OTHER INFORMATION: Xaa is Ile or Ala
<220> FEATURE:
<221> NAME/KEY: VARIANT
<222> LOCATION: 116
<223> OTHER INFORMATION: Xaa is Arg or Ser
<220> FEATURE:
<221> NAME/KEY: VARIANT
<222> LOCATION: 117
<223> OTHER INFORMATION: Xaa is Glu or Val
<220> FEATURE:
<221> NAME/KEY: VARIANT
<222> LOCATION: 118
<223> OTHER INFORMATION: Xaa is Val or Lys
<220> FEATURE:
```

```
<221> NAME/KEY: VARIANT
<222> LOCATION: 119
<223> OTHER INFORMATION: Xaa is Phe or term
<220> FEATURE:
<221> NAME/KEY: VARIANT
<222> LOCATION: 142
<223> OTHER INFORMATION: Xaa is Arg or Gly

<400> SEQUENCE: 15

Met Met Asp Leu Arg Asn Thr Pro Ala Lys Ser Leu Asp Lys Phe Ile
 1               5                  10                  15

Glu Asp Tyr Leu Leu Pro Asp Thr His Phe Arg Met Gln Ile Asn His
             20                  25                  30

Ala Ile Asp Thr Ile Cys Gly Phe Leu Lys Glu Arg Cys Phe Arg Gly
         35                  40                  45

Ser Ser Tyr Pro Val His Val Ser Lys Val Val Lys Gly Gly Ser Ser
     50                  55                  60

Gly Lys Gly Thr Ala Leu Arg Gly Arg Ser Asp Ala Asp Leu Val Val
 65                  70                  75                  80

Phe Leu Ser Pro Leu Thr Thr Phe Gln Asp Gln Leu Asn Arg Arg Gly
                 85                  90                  95

Glu Phe Ile Gln Glu Ile Arg Lys Gln Leu Glu Ala Cys Gln Arg Glu
            100                 105                 110

Xaa Xaa Phe Xaa Xaa Xaa Xaa Glu Val Gln Ala Pro Arg Trp Asp Asn
            115                 120                 125

Pro Arg Ala Leu Ser Phe Val Leu Ser Ser Phe Gln Leu Xaa Glu Gly
130                 135                 140

Val Glu Phe Asp Val Leu Pro Ala Phe Asp Ala Leu Gly Gln Leu Thr
145                 150                 155                 160

Gly Gly Tyr Lys Pro Asp Pro Gln Ile Tyr Val Lys Leu Ile Glu Glu
                165                 170                 175

Cys Thr Asp Leu Gln Lys Glu Gly Glu Phe Ser Thr Cys Phe Thr Glu
            180                 185                 190

Leu Gln Arg Asp Phe Leu Lys Gln Arg Pro Thr Lys Leu Lys Ser Leu
        195                 200                 205

Ile Arg Leu Val Lys His Trp Tyr Gln Asn Cys Lys Lys Lys Leu Gly
210                 215                 220

Lys Leu Pro Pro Gln Tyr Ala Leu Glu Leu Leu Thr Val Tyr Ala Trp
225                 230                 235                 240

Glu Arg Gly Ser Met Lys Thr His Phe Asn Thr Ala Gln Gly Phe Arg
                245                 250                 255

Thr Val Leu Glu Leu Val Ile Asn Tyr Gln Gln Leu Cys Ile Tyr Trp
            260                 265                 270

Thr Lys Tyr Tyr Asp Phe Glu Asn Pro Ile Ile Lys Lys Tyr Leu Ser
        275                 280                 285

Arg Gln Leu Arg Lys Pro Arg Pro Val Ile Leu Asp Pro Ala Asp Pro
290                 295                 300

Thr Gly Asn Leu Gly Gly Gly Asp Pro Ile Gly Trp Arg Gln Leu Ala
305                 310                 315                 320

Gln Glu Ala Glu Ala Trp Leu Asn Tyr Pro Cys Phe Lys Asn Trp Asp
                325                 330                 335

Gly Ser Pro Val Ser Ser Trp Ile Leu Leu Val Arg Pro Pro Ala Ser
            340                 345                 350

Ser Leu Pro Phe Ile Pro Ala Pro Leu His Glu Ala
        355                 360
```

```
<210> SEQ ID NO 16
<211> LENGTH: 414
<212> TYPE: PRT
<213> ORGANISM: Pongo pygmaeus abelii
<220> FEATURE:
<221> NAME/KEY: VARIANT
<222> LOCATION: 113
<223> OTHER INFORMATION: Xaa is Ser or Arg
<220> FEATURE:
<221> NAME/KEY: VARIANT
<222> LOCATION: 114
<223> OTHER INFORMATION: Xaa is Ile or Ala
<220> FEATURE:
<221> NAME/KEY: VARIANT
<222> LOCATION: 116
<223> OTHER INFORMATION: Xaa is Arg or Ser
<220> FEATURE:
<221> NAME/KEY: VARIANT
<222> LOCATION: 117
<223> OTHER INFORMATION: Xaa is Glu or Val
<220> FEATURE:
<221> NAME/KEY: VARIANT
<222> LOCATION: 118
<223> OTHER INFORMATION: Xaa is Val or Lys
<220> FEATURE:
<221> NAME/KEY: VARIANT
<222> LOCATION: 119
<223> OTHER INFORMATION: Xaa is Phe or term
<220> FEATURE:
<221> NAME/KEY: VARIANT
<222> LOCATION: 142
<223> OTHER INFORMATION: Xaa is Arg or Gly

<400> SEQUENCE: 16

Met Met Asp Leu Arg Asn Thr Pro Ala Lys Ser Leu Asp Lys Phe Ile
 1               5                  10                  15

Glu Asp Tyr Leu Leu Pro Asp Thr His Phe Arg Met Gln Ile Asn His
             20                  25                  30

Ala Ile Asp Thr Ile Cys Gly Phe Leu Lys Glu Arg Cys Phe Arg Gly
         35                  40                  45

Ser Ser Tyr Pro Val His Val Ser Lys Val Val Lys Gly Gly Ser Ser
     50                  55                  60

Gly Lys Gly Thr Ala Leu Arg Gly Arg Ser Asp Ala Asp Leu Val Val
65                  70                  75                  80

Phe Leu Ser Pro Leu Thr Thr Phe Gln Asp Gln Leu Asn Arg Arg Gly
                 85                  90                  95

Glu Phe Ile Gln Glu Ile Arg Lys Gln Leu Glu Ala Cys Gln Arg Glu
            100                 105                 110

Xaa Xaa Phe Xaa Xaa Xaa Xaa Glu Val Gln Ala Pro Arg Trp Asp Asn
        115                 120                 125

Pro Arg Ala Leu Ser Phe Val Leu Ser Ser Phe Gln Leu Xaa Glu Gly
    130                 135                 140

Val Glu Phe Asp Val Leu Pro Ala Phe Asp Ala Leu Gly Gln Leu Thr
145                 150                 155                 160

Gly Gly Tyr Lys Pro Asp Pro Gln Ile Tyr Val Lys Leu Ile Glu Glu
                165                 170                 175

Cys Thr Asp Leu Gln Lys Glu Gly Glu Phe Ser Thr Cys Phe Thr Glu
            180                 185                 190

Leu Gln Arg Asp Phe Leu Lys Gln Arg Pro Thr Lys Leu Lys Ser Leu
        195                 200                 205

Ile Arg Leu Val Lys His Trp Tyr Gln Asn Cys Lys Lys Lys Leu Gly
    210                 215                 220

Lys Leu Pro Pro Gln Tyr Ala Leu Glu Leu Leu Thr Val Tyr Ala Trp
```

-continued

```
            225                 230                 235                 240

Glu Arg Gly Ser Met Lys Thr His Phe Asn Thr Ala Gln Gly Phe Arg
                245                 250                 255

Thr Val Leu Glu Leu Val Ile Asn Tyr Gln Gln Leu Cys Ile Tyr Trp
                260                 265                 270

Thr Lys Tyr Tyr Asp Phe Glu Asn Pro Ile Ile Lys Lys Tyr Leu Ser
            275                 280                 285

Arg Gln Leu Lys Lys Pro Arg Pro Val Ile Leu Asp Pro Ala Asp Pro
        290                 295                 300

Thr Gly Asn Leu Gly Gly Gly Asp Pro Ile Gly Trp Arg Gln Leu Ala
305                 310                 315                 320

Gln Glu Ala Glu Ala Trp Leu Asn Tyr Pro Cys Phe Lys Asn Trp Asp
                325                 330                 335

Gly Ser Pro Val Ser Ser Trp Ile Leu Leu Pro Gln His Thr Pro Gly
                340                 345                 350

Ser Ile His Pro Thr Gly Arg Arg Glu Leu Asp Val His His Pro Leu
            355                 360                 365

Asn Ala Ser Ala Ser Trp Gly Lys Gly Leu Gln Cys Tyr Leu Asp His
        370                 375                 380

Leu Leu His Phe Gln Val Gly Leu Leu Ile Gln Arg Gly Gln Arg Ser
385                 390                 395                 400

Ser Val Ser Trp Cys Ile Ile Gln Asp Arg Thr Gln Val Ser
                405                 410
```